US009447101B2

(12) United States Patent
Yang et al.

(10) Patent No.: US 9,447,101 B2
(45) Date of Patent: Sep. 20, 2016

(54) **PYRROLO[2,1-*F*][1,2,4]TRIAZINE COMPOUND, AND PREPARATION METHOD AND APPLICATION THEREOF**

(71) Applicants: Shanghai Institute of Materia Medica, Chinese Academy of Sciences, Shanghai (CN); Shanghai Haihe Pharmaceutical Co., Ltd., Shanghai (CN)

(72) Inventors: Chunhao Yang, Shanghai (CN); Linghua Meng, Shanghai (CN); Yanhong Chen, Shanghai (CN); Xiang Wang, Shanghai (CN); Cun Tan, Shanghai (CN); Jiapeng Li, Shanghai (CN); Jian Ding, Shanghai (CN); Yi Chen, Shanghai (CN)

(73) Assignees: Shanghai Institute of Materia Medica, Chinese Academy of Sciences, Shanghai (CN); Shanghai Haihe Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 14/403,014

(22) PCT Filed: Apr. 23, 2013

(86) PCT No.: PCT/CN2013/074559
§ 371 (c)(1),
(2) Date: Nov. 21, 2014

(87) PCT Pub. No.: WO2013/177983
PCT Pub. Date: Dec. 5, 2013

(65) Prior Publication Data
US 2015/0141644 A1 May 21, 2015

(30) Foreign Application Priority Data

May 31, 2012 (CN) .......................... 2012 1 0177980

(51) Int. Cl.
| | | |
|---|---|---|
| *C07D 419/04* | (2006.01) | |
| *C07D 419/14* | (2006.01) | |
| *A61K 31/5377* | (2006.01) | |
| *A61K 31/5386* | (2006.01) | |
| *A61K 31/53* | (2006.01) | |
| *A61P 35/00* | (2006.01) | |
| *C07D 487/04* | (2006.01) | |
| *C07D 519/00* | (2006.01) | |
| *C07D 498/08* | (2006.01) | |

(52) U.S. Cl.
CPC ......... *C07D 487/04* (2013.01); *A61K 31/5377* (2013.01); *A61K 31/5386* (2013.01); *C07D 498/08* (2013.01); *C07D 519/00* (2013.01)

(58) Field of Classification Search
CPC .. C07D 419/04; C07D 419/14; A61K 31/53; A61K 31/5377

USPC ............ 544/112, 183; 514/231.5, 232.8, 242
See application file for complete search history.

(56) References Cited

U.S. PATENT DOCUMENTS

| | | |
|---|---|---|
| 2006/0084650 A1 | 4/2006 | Dong et al. |
| 2006/0089358 A1 | 4/2006 | Gavai et al. |
| 2008/0009497 A1 | 1/2008 | Wittman et al. |

FOREIGN PATENT DOCUMENTS

| | | |
|---|---|---|
| CN | 102675323 A | 9/2012 |
| WO | WO 2004/009784 A2 | 1/2004 |
| WO | WO 2004/043912 A2 | 5/2004 |
| WO | WO 2004/054514 A2 | 7/2004 |
| WO | WO 2005/066176 A1 | 7/2005 |
| WO | WO 2006/069395 A2 | 6/2006 |
| WO | WO 2007/005709 A1 | 1/2007 |
| WO | WO 2007/061882 A2 | 5/2007 |
| WO | WO 2008/083398 A2 | 7/2008 |
| WO | WO 2008/131050 A1 | 10/2008 |
| WO | WO 2009/136966 A1 | 11/2009 |
| WO | WO 2010/002472 A1 | 1/2010 |
| WO | WO 2011/089400 A1 | 7/2011 |

OTHER PUBLICATIONS

Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Klempner et al.Cancer Discov. Dec. 2013;3(12):1345-54.*
Massacesi et al. Ann. N.Y. Acad. Sci. 1280 (2013) 19-23.*
Gautschi et al., Clin. Cancer Res., 14(6), 1639-1648, 2008.*
Mountzios et al., Cancer Treatments Reviews, 34, 175-182, 2008.*
Mass, R. D., Int. J. Radiation Oncology Bio. Phys.vol. 58(3): 932-940, 2004.*
Fabbro et al. Pharmacology & therapeutics 93, 79-98, 2002.*
Cecil Textbook of Medicine, edited by Bennet, J.C., and Plum F., 20th edition,vol. 1, 1004-101 O, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
International Search Report and Written Opinion for International Application No. PCT/CN2013/074559 mailed Aug. 1, 2013.

(Continued)

*Primary Examiner* — Venkataraman Balasubramanian
(74) *Attorney, Agent, or Firm* — Wolf, Greenfield & Sacks, P.C.

(57) ABSTRACT

The present invention relates to a pyrrolo[2,1-f][1,2,4]triazine compound, an isomer thereof or a pharmaceutically acceptable salt, ester or hydrate thereof, and a preparation method and application thereof. The pyrrolo[2,1-f][1,2,4] triazine compound has a structure expressed in general formula (I). The pyrrolo[2,1-f][1,2,4]triazine compound expressed in general formula (I) can inhibit a phosphatidylinositol-3 kinase (PI3K) signal pathway, thereby being used to prepare medicine for treating phosphatidylinositol-3 kinase related diseases such as cancer.

11 Claims, 1 Drawing Sheet

(56) References Cited

OTHER PUBLICATIONS

International Preliminary Report on Patentability Chapter I for International Application No. PCT/CN2013/074559 mailed Dec. 11, 2014.

Abraham et al, Novel series of pyrrolotriazine analogs as highly potent pan-Aurora kinase inhibitors. Bioorg Med Chem Lett. Sep. 15, 2011;21(18):5296-300. doi: 0.1016/j.bmcl.2011.07.027. Epub Jul. 14, 2011.

Cai et al., Discovery of brivanib alaninate ((S)-((R)-1-(4-(4-fluoro-2-methyl-1H-indol-5-yloxy)-5-methylpyrrolo[2,1-f][1,2,4] triazin-6-yloxy)propan-2-yl)2-aminopropanoate), a novel prodrug of dual vascular endothelial growth factor receptor-2 and fibroblast growth factor receptor-1 kinase inhibitor (BMS-540215). J Med Chem. Mar. 27, 2008;51(6):1976-80. doi: 10.1021/jm7013309. Epub Feb. 21, 2008.

Engelman et al., Targeting PI3K signalling in cancer: opportunities, challenges and limitations. Nat Rev Cancer. Aug. 2009;9(8):550-62. doi: 10.1038/nrc2664. Review.

Engelman et al., The evolution of phosphatidylinositol 3-kinases as regulators of growth and metabolism. Nat Rev Genet. Aug. 2006;7(8):606-19. Review.

Gaullier et al., FYVE finger proteins as effectors of phosphatidylinositol 3-phosphate. Chem Phys Lipids. Apr. 1999;98(1-2):87-94. Review.

Gavai et al., Discovery and preclinical evaluation of [4-[[1-(3-fluorophenyl)methyl]-1H-indazol-5-ylamino]-5-methylpyrrolo [2,1-f][1,2,4 ]triazin-6-yl]carbamic acid, (3S)-3-morpholinylmethyl ester (BMS-599626), a selective and orally efficacious inhibitor of human epidermal growth factor receptor 1 and 2 kinases. J Med Chem. Nov. 12, 2009;52(21):6527-30. doi:10.1021/jm9010065.

Hayashi et al., C-Nucleosides.17.[1] A Synthesis of 2-Substituted 7(β-D-Ribofuranosyl)- Pyrrolo (2,1-f-1,2,1,2,4-Triazines. A new type of "Purine Like" C-Nucleoside. Heterocycles. 1992; 34(3):569-74.

Hunt et al, Discovery of the pyrrolo[2,1-f][1,2,4]triazine nucleus as a new kinase inhibitor template. J Med Chem. Jul. 29, 2004;47(16):4054-9.

Kamijo et al., Copper- or phosphine-catalyzed reaction of alkynes with isocyanides. Regioselective synthesis of substituted pyrroles controlled by the catalyst. J Am Chem Soc. Jun. 29, 2005;127(25):9260-6.

Liu et al., Discovery of 4-(5-(cyclopropylcarbamoyl)-2-methylphenylamino)-5-methyl-N-propylpyrrolo[1,2-f][1,2,4]triazine-6-carboxamide (BMS-582949), a clinical p38α MAP kinase inhibitor for the treatment of inflammatory diseases. J Med Chem. Sep. 23, 2010;53(18):6629-39. doi: 10.1021/jm100540x.

Mesaros et al., Strategies to mitigate the bioactivation of 2-anilino-7-aryl-pyrrolo[2,1-f][1,2,4]triazines: identification of orally bioavailable, efficacious ALK inhibitors. J Med Chem. Jan. 12, 2012;55(1):115-25. doi: 10.1021/jm2010767. Epub Dec. 29, 2011.

Patil et al., 4-Aza-7,9-Dideazaadenosine, a New Cytotoxic Synthesis C-Nucleoside Analogue of Adenosine.Tetrahedron Ltrs.Jul. 25, 1994;v35:p. 5339-42. doi:10.1016/S0040-4039(00)73494-0.

Schroeder et al., Identification of pyrrolo[2,1-f][1,2,4]triazine-based inhibitors of Met kinase. Bioorg Med Chem Lett. Mar. 15, 2008;18(6):1945-51. doi: 10.1016/j.bmcl.2008.01.121. Epub Feb. 7, 2008.

Thieu et al., Discovery and process synthesis of novel 2,7-pyrrolo[2,1-f][1,2,4]triazines. Org Lett. Aug. 19, 2011;13(16):4204-7. doi: 10.1021/012015237. Epub Jul. 26, 2011.

Vanhaesebroeck et al., Synthesis and function of 3-phosphorylated inositol lipids. Annu Rev Biochem. 2001;70:535-602. Review.

Wang et al., Discovery and bioactivity of 4-(2-arylpyrido[3',2':3,4]pyrrolo[1,2-f][1,2,4]triazin-4-yl) morpholine derivatives as novel PI3K inhibitors. Bioorg Med Chem Lett. Jan. 1, 2012;22(1):339-42. doi: 10.1016/j.bmcl.2011.11.003. Epub Nov. 9, 2011.

Weinberg et al., 2,7-Pyrrolo[2,1-f][1,2,4]triazines as JAK2 inhibitors: modification of target structure to minimize reactive metabolite formation. Bioorg Med Chem Lett. Dec. 15, 2011;21(24):7325-30. doi: 10.1016/j.bmcl.2011.10.032. Epub Oct. 14, 2011.

Wittman et al., Discovery of a 2,4-disubstituted pyrrolo[1,2-f][1,2,4]triazine inhibitor (BMS-754807) of insulin-like growth factor receptor (IGF-1R) kinase in clinical development. J Med Chem. Dec. 10, 2009;52(23):7360-3. doi: 10.1021/jm900786r.

\* cited by examiner

PYRROLO[2,1-F][1,2,4]TRIAZINE COMPOUND, AND PREPARATION METHOD AND APPLICATION THEREOF

This application is a national stage filing under 35 U.S.C. §371 of international PCT application PCT/CN2013/074559, filed Apr. 23, 2013, which claims priority to China application number CN201210177980.3, filed May 31, 2012. The entire content of each of the prior applications is herein incorporated by reference.

TECHNICAL FIELD

The invention relates to pyrrolo[2,1-f][1,2,4]triazine derivatives as shown in general formula I, isomers thereof or pharmaceutically acceptable salts, esters or hydrates thereof, and preparation method and use thereof. Compounds I as shown in general formula I can inhibit phosphatidylinositol 3-kinase (PI3K) signal pathway, thereby being used to prepare medicaments for treating phosphatidylinositol 3-kinase related diseases, such as cancer.

BACKGROUND

PI3K is a lipid kinase and can phosphorylate 3-position of inositol ring in phosphatidylinositol to form phosphatidylinositol-3-phosphate (PIP), phosphatidylinositol-3,4-diphosphate (PIP2) and phosphatidylinositol-3,4, 5-triphosphate (PIP3). PIP, PIP2 and PIP3, as important second messengers, bind and activate various proteins containing PH domain (pleckstrin homology domain), FYVE domain (named after the first letter of Fablp, YOTB, Vaclp and EEA1 proteins containing FYVE domain found originally, see Gaullier, J. M.; Simonsen, A.; D'Arrigo, A.; Bremnes, B.; Stenmark, H., *Chem. Phys. Lipids,* 1999, 98: 87-94), PX domain (Phox homology domain) and other phospholipid-binding region, to form a signaling cascade complex, and ultimately regulate cell activities such as proliferation, differentiation, survival and migration etc. (see Vanhaesebroeck, B.; Leevers, S. J.; Ahmadi, K.; Timms, J.; Katso, R.; Driscoll, P. C.; Woscholski, R.; Parker, P. J.; Waterfield, M. D., *Annu. Rev. Biochem.,* 2001, 70: 535-602).

Depending on the differences in gene sequence, the substrate specificity and function, PI3K superfamily is grouped into three classes: I, II and III PI3K. Class I PI3Ks are most widely studied class by far. The substrates of PI3Ks are phosphatidylinositol (PI), phosphatidylinositol-4-phosphate (PI(4)P), phosphatidylinositol 4, 5-bisphosphate (PI(4,5)P2). Class I PI3Ks are heterodimeric molecules composed of one catalytic subunit and one regulatory subunit. Class I PI3Ks can be further divided into two categories due to the difference in the regulatory subunit and activation mechanism: PI3K IA and PI3K IB. Wherein, PI3K IA comprises PI3Kα, PI3Kβ and PI3Kδ, and is acted by receptor tyrosine kinase; while PI3K IB only consists of PI3Kγ and is acted by G protein-coupled receptors. PI and PI(4)P are substrates of class II PI3Ks. Class II PI3Ks include PI3KC2α, PI3KC2β and PI3KC2γ. They are characterized by a C2 domain at the C terminus, indicating that their activities are regulated by calcium ion. The substrate of class III PI3K is PI. Its activation mechanism remains unclear up to now (see, Engelman, J. A.; Luo, J.; Cantley, L. C., *Nat. Rev. Genet.,* 2006, 7: 606-619).

Hyper-activation of PI3K initiates phosphatidylinositol 3-kinase/protein kinase B/mammalian target protein of rapamycin (PI3K/Akt/mTOR) signal pathway and promotes cell survival and proliferation, which is frequently present in about 60% of human tumors. PTEN (phosphatase and tensin homolog deleted on chromosome 10) acts as a tumor suppressor and dephosphorylate 3-position at inositol ring of phosphatidylinositol and antagonize the activity of PI3K. Such function is lost in many cancers. Active mutation in gene PIK3CA encoding p110α is present in over 30% of cancers. Moreover, gene amplifications of PI3K3CA and protein kinase B (Akt) have been frequently found in other cancers which also contribute to the expression of protein (see Engelman, J. A., *Nat. Rev. Cancer,* 2009, 9: 550-562). These facts indicate that PI3K is closely related to the tumorigenesis and promotion. The target protein of rapamycin (mTOR) is one of important downstream protein of protein kinase B, which is a serine/threonine kinase. Protein kinase B further activates the target protein of rapamycin by directly phosphorylating mTOR; or indirectly enhancing the activation of mTOR by inactivating tumor suppressor gene TSC2 (Tuberous sclerosis protein 2). The active mTOR directly or indirectly takes part in regulations of various processes relating to cell proliferation and growth, such as the initial stage of translation, transcription, microfilament rest action, membrane transport, protein degradation, protein kinase C (PKC) pathway, ribosomal protein synthesis and tRNA synthesis etc by regulating downstream signaling pathways, such as ribosome S6 kinase (S6K1, or P70S6K), eukaryotic cells translation initiation factor 4E (eIF-4 e) binding protein 1 (4E-BP1), signal transduction and transcription activation factor 3 (STAT3), etc. Therefore, mTOR is a center regulatory protein of cell growth and proliferation and has become a new antitumor drug target.

PI3K and downstream signaling protein mTOR inhibitors are a class of promising antitumor drugs. At present, several pan-PI3K inhibitors, such as GDC-0941, XL-147, PX-866, etc. have entered into clinical studies. However, the number and structure diversity need to be expanded to meet the needs of research and development of new anticancer drug. Meanwhile, there are defects existing in known inhibitors. For example, PX-866, which is derived from Wortmannin, is difficult to be synthesized; and the activity of GDC-0941 needs to be improved. Therefore, discovery and development of antitumor drugs targeting PI3K with higher activity, better safety attract increasing interest world wide.

Pyrrolo[2,1-f][1,2,4]triazine is a privileged structure in medicinal chemistry. After this privileged structure was reported as purine analogues (see: Hayashi, M.; Araki, A.; Maeba, I., *Heterocycles,* 1992, 34: 569-574. Patil, S. A.; Otter, B. A.; Klein, R. S., *Tetrahedron Lett.,* 1994, 35: 5339-5342), more and more compounds containing such privileged structure were synthesized and displayed a variety of biological activities, for example, acting as JAK2 inhibitors (see: Weinberg, L. R.; Albom, M. S.; Angeles, T. S. et al., *Bioorg. Med. Chem. Lett.* 2001, 21: 7325-7330), pan-Aurora kinase inhibitors (Abraham, S.; Hadd, M. J.; Tran, L. et al., *Bioorg. Med. Chem. Lett* 2011, 21: 5296-5300), p38α mitogen-activated protein kinase (p38α MAPK) inhibitors (Liu, C.; Lin, J.; Wrobleski, S. T. et al., *J. Med. Chem.,* 2010, 53: 6629-6639), lymphoma kinase ALK inhibitors (Mesaros, E. F.; Thieu, T. V.; Wells, G. J. et al., *J. Med. Chem.,* 2012, 55: 115-125), VEGFR-2/FGFR-1 dual inhibitors (Cai, Z.-w.; Zhang, Y.; Borzilleri, R. M. et al., *J. Med. Chem.,* 2008, 5: 1976-1980), VEGFR-2 inhibitors (Hunt, J. T.; Mitt, T.; Borzilleri, R. et al., *J. Med. Chem.,* 2004, 47: 4054-4059), EGFR1/2 inhibitors (Gavai, A. V.; Fink, B. E.; Fairfax, D. J. et al., *J. Med. Chem.,* 2009, 52: 6527-6530), IGF-1R inhibitors (see: Wittman, M. D.; Carboni, J. M.; Yang, Z. et al. *J. Med. Chem.,* 2009, 52: 7360-7363), or Met kinase inhibitors (see: Schroeder, G. M.;

Chen, X.-T.; Williams, D. K. et al., *Bioorg. Med. Chem. Lett.,* 2007, 18: 1945-1951). Moreover, compounds containing this pyrrolo[2,1-f][1,2,4]triazine privileged structure such as EGFR inhibitor AC-480 (WO-2004054514), VEGF-2 receptor antagonist BMS-690514 (WO2005/066176A1), and IGF-1R antagonist BMS-754807 (US2008/0009497 A1) etc. have entered into the clinical studies. The synthetic methods for the core structure of pyrrolo[2,1-f][1,2,4]triazine have also been reported, for example, Thieu, T; Sclafani, J. A.; Levy, D. V et al., *Org. Lett.,* 2011, 13: 4204-4207. In addition to above mentioned literatures, there are many patent applications related to the core structure of pyrrolo[2,1-f][1,2,4]triazine, for example, acting as kinase inhibitors (publication No.: US2006/0084650A1), EGFR kinase inhibitors (Publication No.: US2006/0089358A1, WO2006/069395), VEGFR-2 and FGFR-1 inhibitors (Publication No.: WO2004/009784, WO2004/043912), and patent applications related to the synthetic methods for intermediates (WO2007/005709, WO2008/083398), tyrosine receptor kinase inhibitors (WO2007/061882, WO2008/131050), Aurora kinase inhibitors (Publication Number: WO2009/136966), JAK kinase inhibitors (Publication No.: WO2010/002472). The reported pyrrolo[2,1-f][1,2,4]triazines mentioned above do not cover and relate to the compounds of the present invention and use thereof as PI3K inhibitors.

Based on the aforementioned reasons, the inventors designed and synthesized a series of PI3K inhibitors with pyrrole[2,1-f][1,2,4]triazine as core structure. The compounds in the present invention have demonstrated excellent bioactivity both in vitro and in vivo, and are expected to be developed into a novel anti-cancer medicament.

SUMMARY OF THE INVENTION

The object of the present invention is to provide a novel type of pyrrolo[2,1-f][1,2,4]triazine derivatives as shown in general formula I.

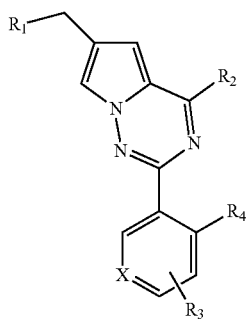

I

Wherein,
X=CH or N;
$R_1$ is $-NR_5R_6$;
$R_2$ is

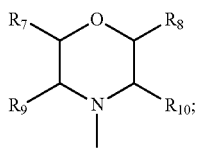

$R_3$ is $-NH_2$, $-NHC(O)NHR_{11}$, $-NHC(O)OR_{11}$, $-CH_2OH$, $-CH_2S(O)_2R_{12}$, $-CH_2OS(O)_2R_{12}$ or $-CH_2NHS(O)_2R_{12}$;

$R_4$ is H or $CF_3$;

$R_5$ and $R_6$ are each independently a C1-C4 alkyl, or combined with the nitrogen atom to which they are attached to form an unsubstituted saturated heterocycle or a saturated heterocycle substituted by substituent(s), preferably a pyrrolidyl, a piperidinyl and a piperazinyl, most preferably a piperazinyl; the substituent is $-S(O)_2R_{12}$;

$R_7$, $R_8$, $R_9$ and $R_{10}$ are each independently H or C1-C3 alkyl; alternatively, $R_7$ and $R_8$, or $R_9$ and $R_{10}$ are combined with the carbon atom to which they are attached to form a 5-8 membered saturated ring; preferably, $R_7$ and $R_8$, or $R_9$ and $R_{10}$, with the carbon atoms to which they are attached as bridge carbon atoms, form bridged bicyclo-heterocycle with morpholine ring;

$R_{11}$ is a C1-C4 alkyl, an unsubstituted C3-C6 cycloalkyl or a C3-C6 cycloalkyl substituted by one or more substituents, an unsubstituted benzyl or a benzyl substituted by one or more substituents, an unsubstituted phenyl or a phenyl substituted by one or more substituents, an unsubstituted isoxazolyl or an isoxazolyl substituted by one or more substituents, or an unsubstituted pyridyl or a pyridyl substituted by one or more substituents, the one or more substituents are selected from a halogen, a C1-C3 alkyl, or a C1-C3 alkoxyl, $-CF_3$, $-C(O)OR_{12}$, $-C(O)NR_{12}R_{15}$,

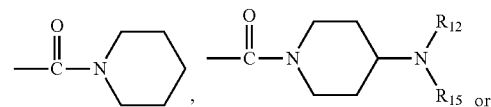

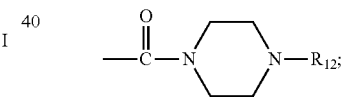

$R_{12}$ and $R_{15}$ are each independently C1-C3 alkyl.

Preferably, the structure of general formula I is shown as follows:

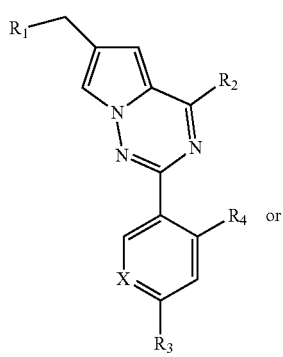

A

-continued

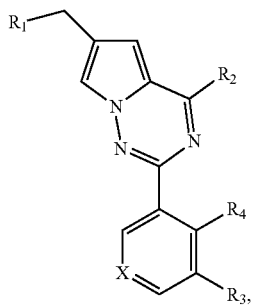

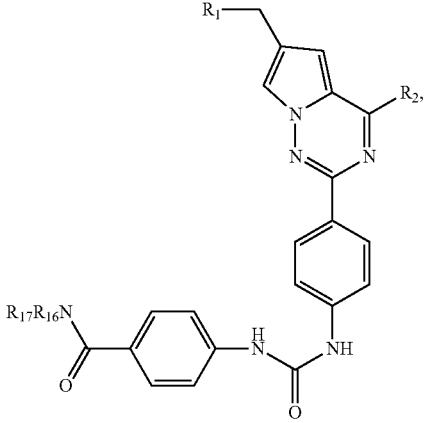

wherein X, $R_1$, $R_2$, $R_3$ and $R_4$ are defined as above.

More preferably, $R_1$ is dimethylamino or 1-methylsulfonyl piperazinyl;

$R_2$ is morpholinyl, (S)-3-methylmorpholinyl, or 8-oxa-3-azabicyclo[3.2.1]octan-3-yl;

$R_3$ is —NHC(O)NHR$_{11}$, —NHC(O)OR$_{11}$, —CH$_2$S(O)$_2$Me, or —CH$_2$NHS(O)$_2$Me;

$R_4$ is H or —CF$_3$;

$R_{11}$ is a methyl, an ethyl, a propyl, a cyclopropyl, a tert-butyl, an iso-butyl, a 4-fluorobenzyl, an unsubstituted phenyl or a phenyl substituted by one or more substituents, an unsubstituted isoxazolyl or an isoxazolyl substituted by one or more substituents, or an unsubstituted pyridine ring or a pyridine ring substituted by one or more substituents, and the substituent is selected from a fluorine, a chlorine, a trifluoromethyl, a methyl, a methoxy, an ethoxycarbonyl, a dimethylaminocarbonyl, a 4-methyl-piperazine-1-carbonyl, a piperidine-1-carbonyl and a 4-dimethylaminopiperidine-1-carbonyl.

More preferably, the compounds represented by general formula I have the following structures:

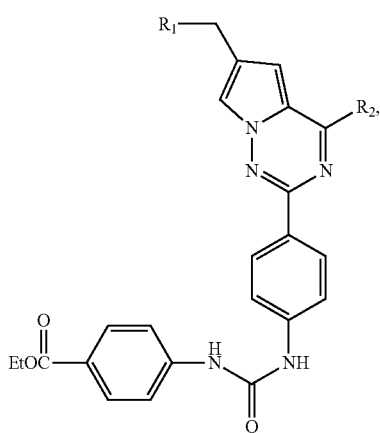

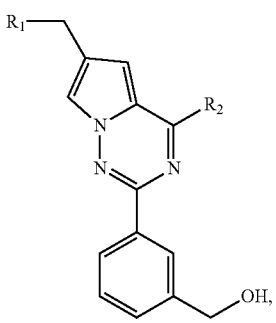

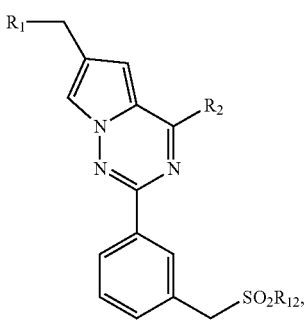

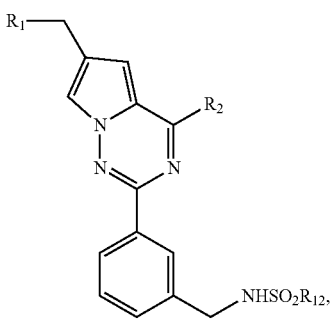

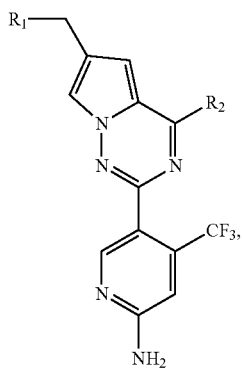

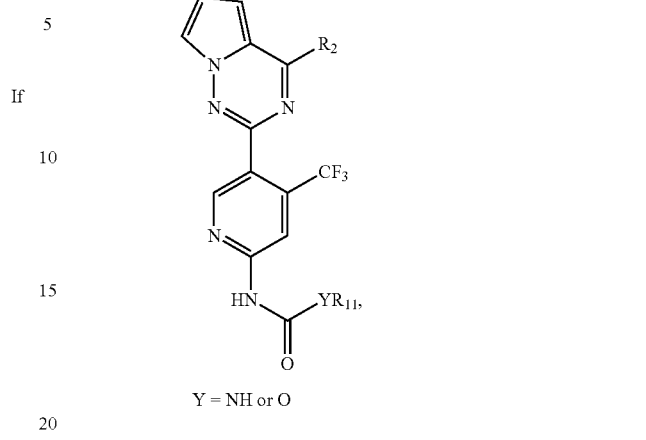

Y = NH or O wherein $R_1$, $R_2$, $R_{11}$ and $R_{12}$ are defined as above, $R_{16}$ and $R_{17}$ are identical or different, and each independently selected from C1-C4 alkyl, or $R_{16}$ and $R_{17}$ are combined with the nitrogen atom to which they are attached to form a 4-methyl-piperazinyl, a 4-dimethylamino-piperidyl or piperidin-1-yl.

Most preferably, the present invention provides the compounds as shown in table 1.

TABLE 1

The structures of representative compounds of general formula I

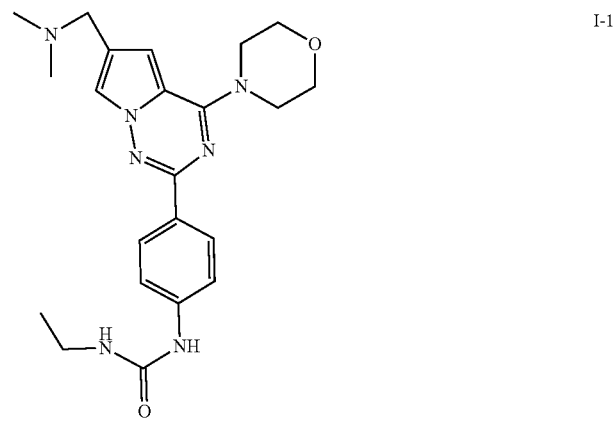

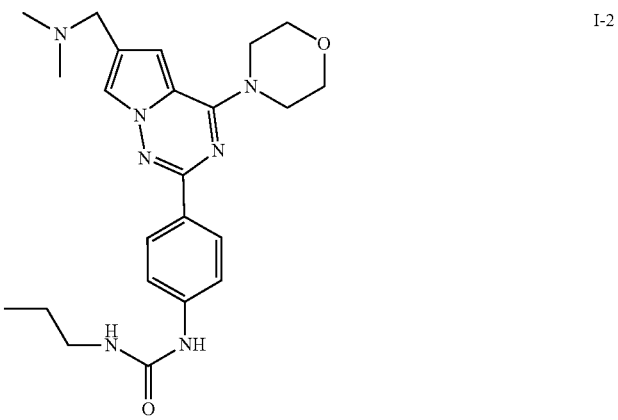

TABLE 1-continued
The structures of representative compounds of general formula I
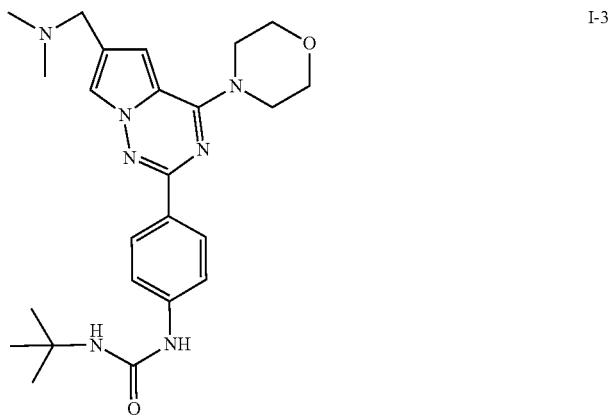
I-3
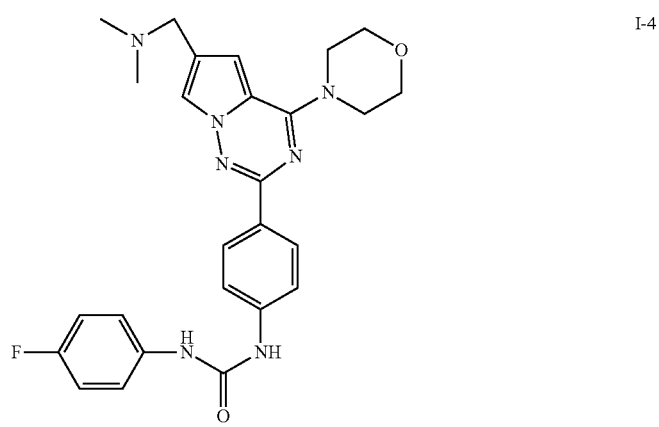
I-4
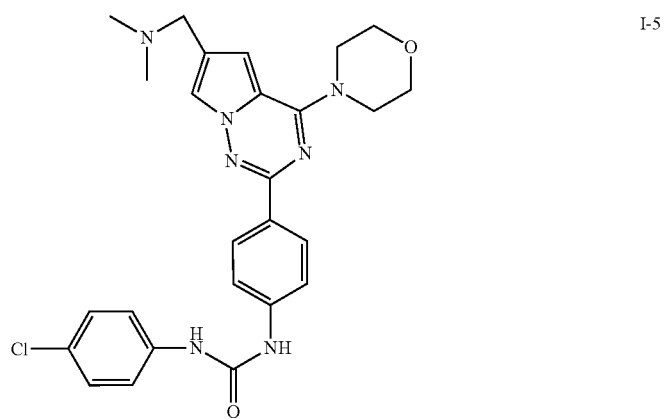
I-5

TABLE 1-continued
The structures of representative compounds of general formula I
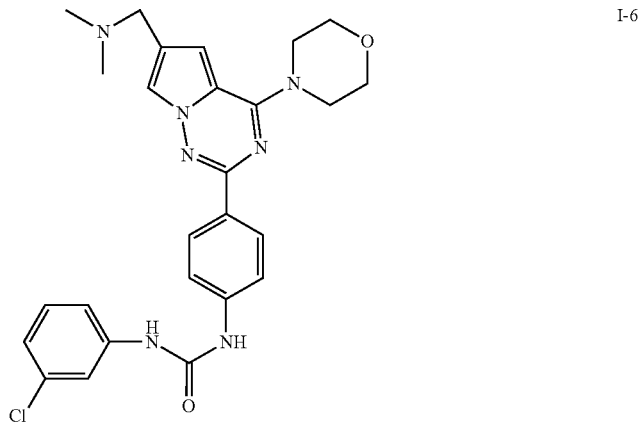
I-6
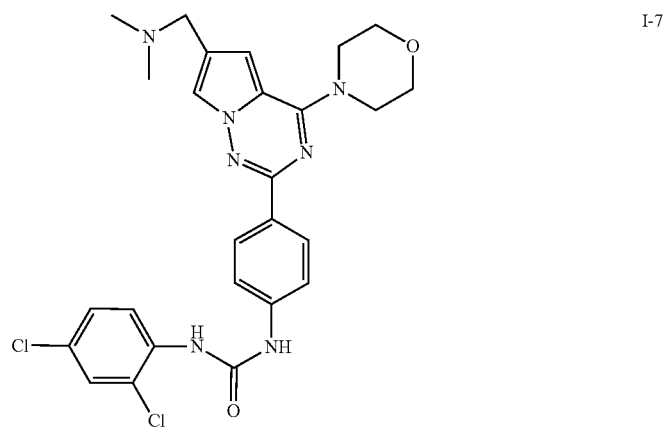
I-7
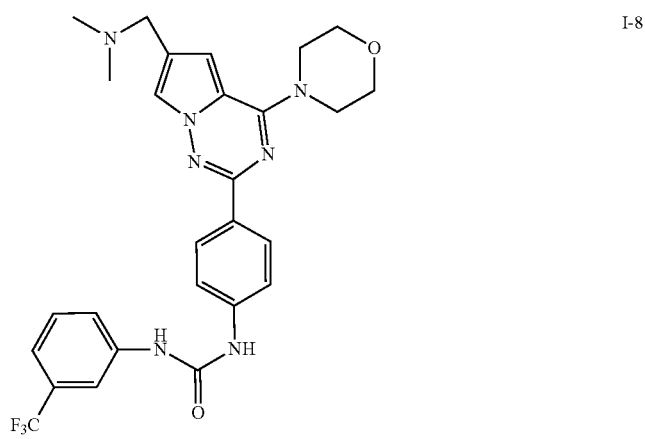
I-8

TABLE 1-continued
The structures of representative compounds of general formula I
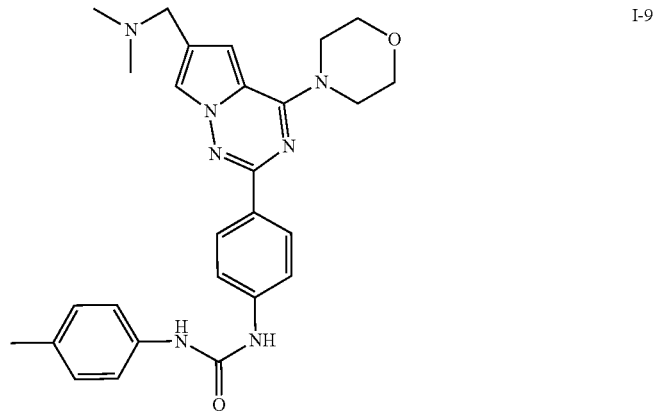
I-9
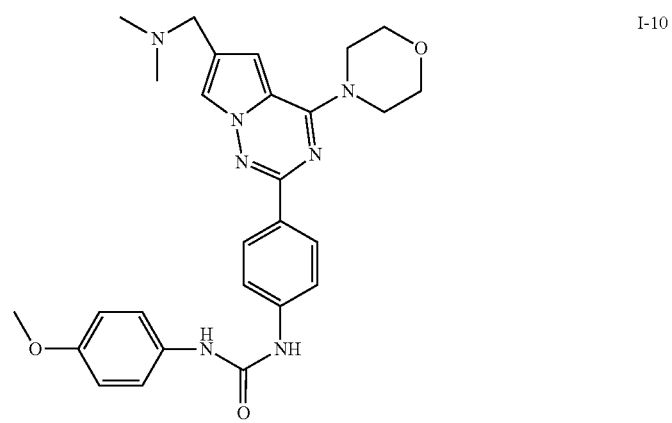
I-10
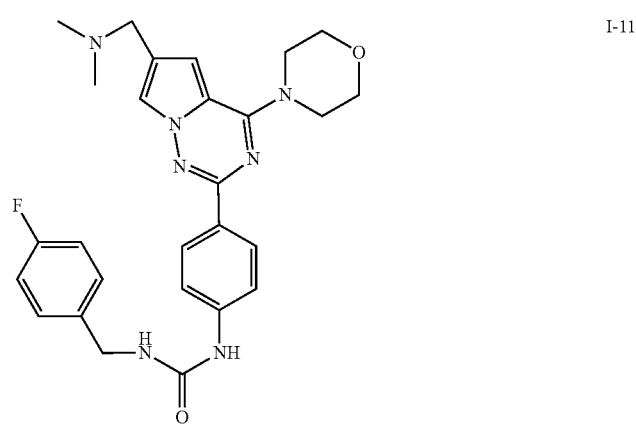
I-11

TABLE 1-continued
The structures of representative compounds of general formula I
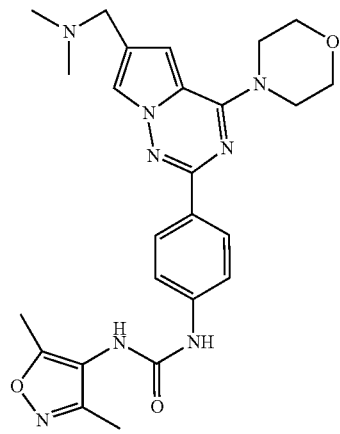
I-12
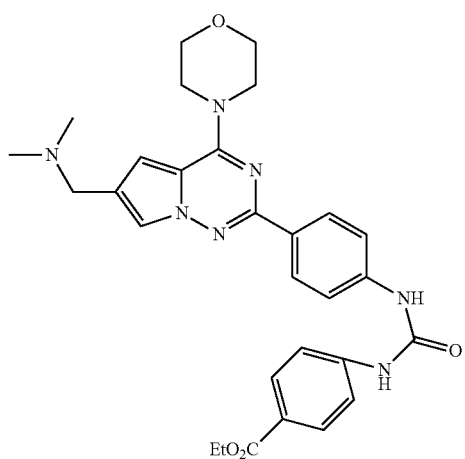 [SMILES: CCOC(=O)c1ccc(NC(=O)Nc2ccc(-c3nc(N4CCOCC4)c4cc(CN(C)C)cn4n3)cc2)cc1]
I-13
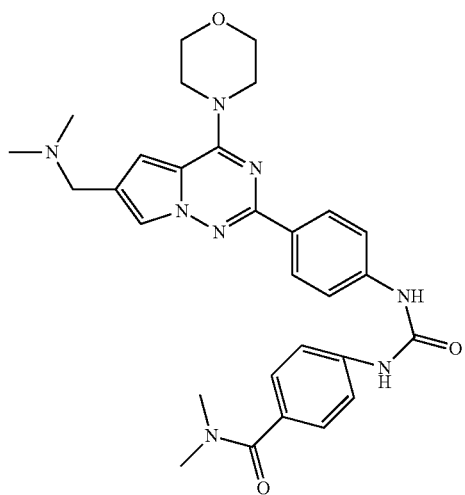 [SMILES: CN(C)Cc1cc2c(N3CCOCC3)nc(-c3ccc(NC(=O)Nc4ccc(C(=O)N(C)C)cc4)cc3)nn2c1]
I-14

TABLE 1-continued
The structures of representative compounds of general formula I
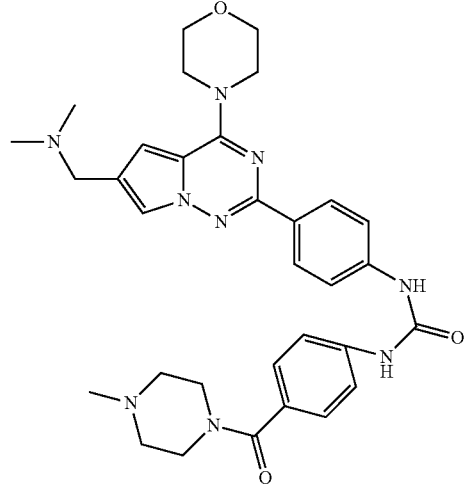
I-15
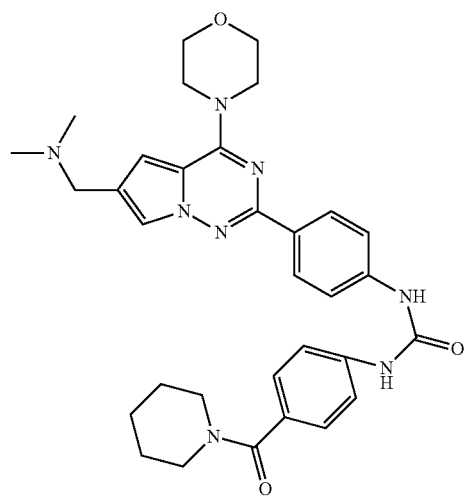 [SMILES: CN(C)Cc1cc2c(N3CCOCC3)nc(-c3ccc(NC(=O)Nc4ccc(C(=O)N5CCCCC5)cc4)cc3)nn2c1]
I-16
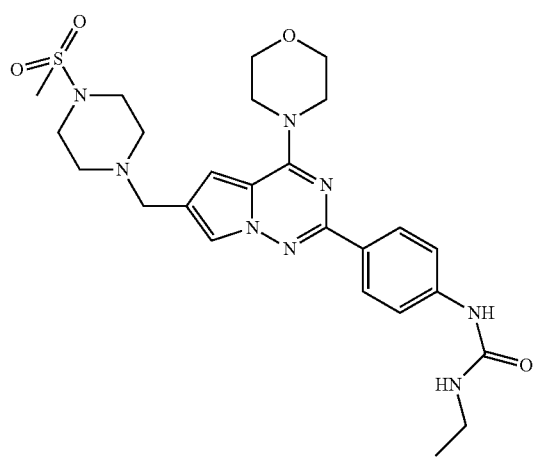 [SMILES: CCNC(=O)Nc1ccc(-c2nc(N3CCOCC3)c3cc(CN4CCN(S(C)(=O)=O)CC4)cn3n2)cc1]
I-17

TABLE 1-continued
The structures of representative compounds of general formula I
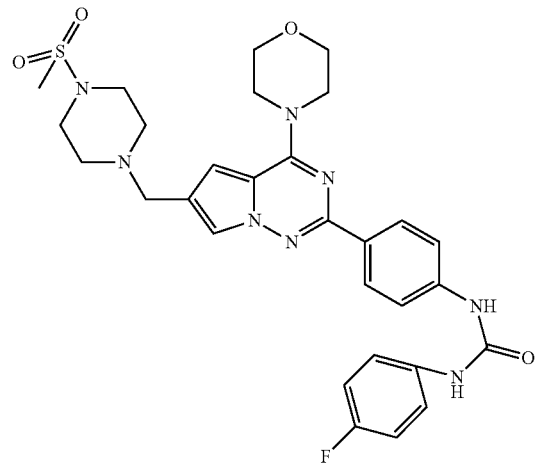
I-18
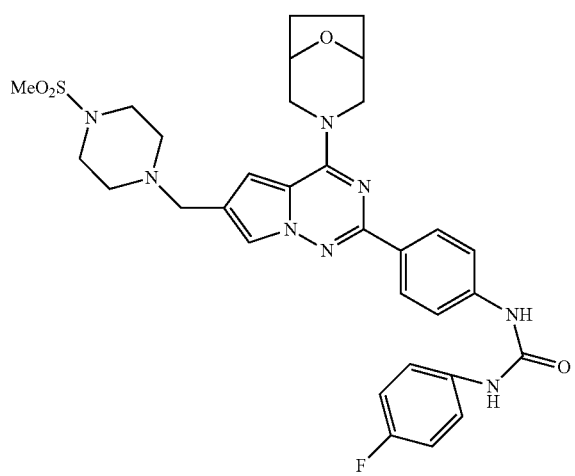 [SMILES: CS(=O)(=O)N1CCN(Cc2cc3c(N4CC5CCC(C4)O5)nc(-c4ccc(NC(=O)Nc5ccc(F)cc5)cc4)nn3c2)CC1]
I-19
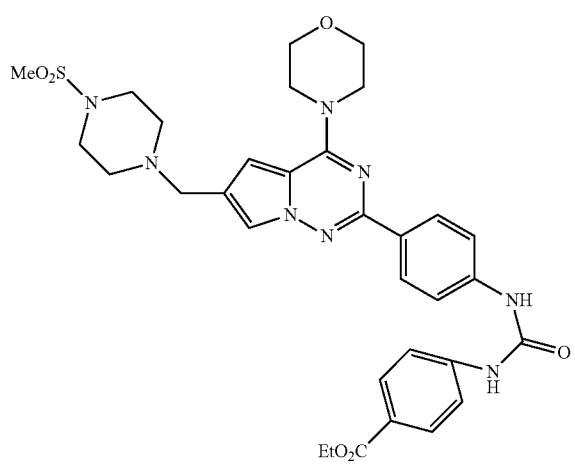 [SMILES: CCOC(=O)c1ccc(NC(=O)Nc2ccc(-c3nc(N4CCOCC4)c4cc(CN5CCN(S(C)(=O)=O)CC5)cn4n3)cc2)cc1]
I-20

TABLE 1-continued
The structures of representative compounds of general formula I
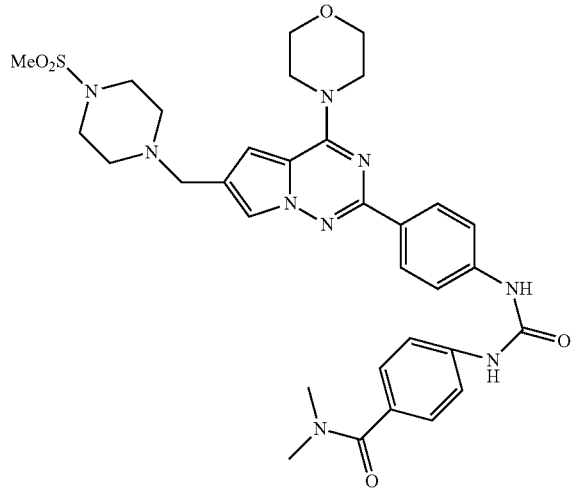
I-21
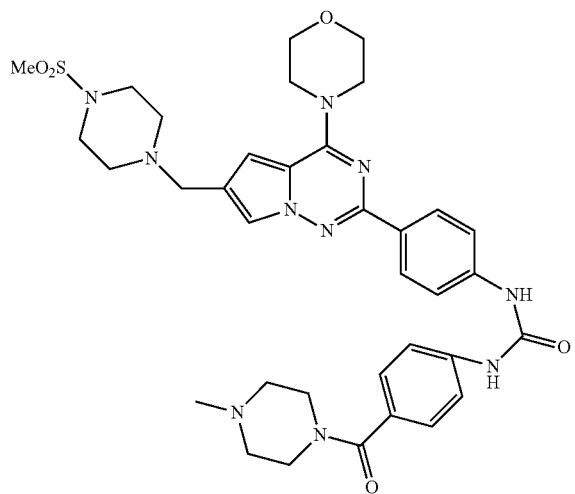 [SMILES: CN1CCN(C(=O)c2ccc(NC(=O)Nc3ccc(-c4nc(N5CCOCC5)c5cc(CN6CCN(S(C)(=O)=O)CC6)cn5n4)cc3)cc2)CC1]
I-22
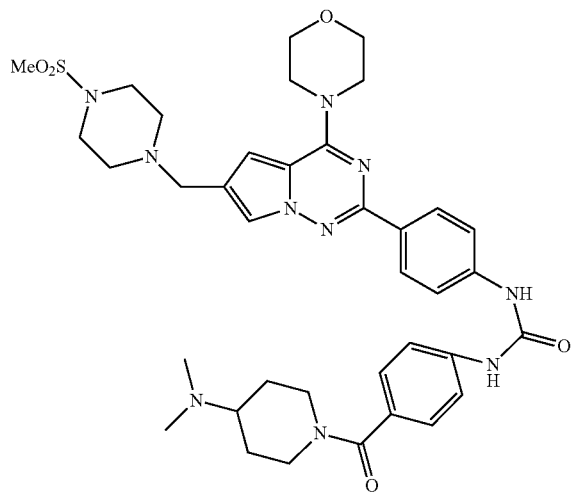 [SMILES: CN(C)C1CCN(C(=O)c2ccc(NC(=O)Nc3ccc(-c4nc(N5CCOCC5)c5cc(CN6CCN(S(C)(=O)=O)CC6)cn5n4)cc3)cc2)CC1]
I-23

TABLE 1-continued
The structures of representative compounds of general formula I
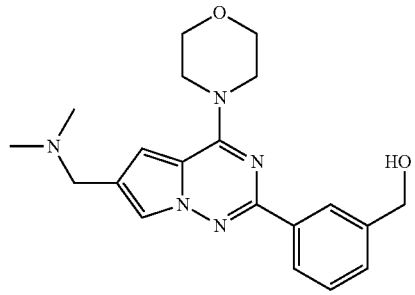
I-24
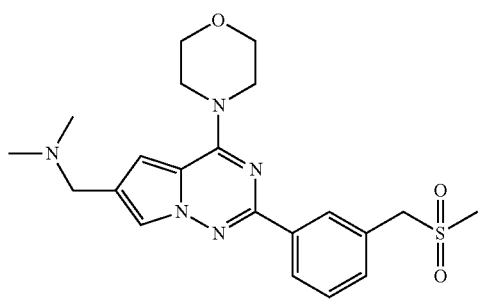
I-25
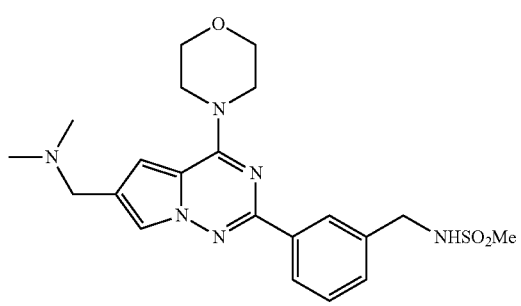
I-26
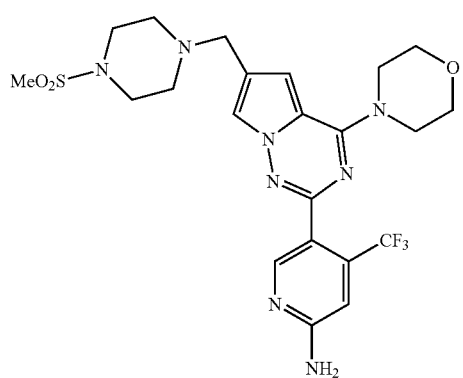 [SMILES: CS(=O)(=O)N1CCN(Cc2cc3c(N4CCOCC4)nc(-c4cnc(N)cc4C(F)(F)F)nn3c2)CC1]
I-27

TABLE 1-continued
The structures of representative compounds of general formula I
I-28
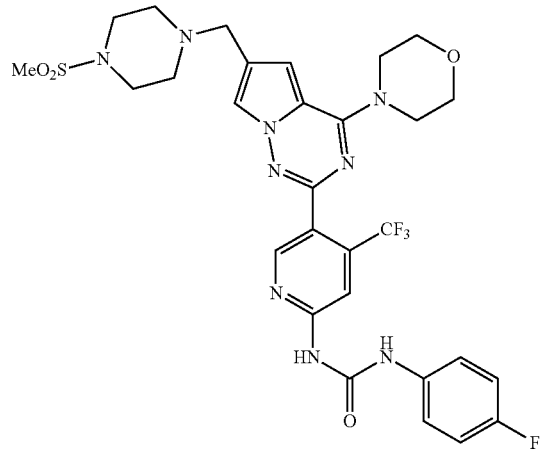 [SMILES: CS(=O)(=O)N1CCN(Cc2cc3c(N4CCOCC4)nc(-c4cnc(NC(=O)Nc5ccc(F)cc5)cc4C(F)(F)F)nn3c2)CC1]
I-29
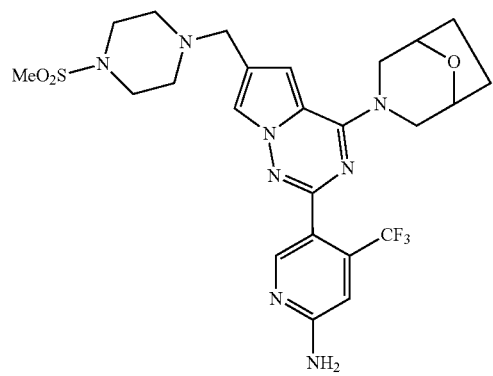 [SMILES: CS(=O)(=O)N1CCN(Cc2cc3c(N4CC5CCC(C4)O5)nc(-c4cnc(N)cc4C(F)(F)F)nn3c2)CC1]
I-30
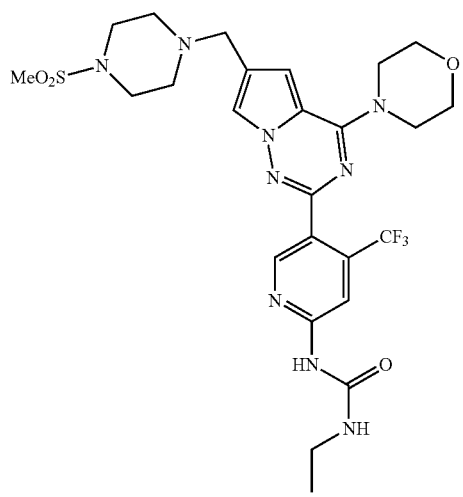 [SMILES: CCNC(=O)Nc1cc(C(F)(F)F)c(-c2nc(N3CCOCC3)c3cc(CN4CCN(S(C)(=O)=O)CC4)cn3n2)cn1]

TABLE 1-continued
The structures of representative compounds of general formula I
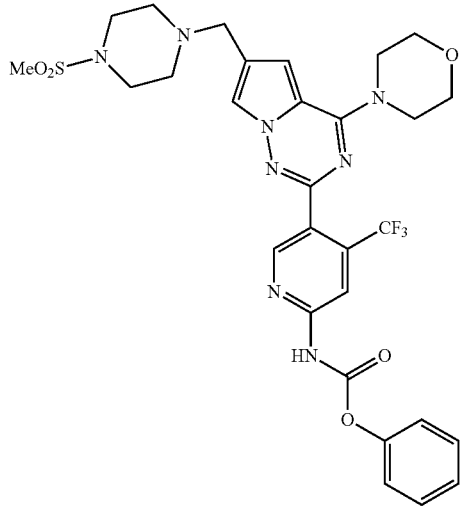
I-31
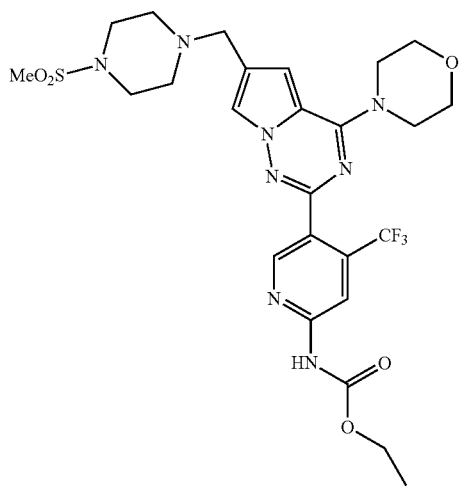 [SMILES: CCOC(=O)Nc1cc(C(F)(F)F)c(-c2nc(N3CCOCC3)c3cc(CN4CCN(S(C)(=O)=O)CC4)cn3n2)cn1]
I-32
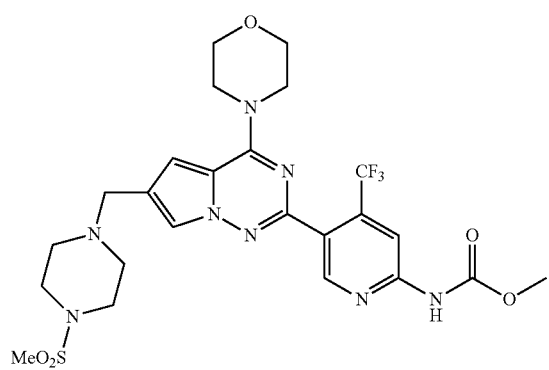 [SMILES: COC(=O)Nc1cc(C(F)(F)F)c(-c2nc(N3CCOCC3)c3cc(CN4CCN(S(C)(=O)=O)CC4)cn3n2)cn1]
I-33

TABLE 1-continued
The structures of representative compounds of general formula I
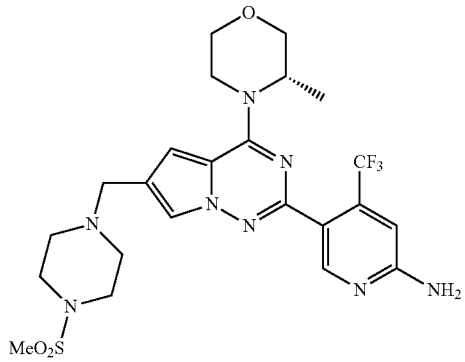
I-34
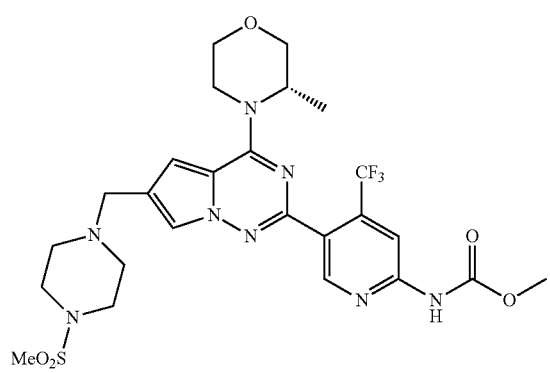 [SMILES: COC(=O)Nc1cc(C(F)(F)F)c(-c2nc(N3CCOC[C@@H]3C)c3cc(CN4CCN(S(C)(=O)=O)CC4)cn3n2)cn1]
I-35
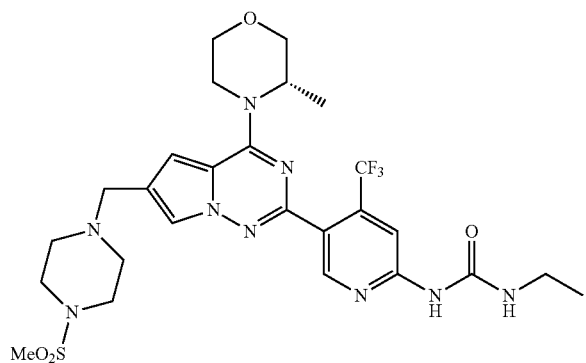 [SMILES: CCNC(=O)Nc1cc(C(F)(F)F)c(-c2nc(N3CCOC[C@@H]3C)c3cc(CN4CCN(S(C)(=O)=O)CC4)cn3n2)cn1]
I-36
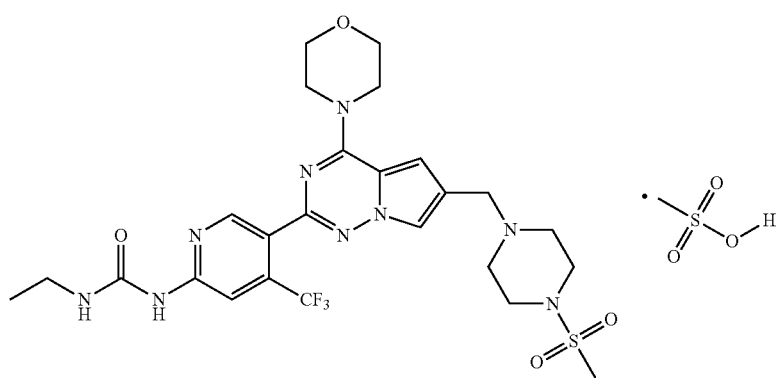

TABLE 1-continued
The structures of representative compounds of general formula I
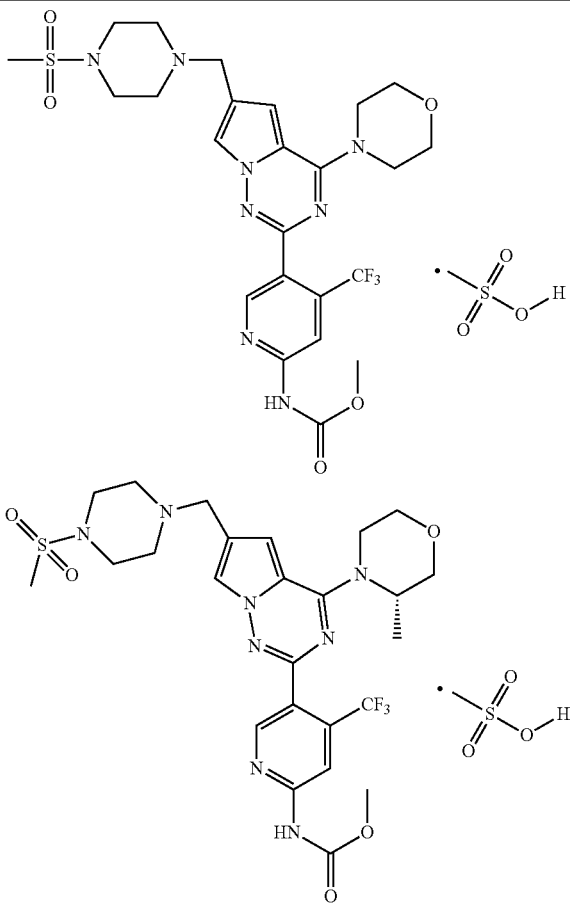
Another object of the present invention is to provide a preparation method for the compounds represented by general formula I, the preparation method comprising the following steps:
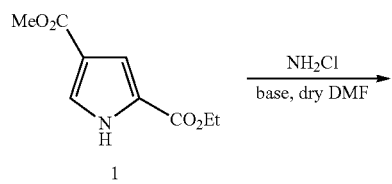
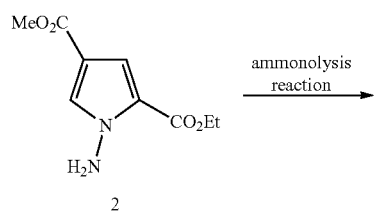
-continued
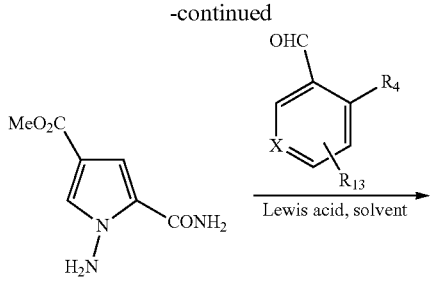
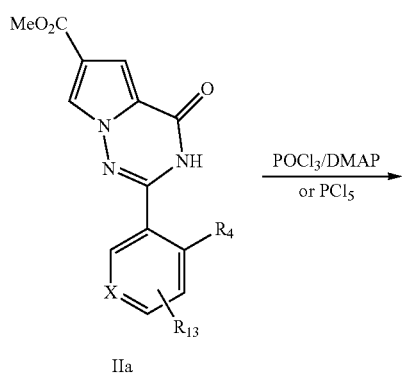

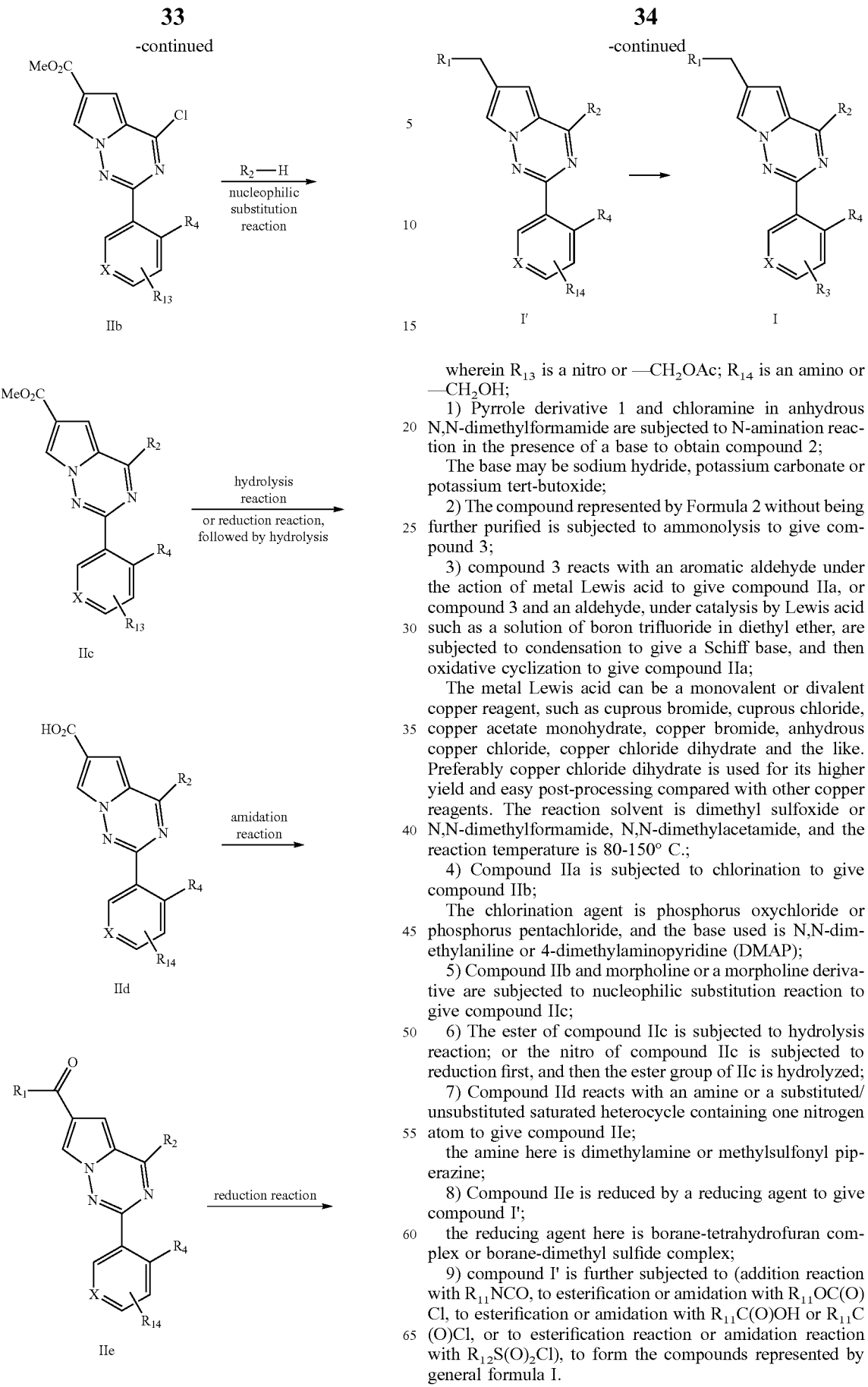

wherein $R_{13}$ is a nitro or —$CH_2OAc$; $R_{14}$ is an amino or —$CH_2OH$;

1) Pyrrole derivative 1 and chloramine in anhydrous N,N-dimethylformamide are subjected to N-amination reaction in the presence of a base to obtain compound 2;

The base may be sodium hydride, potassium carbonate or potassium tert-butoxide;

2) The compound represented by Formula 2 without being further purified is subjected to ammonolysis to give compound 3;

3) compound 3 reacts with an aromatic aldehyde under the action of metal Lewis acid to give compound IIa, or compound 3 and an aldehyde, under catalysis by Lewis acid such as a solution of boron trifluoride in diethyl ether, are subjected to condensation to give a Schiff base, and then oxidative cyclization to give compound IIa;

The metal Lewis acid can be a monovalent or divalent copper reagent, such as cuprous bromide, cuprous chloride, copper acetate monohydrate, copper bromide, anhydrous copper chloride, copper chloride dihydrate and the like. Preferably copper chloride dihydrate is used for its higher yield and easy post-processing compared with other copper reagents. The reaction solvent is dimethyl sulfoxide or N,N-dimethylformamide, N,N-dimethylacetamide, and the reaction temperature is 80-150° C.;

4) Compound IIa is subjected to chlorination to give compound IIb;

The chlorination agent is phosphorus oxychloride or phosphorus pentachloride, and the base used is N,N-dimethylaniline or 4-dimethylaminopyridine (DMAP);

5) Compound IIb and morpholine or a morpholine derivative are subjected to nucleophilic substitution reaction to give compound IIc;

6) The ester of compound IIc is subjected to hydrolysis reaction; or the nitro of compound IIc is subjected to reduction first, and then the ester group of IIc is hydrolyzed;

7) Compound IId reacts with an amine or a substituted/unsubstituted saturated heterocycle containing one nitrogen atom to give compound IIe;

the amine here is dimethylamine or methylsulfonyl piperazine;

8) Compound IIe is reduced by a reducing agent to give compound I';

the reducing agent here is borane-tetrahydrofuran complex or borane-dimethyl sulfide complex;

9) compound I' is further subjected to (addition reaction with $R_{11}NCO$, to esterification or amidation with $R_{11}OC(O)Cl$, to esterification or amidation with $R_{11}C(O)OH$ or $R_{11}C(O)Cl$, or to esterification reaction or amidation reaction with $R_{12}S(O)_2Cl$), to form the compounds represented by general formula I.

Particularly, the compounds represented by general formula Ia-If can be prepared by the following steps:

(1) Synthesis of the compounds represented by general formula IIIa-IIIc and synthesis of N-(5-formyl-4-(trifluoromethyl)pyridin-2-yl)pivalamide (7):

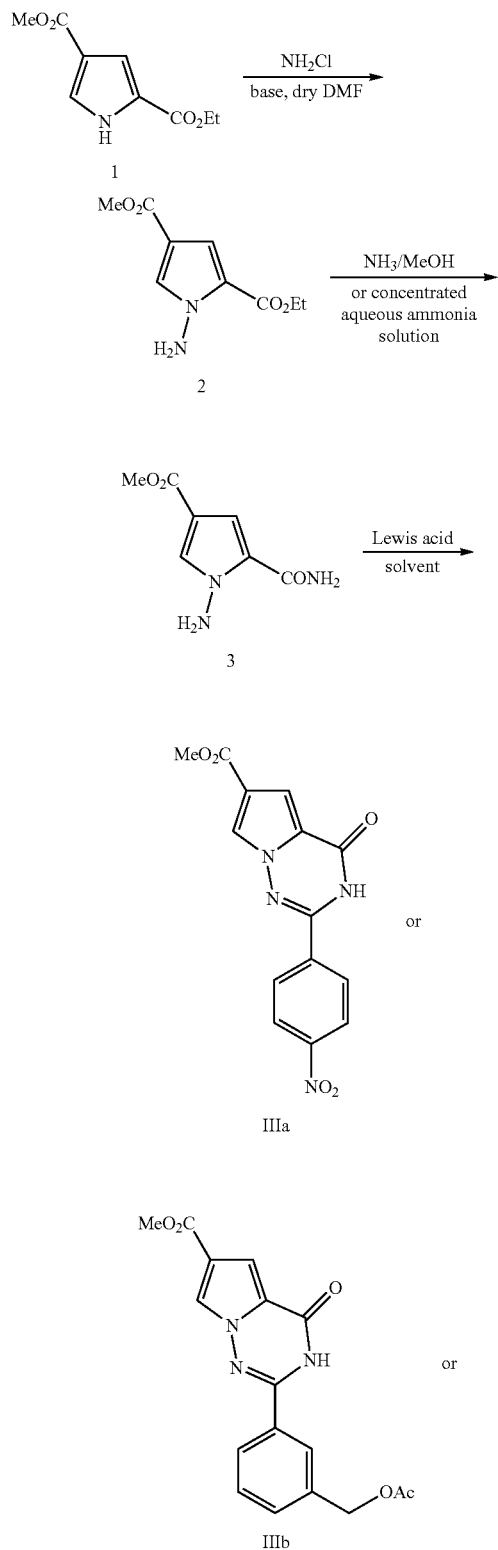

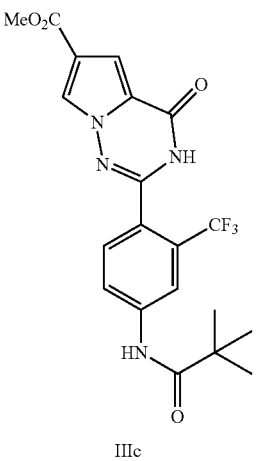

pyrrole derivative 1 and chloramine in dry N,N-dimethylformamide are subjected to N-amination reaction in the presence of a base to obtain compound 2, wherein the base may be sodium hydride, potassium carbonate or potassium tert-butoxide. Without further being purified, the crude product 2 is directly ammonolyzed in a sealed tube by using saturated solution of ammonia in methanol or commercially available concentrated aqueous ammonia solution to give compound 3. Compound 3 reacts with the corresponding aromatic aldehyde (eg. p-nitrobenzaldehyde, 3-formyl-benzyl acetate, N-(5-formyl-4-(trifluoromethyl)pyridin-2-yl)pivalamide) in the presence of a suitable metal Lewis acid to give compounds IIIa, IIIb, or IIIc. compounds IIIa, IIIb, or IIIc are also obtained by the condensation of compound 3 and various aldehydes in the presence of Lewis acid such as boron trifluoride solution in diethyl ether to give a Schiff base, and followed by oxidative cylclization. Wherein the metal Lewis acid can be a monovalent or divalent copper reagent, such as cuprous bromide, cuprous chloride, copper acetate monohydrate, copper bromide, anhydrous copper chloride, copper chloride dihydrate and the like. Compared with other copper reagent, higher yields can be obtained by using copper chloride dihydrate, and post-processing is easier. The reaction solvent is dimethyl sulfoxide or N,N-dimethylformamide, N,N-dimethylacetamide, and the reaction temperature is 80-150° C.

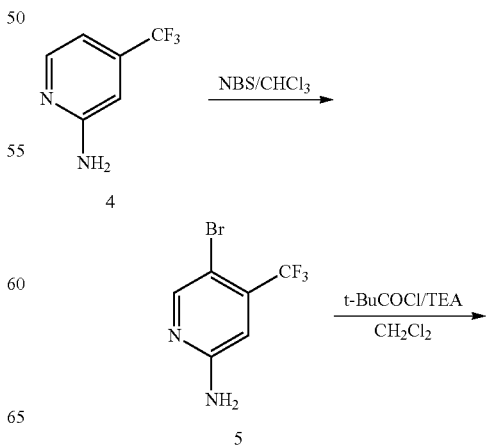

-continued

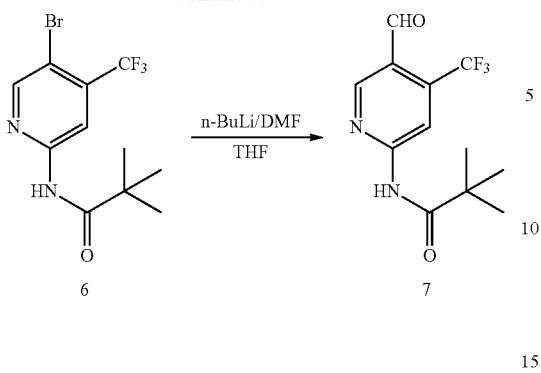

Wherein, aldehyde 7 is obtained by a three-step procedure. 2-amino-4-trifluoromethylpyridine (4) is brominated by N-bromosuccinimide in chloroform to give compound 5. The amino group of compound 5 is protected with a pivaloyl group, and then compound 7 is obtained using n-butyl lithium and N,N-dimethylformamide in anhydrous tetrahydrofuran.

(2) synthesis of pyrrolo[2,1-f][1,2,4]triazine derivatives Ia and Ib wherein X=CH and $R_3$ is NHC(O)NHR$_{11}$:

Compound IIIa is chlorinated by phosphorus oxychloride or phosphorus pentachloride to give product 8, which reacts with morpholine or its analogue at room temperature in tetrahydrofuran to obtain compound 9. Compound 9 is reduced by 5% or 10% palladium on carbon to give compound 10, the ester group of which is hydrolyzed under a basic condition to give acid 11. Compound 11 and an amine, such as dimethylamine or methylsulfonyl piperazine, etc., are subjected to a condensation to give compound 12. Then 12 is reduced by a reducing agent to give compound 13, wherein the reducing agent can be borane-tetrahydrofuran complex or borane-dimethyl sulfide complex. The reductive product 13 reacts with a series of isocyanates in anhydrous dichloromethane at room temperature, or with the corresponding acyl azide in dioxane at reflux to give Ia. When $R_{11}$ is 4-ethoxycarbonyl-phenyl, Ia is hydrolyzed to give compound 14. Compound 14 and dimethylamine, N-methylpiperazine or 4-dimethylaminopiperidine are subjected to condensation to give Ib.

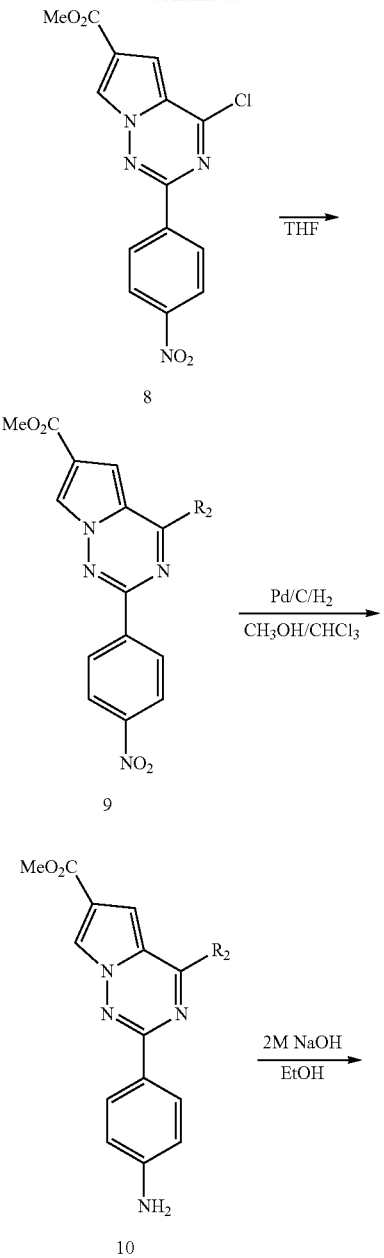

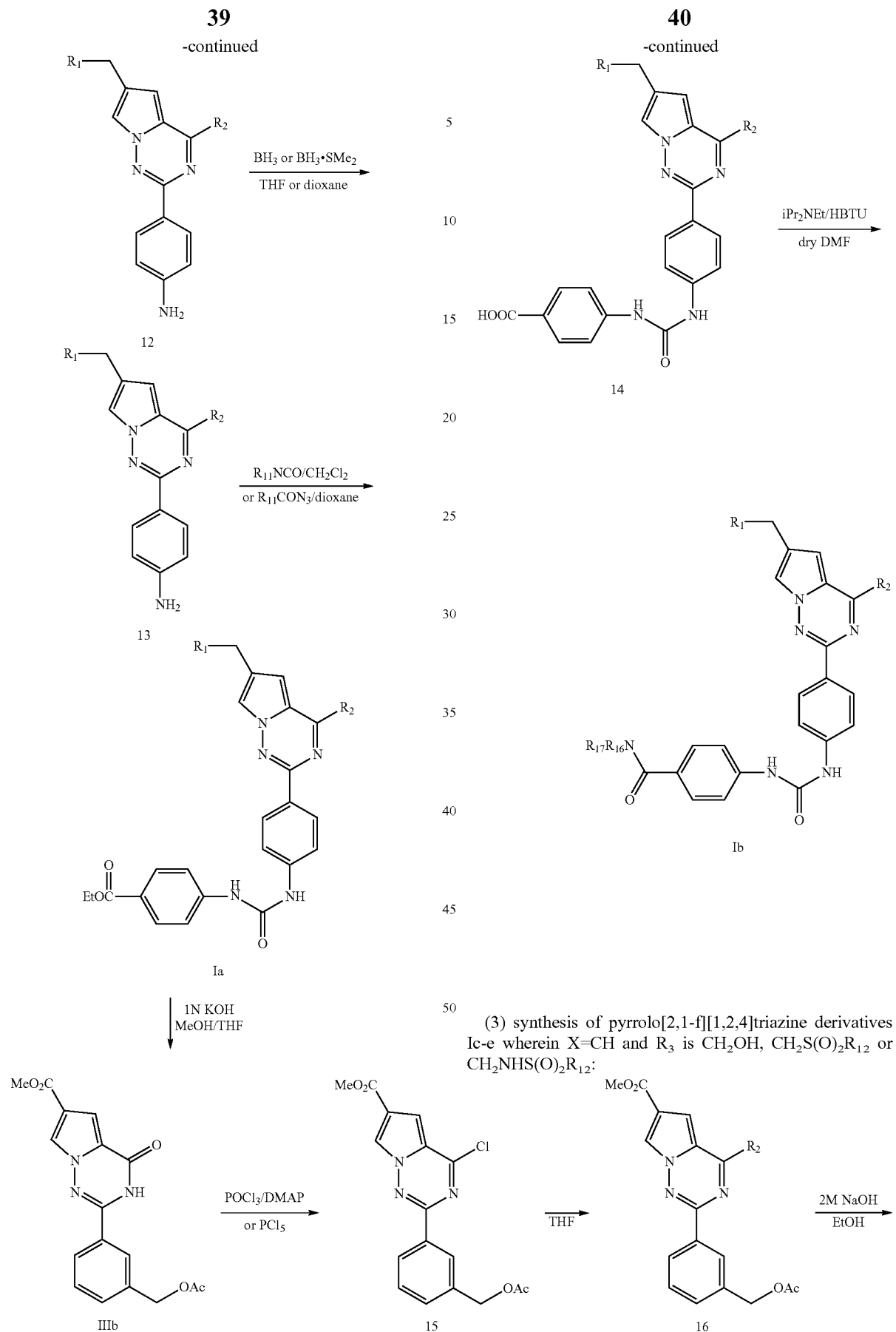
(3) synthesis of pyrrolo[2,1-f][1,2,4]triazine derivatives Ic-e wherein X=CH and $R_3$ is $CH_2OH$, $CH_2S(O)_2R_{12}$ or $CH_2NHS(O)_2R_{12}$:

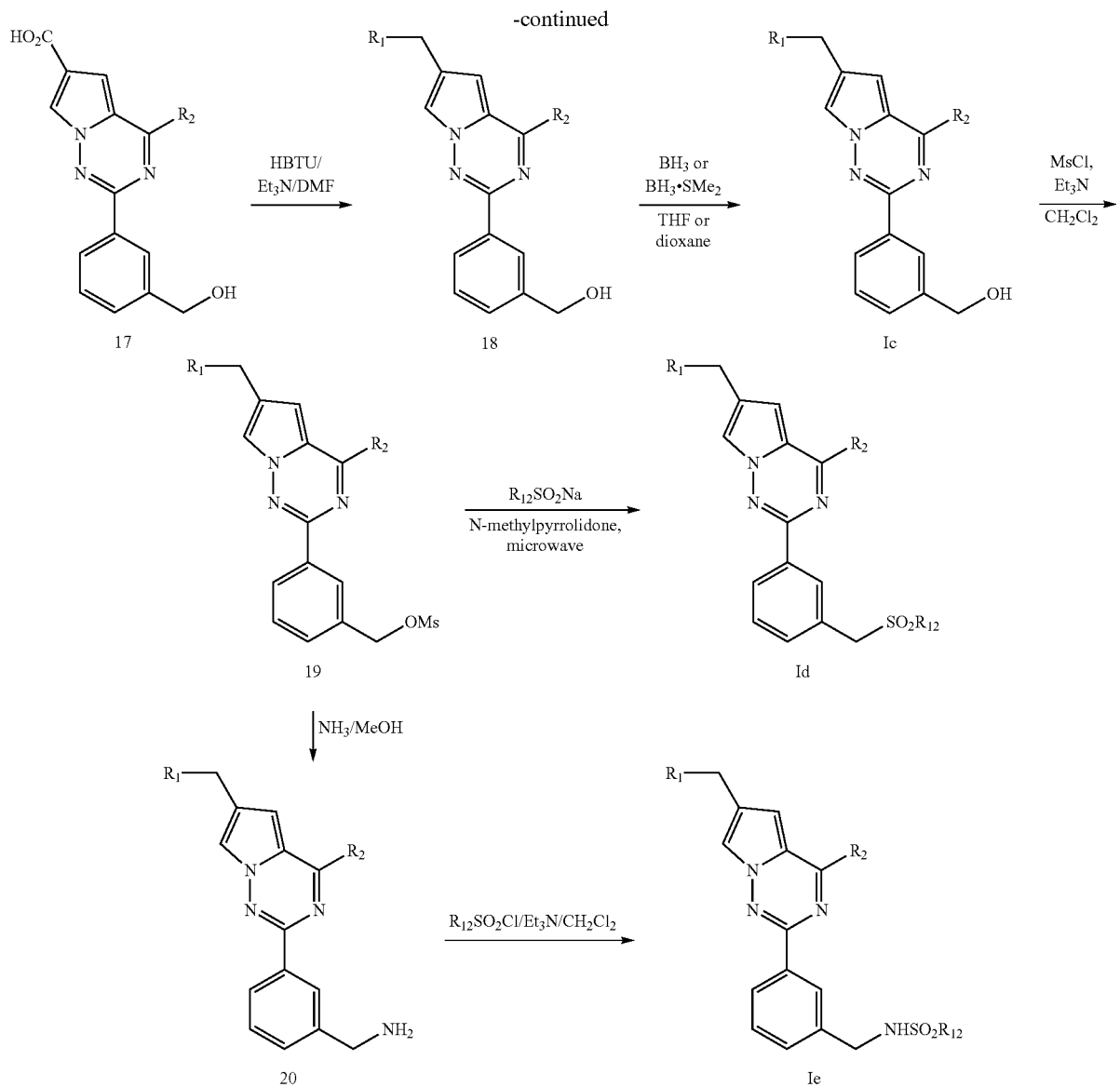

Chlorinated compound IIIb reacts with morpholine or its analogue thereof at room temperature in tetrahydrofuran to obtain compound 16. The ester group of compound 16 is hydrolyzed to give compound 17. 17 and amine, such as dimethylamine or methylsulfonyl piperazine, etc., are subjected to condensation to give compound 18, and then 18 is reduced by a borane-tetrahydrofuran solution or borane-dimethyl sulfide solution to give Ic. With the methylsulfonyl chloride, the hydroxyl of Ic is converted to good leaving group methanesulfonate, and turned to be compound 19. Compound 19 reacts with sodium alkyl sulfonate under microwave irradiation in N-methylpyrrolidone at 120° C. for 30 mins to give compound Id. Furthermore, compound 19 is subjected to ammonolysis to give compound 20, which then reacts with alkyl sulfonyl chloride to give compound Ie.

(4) synthesis of pyrrolo[2,1-f][1,2,4]triazine derivatives If-Ig wherein X=N, $R_3$ is $NH_2$, $NHC(O)NHR_{11}$, or $NHC(O)OR_{11}$, and $R_4$ is $CF_3$:

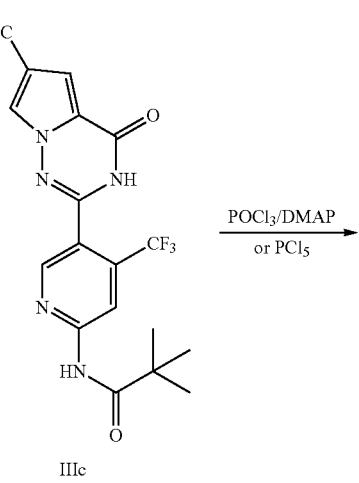

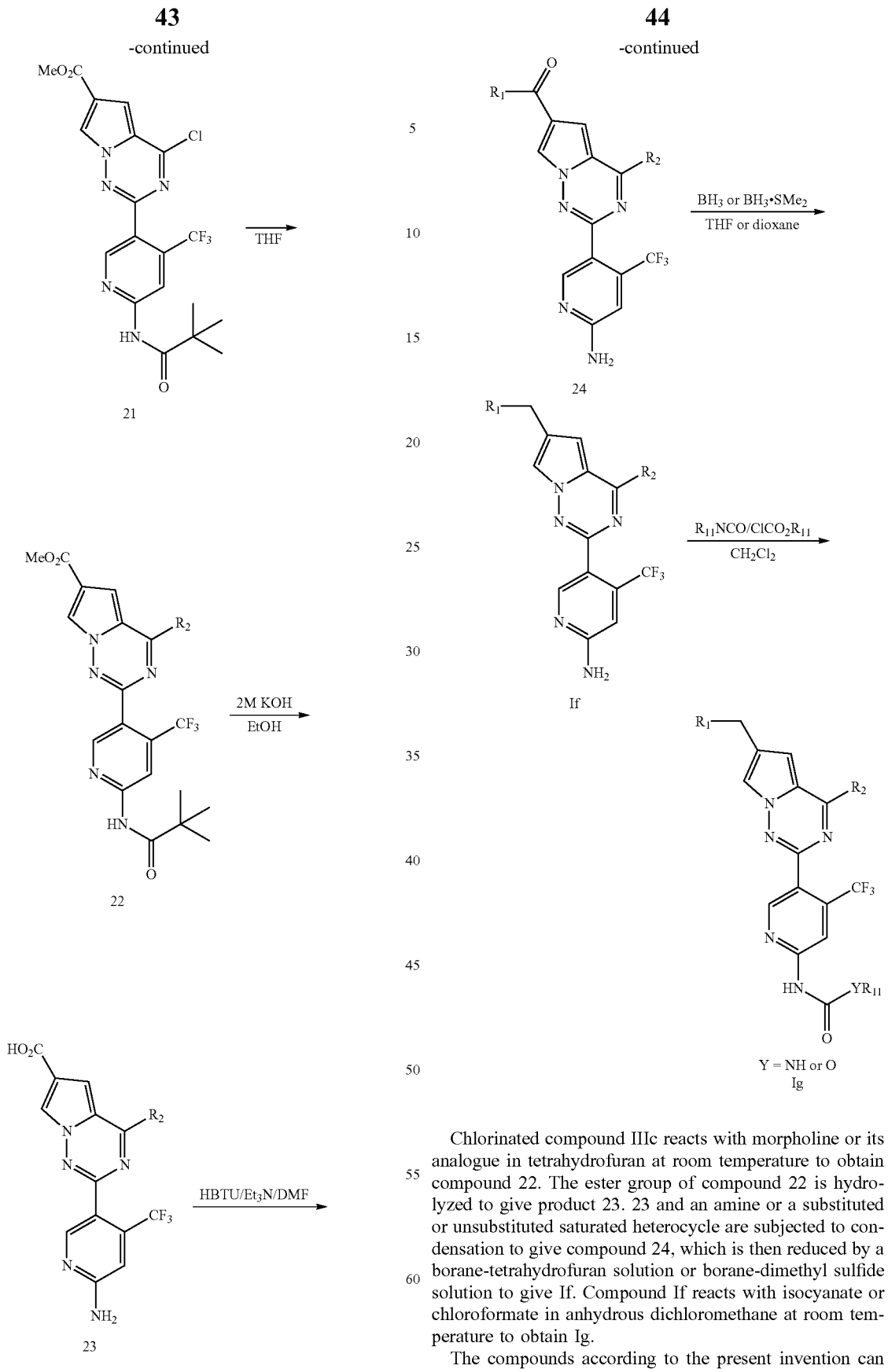

Chlorinated compound IIIc reacts with morpholine or its analogue in tetrahydrofuran at room temperature to obtain compound 22. The ester group of compound 22 is hydrolyzed to give product 23. 23 and an amine or a substituted or unsubstituted saturated heterocycle are subjected to condensation to give compound 24, which is then reduced by a borane-tetrahydrofuran solution or borane-dimethyl sulfide solution to give If. Compound If reacts with isocyanate or chloroformate in anhydrous dichloromethane at room temperature to obtain Ig.

The compounds according to the present invention can efficiently inhibit the activity of PI3K kinase. Therefore, these compounds can be used in the treatment of diseases associated with PI3K pathway, in particular for the treatment of tumors. Therefore, a further object of the present invention is to provide a use of the compounds of general formula I or pharmaceutically acceptable salts thereof for the preparation of phosphatidylinositol 3-kinase and the mammalian target protein of rapamycin inhibitor medicaments, i.e. for the preparation of medicaments for treating phosphatidylinositol 3-kinase-related diseases. The phosphatidylinositol 3-kinase-related diseases include tumors. The tumors include human rhabdomyosarcoma, non-small cell lung cancer, human glioma, prostate cancer, ovarian cancer, liver cancer, colon cancer, breast cancer and so on.

Moreover, the present invention provides a pharmaceutical composition comprising a therapeutically effective amount of the compound of general formula I, and the pharmaceutical composition may also include other ingredients, such as carrier, excipient, and the like.

The present invention provides a method for treating phosphatidylinositol 3-kinase-related diseases, which comprises administering a therapeutically effective amount of the compound represented by general formula I.

DETAILED DESCRIPTION

Figure 1:
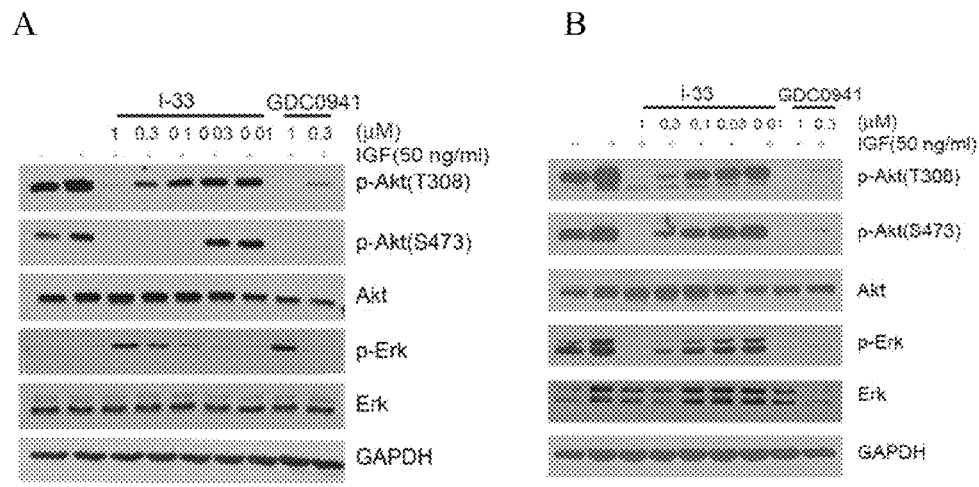
FIG. 1 shows the effects of I-33 on the PI3K signal pathway of human rhabdomyosarcoma Rh30 cells and human glioma U87MG cells.

The present invention will be further illustrated by the following examples, but these examples do not limit the invention in any way. In all examples, $^1$H NMR was recorded with Brucher AM-400 or GEMINI-300 nuclear magnetic resonance spectrometers, wherein the chemical shift is represented by δ (ppm). Mass spectrum was recorded with MAT-95 mass spectrometer. The 200-300 mesh of silica gels were used for separation.

EXAMPLES

1. Preparation of methyl 1-amino-5-carbamoyl-1H-pyrrole-3-carboxylate (3)

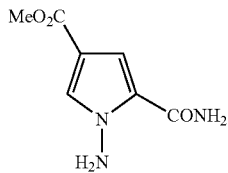 [SMILES: COC(=O)c1cc(C(N)=O)n(N)c1]

The mixture of 9 g ammonium chloride and 330 mL diethyl ether was cooled to −20° C. and 15 mL of concentrated aqueous ammonia solution was added with a dropper. 216 mL of 5% (mass percentage) of sodium hypochlorite solution was dropped via a constant pressure dropping funnel. The mixture was stirred at −10° C. for 30 minutes. After separation, the organic layer was washed with saturated brine (chloramine is unstable and the brine should be pre-cooled). Anhydrous calcium chloride was added into the organic layer and the mixture was dried at −40° C. for 1 hour before use.

The compound pyrrole-1,3-dicarboxylate 1 (5 g, 25.4 mmol, prepared according to Kamijo, S., Kanazawa, C., and Yamamoto Y. *J. AM. CHEM. SOC.* 2005, 127, 9260-9266, wherein the starting materials methyl propiolate and ethyl isocyanoacetate were purchased from Darui chemical Co., Ltd) was dissolved in 25 mL of anhydrous N,N-dimethylformamide, and cooled in an ice bath to 0° C. Sodium hydride (60%, dispensed in mineral oil, 1.22 g, 30.5 mmol) was added in batches. The mixture was stirred for 1 hour at room temperature. Then 300 mL of chloramine solution in diethyl ether prepared in advance was added in one portion and stirred overnight at room temperature under nitrogen atmosphere. The reaction mixture was quenched with saturated sodium thiosulfate solution and diluted with water. The diethyl ether layer was separated and the aqueous layer was extracted once with ethyl acetate. The organic layers were combined and washed with water for three times, dried over anhydrous sodium sulfate, and concentrated under reduced pressure to give 6.2 g of crude product which is directly subjected to ammonolysis without purification. To each 3 g of crude product was added 80 mL of saturated solution of ammonia in methanol and the reaction was carried out at 80° C. in a sealed tube for 2 days. The reaction mixture was concentrated to precipitate solid, then allowed to settle for about 1 hour, and filtered to obtain 3 g product as white solid. The yield of two steps was 64.6%. m.p. 222-224° C. $^1$H NMR (300 MHz, DMSO-$d_6$): δ 7.95 (br s, 1H), 7.38 (s, 1H), 7.33 (br s, 1H), 7.15 (s, 1H), 6.87 (s, 2H), 3.70 (s, 3H). MS (EI) m/z (%): 183 (M$^+$, 100).

2. Preparation of 2-amino-4-trifluoromethyl-5-bromopyridine (5)

2-amino-4-trifluoromethylpyridine (5 g, 30.8 mmol, Langfang Beixin Chemical Co., Hebei) was dissolved in 100 mL of chloroform and N-bromosuccinimide (5.92 g, 33.3 mmol) was added in batches. The mixture was stirred in darkness or away from light at room temperature for 3 hours. The reaction mixture was concentrated and purified by column chromatography with gradient elution (petroleum ether: ethyl acetate=10:1 and dichloromethane), so as to give 4.33 g of red solid. Yield: 58.2%. LC-MS: 240 (M+1), 242 (M+2+1).

3. Preparation of N-(5-bromo-4-(trifluoromethyl) pyridin-2-yl) pivalamide (6)

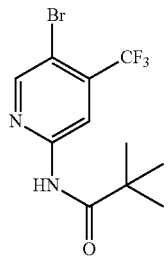 [SMILES: CC(C)(C)C(=O)Nc1cc(C(F)(F)F)c(Br)cn1]

In an ice bath, 29.8 g of pivaloyl chloride (226 mmol) was added dropwise to a solution of compound 5 (50.0 g, 207 mmol) and triethylamine (37.9 mL) in dichloromethane (300.0 mL) within one hour and then stirred for 2 hours until the starting materials disappeared. 150 mL of water was added into the reaction solution and stirred at room temperature for 10 minutes. The organic layer was separated, dried over anhydrous sodium sulfate, concentrated, and separated through a short column with ethyl acetate to give white solid (57.7 g, 85.6%).

m.p. 126-128° C. $^1$H NMR (300 MHz, CDCl$_3$): δ 8.67 (s, 1H), 8.50 (s, 1H), 8.14 (brs, 1H), 1.33 (s, 9H).

4. Preparation of N-(5-formyl-4-(trifluoromethyl)pyridin-2-yl) pivalamide (7)

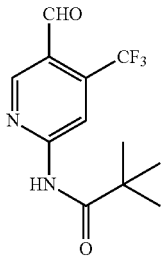

Compound 6 (15.0 g, 46.2 mmol) was dissolved in 350 mL of anhydrous tetrahydrofuran and cooled to −78° C. under nitrogen. 45 mL of 2.5 M n-butyl lithium solution in tetrahydrofuran was slowly added to the reaction solution within one hour. The reaction solution was stirred at −78° C. for 1 hour, and then 15 mL of anhydrous N,N-dimethylformamide was slowly added dropwise and stirred for another 2.5 h at −78° C. To the reaction solution was added 120 mL of 1 M diluted hydrochloric acid to quench the reaction. The reaction mixture was extracted with ethyl acetate (200 mL×3). The organic layers were combined and washed with water (200 mL×3), saturated brine (200 mL) respectively, then dried over anhydrous sodium sulfate and filtered. The filtrate was concentrated and purified by column chromatography (petroleum ether: dichloromethane:ethyl acetate=60:10:1) to give 7.1 g of white solid (56.1%). m.p. 96-98° C. $^1$H NMR (300 MHz, CDCl$_3$): δ 10.32 (br s, 1 H), 9.01 (s, 1 H), 8.73 (s, 1 H), 8.40 (s, 1 H), 1.38 (s, 9 H).

5. General Preparation Method for Compounds IIIa-IIIc 5 mL of dimethylsulfoxide was added to a mixture of compound 3 (55 mg, 0.3 mmol), corresponding aldehyde (0.3 mmol) and copper chloride dihydrate (51 mg, 0.3 mmol) and the reaction was performed at 80-150° C. After the reaction was finished, the reaction mixture was cooled and poured into water, the precipitated solids were filtered. If the crude product has poor solubility, it is washed with methanol. If it has good solubility, it is purified through column chromatography (dichloromethane: methanol=50: 1).

Preparation of methyl 2-p-nitrophenyl-4-oxo-3,4-dihydropyrrolo[2,1-f][1,2,4]triazine-6-formate (IIIa)

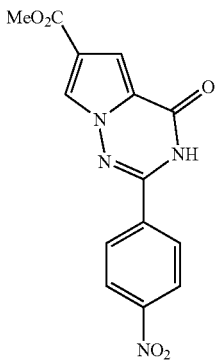 [SMILES: COC(=O)c1cc2c(=O)[nH]c(-c3ccc([N+](=O)[O-])cc3)nn2c1]

According to the general preparation method described in example 5 above, p-nitrobenzaldehyde reacts with compound 3 to give compound IIIa as light yellow solid in 72.0% yield. m.p.>300° C. $^1$H NMR (300 MHz, DMSO-d$_6$): δ 12.52 (s, 1H), 8.38 (d, J=8.5 Hz, 2H), 8.22 (s, 1H), 8.21 (d, J=8.5 Hz, 2H), 7.26 (s, 1H), 3.80 (s, 3H). LRMS (EI) m/z (%): 314 (M$^+$, 85), 283 (100). HRMS calcd. C$_{14}$H$_{10}$N$_4$O$_5$: 314.0651. found: 314.0659.

Preparation of methyl 2-(3-(acetoxylmethyl)phenyl)-4-oxo-3,4-dihydropyrrolo[2,1-f][1,2,4]triazine-6-carboxylate (IIIb)

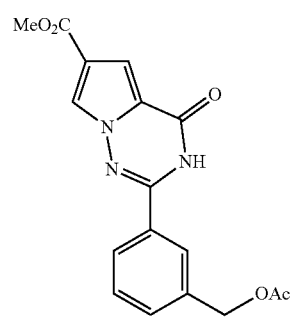 [SMILES: COC(=O)c1cc2c(=O)[nH]c(-c3cccc(COC(C)=O)c3)nn2c1]

According to the general preparation methods described in example 5 above, 3-formylbenzyl acetate reacts with compound 3 to give compound IIIb as offwhite solid in 39.0% yield. m.p. 202-203° C. $^1$H NMR (300 MHz, DMSO-d6): δ 12.29 (s, 1H), 8.19 (d, J=1.7 Hz, 1H), 7.96 (s, 1H), 7.92 (dt, J=1.7, 7.2 Hz, 1H), 7.58-7.53 (m, 2H), 7.24 (d, J=1.7 Hz, 1H), 5.16 (s, 2H), 3.81 (s, 3H), 2.10 (s, 3H). LC-MS: 342 (M+1).

Preparation of methyl 4-oxo-2-(6-pivalamido-4-(trifluoromethyl)-pyridin-3-yl)-3,4-dihydro pyrrolo[2,1-f][1,2,4]triazine-6-carboxylate (IIIc)

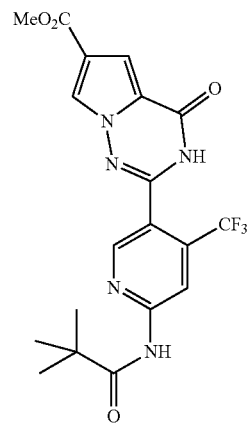 [SMILES: COC(=O)c1cc2c(=O)[nH]c(-c3cnc(NC(=O)C(C)(C)C)cc3C(F)(F)F)nn2c1]

According to the general preparation method described in example 5 above, compound 7 reacts with compound 3 to give compound IIIc as light yellow solid in 25.9% yield. m.p. 244-245° C. $^1$H NMR (300 MHz, DMSO-d$_6$): δ 12.47 (s, 1H), 10.68 (s, 1H), 8.86 (s, 1H), 8.57 (s, 1H), 8.20 (d, J=1.7 Hz, 1H), 7.29 (d, J=1.7 Hz, 1H), 3.81 (s, 3H), 1.28 (s, 9H). LC-MS: 438 (M+1).

6. Preparation of methyl 2-p-nitrophenyl-4-chloro-pyrrolo[2,1-f][1,2,4]triazine-6-carboxylate (8)

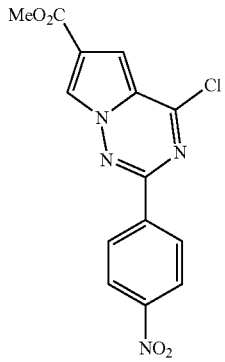 [SMILES: COC(=O)c1cc2c(Cl)nc(-c3ccc([N+](=O)[O-])cc3)nn2c1]

20 mL of phosphorus oxychloride was added to a mixture of compound IIIa (4.74 g, 15.1 mmol) and 4-dimethylamino pyridine (4.34 g, 35.6 mmol) and refluxed for 5 hours. After the reaction mixture was cooled, a portion of phosphorus oxychloride was distilled off under the reduced pressure. The residue was poured into crushed ice, filtered and dried to give yellow solid (4.6 g, 91.8%). m.p. 218-223° C. $^1$H NMR (300 MHz, CDCl$_3$): δ 8.54 (d, J=8.9 Hz, 2H), 8.36 (s, 1H), 8.34 (d, J=8.9 Hz, 2H), 7.46 (d, J=1.3 Hz, 1H), 3.96 (s, 3H). MS (EI) m/z (%): 332 (M$^+$, 100), 334 (M+2, 33).

7. Preparation of Compound 9

Methyl 2-(p-nitrophenyl)-4-(morpholinyl)-pyrrolo[2,1-f][1,2,4]triazine-6-carboxylate (9a)

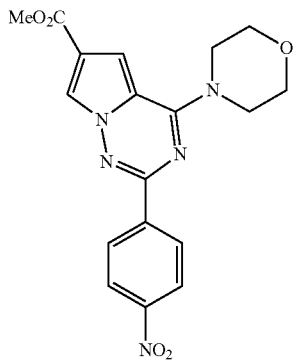 [SMILES: COC(=O)c1cc2c(N3CCOCC3)nc(-c3ccc(N)cc3)nn2c1]

Compound 8 (4.6 g, 13.8 mmol) was suspended in 150 mL of tetrahydrofuran, 3.6 mL of morpholine was added dropwise and reacted for 5 hours at room temperature. 3.9 g of solid was obtained by filteration, and the filtrate was separated through a column chromatography with dichloromethane to give 1.1 g of yellow compound 9a (94.3%). m.p. 296-300° C. $^1$H NMR (300 MHz, CDCl$_3$): δ 8.45 (d, J=8.7 Hz, 2H), 8.29 (d, J=8.7 Hz, 2H), 8.14 (d, J=1.3 Hz, 1H), 7.23 (d, J=1.3 Hz, 1H), 4.17 (t, J=4.8 Hz, 4H), 3.91 (t, J=4.8 Hz, 7H). LC-MS: 384 (M+1).

Methyl 4-(8-oxa-3-azabicylclo[3.2.1]octan-3-yl)-2-(p-nitrophenyl)pyrrolo[2,1-f][1,2,4]triazine-6-carboxylate (9b)

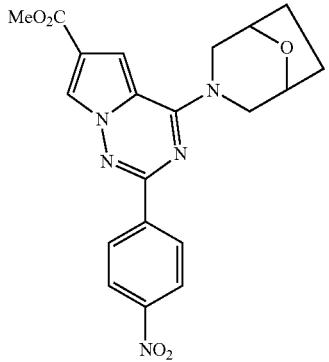 [SMILES: COC(=O)c1cc2c(N3CC4CCC(C3)O4)nc(-c3ccc(N)cc3)nn2c1]

Compound 8 (100 mg, 0.3 mmol) was suspended in 15 mL of tetrahydrofuran, and 8-oxa-3-azabicylclo[3.2.1]octane hydrochloride (54 mg, 0.36 mmol) and one drop of triethylamine were added and reacted for 3-4 h at room temperature. The solvent was removed under the reduced pressure. The residue was washed with water, dried and purified through column chromatography with dichloromethane, so as to give 109 mg of yellow solid 9b (88.6%). m.p. 278-280° C. NMR (300 MHz, CDCl$_3$): δ 8.45 (d, J=9.0 Hz, 2H), 8.29 (d, J=9.0 Hz, 2H), 8.13 (d, J=1.3 Hz, 1H), 7.21 (d, J=1.3 Hz, 1H), 4.60 (br s, 4H), 3.91 (s, 3H), 3.63 (br, s, 2H), 2.08-2.04 (m, 2H), 1.91-1.84 (m, 2H). LC-MS: 410 (M+1).

8. General Preparation Method of Compound 10

A mixed solvent of methanol and chloroform (500 mL, 1:1), and 10 wt % palladium on carbon of starting material (10% Pd-Carbon) were added to compound 9 (13 mmol) and reduced for 24 hours under hydrogen atmosphere at room temperature. Palladium-carbon was filtrated off by celite, and the filtrate was concentrated under reduced pressure to quantitatively obtain Compound 10.

Methyl 2-(p-aminophenyl)-4-(morpholinyl)pyrrolo[2,1-f][1,2,4]triazine-6-carboxylate (10a)

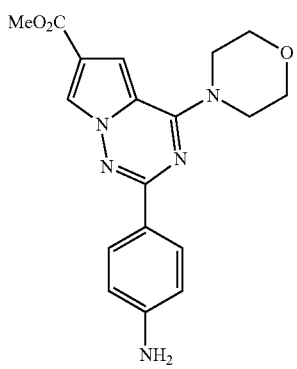

10a was prepared from 9a according to the general preparation method of compound 10. White solid, m.p.

238-240° C. ¹H NMR (300 MHz, DMSO-d₆): δ 8.13 (d, J=1.6 Hz, 1H), 7.93 (d, J=8.5 Hz, 2H), 7.31 (d, J=1.6 Hz, 1H), 6.62 (d, J=8.5 Hz, 2H), 5.70 (br, s, 2H), 4.04 (t, J=4.5 Hz, 4H), 3.80 (s, 3H), 3.77 (t, J=4.5 Hz, 4H). MS (EI) m/e (%): 353 (M⁺, 100).

Methyl 2-(p-aminophenyl)-4-(8-oxa-3-azabicyclo[3.2.1]octan-3-yl)pyrrolo[2,1-f][1,2,4]triazine-6-carboxylate (10b)

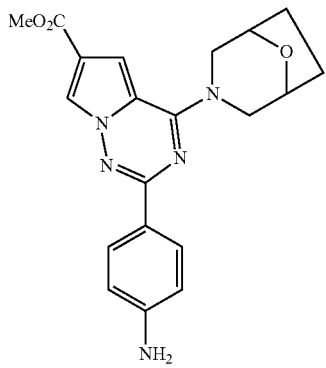

10b was prepared from 9b according to the general preparation method of compound 10. Yellow solid. m.p. 254-256° C. ¹H NMR (300 MHz, DMSO-d₆): δ 8.21 (s, 1H), 8.19 (d, J=8.7 Hz, 2H), 7.34 (s, 1H), 7.22 (d, J=8.7 Hz, 2H), 4.53 (br s, 4H), 3.81 (s, 3H), 3.49 (br, s, 2H), 1.89-1.85 (m, 2H), 1.78-1.75 (m, 2H). LC-MS: 380 (M+1).

9. Preparation Method of Compound 11

2-(p-aminophenyl)-4-(morpholinyl)pyrrolo[2,1-f][1,2,4]triazine-6-carboxylic acid (11a)

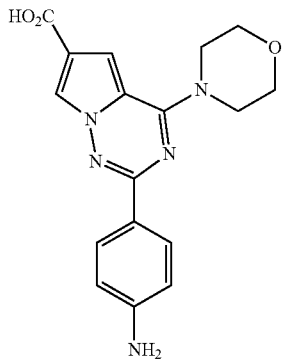 [SMILES: Nc1ccc(-c2nc(N3CCOCC3)c3cc(C(=O)O)cn3n2)cc1]

Compound 10a (14 mmol) was suspended in 150 mL of ethanol, and 30 mL of 2 M aqueous sodium hydroxide solution was added. The reaction mixture was refluxed to be a clear solution and the reaction was substantially completed. 2 mL of acetic acid was added. Most of the solvent was distilled off under reduced pressure, and the precipitates were filtered to give compound 11a (3.25 g, 68.5%). m.p.>300° C. ¹H NMR (300 MHz, DMSO-d₆): δ 7.91 (d, J=8.8 Hz, 2H), 7.71 (d, J=1.2 Hz, 1H), 6.99 (d, J=1.2 Hz, 1H), 6.59 (d, J=8.8 Hz, 2H), 5.49 (s, 2H), 4.02 (t, J=4.4 Hz, 4H), 3.77 (t, J=4.4 Hz, 4H). MS (EI) m/e (%): 339 (M⁺, 100).

2-(p-aminophenyl)-4-(8-oxa-3-azabicyclo[3.2.1]octan-3-yl)pyrrolo[2,1-f][1,2,4]triazine-6-carboxylic acid (11b)

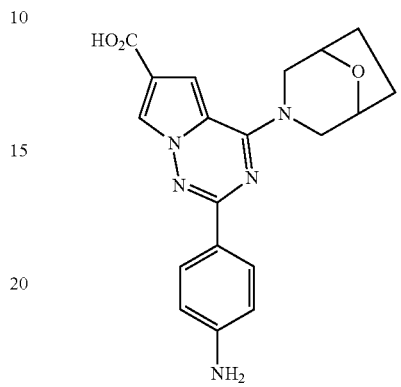

According to the same procedure as the preparation of compound 11a, 360 mg of 10b (0.95 mmol) as the starting material was hydrolyzed to give compound 11b (270 mg, 77.9%). m.p. 278-280° C. ¹H NMR (300 MHz, DMSO-d₆): δ 12.46 (s, 1H), 8.04 (d, J=1.7 Hz, 1H), 7.92 (d, J=8.8 Hz, 2H), 7.22 (d, J=1.7 Hz, 1H), 6.60 (d, J=8.8 Hz, 2H), 5.55 (br s, 2H), 4.51 (br s, 4H), 3.48 (br, s, 1H), 3.44 (br, s, 1H), 1.88-1.85 (m, 2H), 1.79-1.75 (m, 2H). LC-MS: 366 (M+1).

10. General Preparation Method of Compound 12

2-(p-aminophenyl)-N,N-dimethyl-4-morpholinopyrrolo[2,1-f][1,2,4]triazine-6-carboxamide (12a)

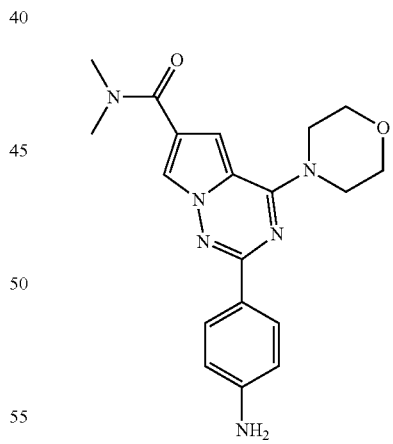

Dimethylamine hydrochloride (686 mg, 8.4 mmol) was added to 30 mL of anhydrous N,N-dimethylformamide, and potassium carbonate (3.48 g, 25.2 mmol) was added and stirred for minutes at room temperature. Then compound 11a (4.2 mmol), HBTU (benzotriazole-N,N,N',N'-tetramethyluronium hexafluorophosphate, 4.77 g, 12.6 mmol), and triethylamine (2.9 mL, 21 mmol) were added and reacted overnight at room temperature under nitrogen atmosphere. The reaction mixture was poured into water and filtered. The filtrate was extracted once with ethyl acetate, dried over anhydrous sodium sulfate, filtered and concentrated to dryness. The residue was combined with the filter cake. The crude product was purified by column chromatography (dichloromethane:methanol=100:1) to give white compound 12a (922 mg, 60.0%). m.p. 238-239° C. ¹H NMR (300 MHz, CDCl₃): δ 8.08 (d, J=8.6 Hz, 2H), 7.82 (d, J=1.4 Hz, 1H), 7.02 (d, J=1.4 Hz, 1H), 6.73 (d, J=8.6 Hz, 2H), 4.11 (t, J=4.4 Hz, 4H), 3.86 (t, J=4.4 Hz, 4H), 3.20 (br, s, 6H). MS (EI) m/e (%): 366 (M⁺, 100).

(2-(p-aminophenyl)-4-morpholinopyrrolo[2,1-f][1,2,4]triazin-6-yl)(4-(methylsulfonyl)pipera zin-1-yl)methanone (12b)

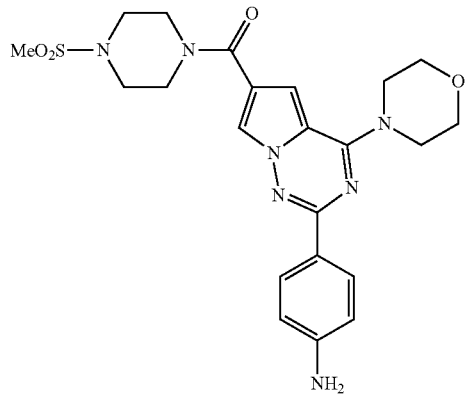 [SMILES: CS(=O)(=O)N1CCN(C(=O)c2cc3c(N4CCOCC4)nc(-c4ccc(N)cc4)nn3c2)CC1]

A white solid 12b (540 mg, 31.4%) was obtained according to the same procedure as the preparation of compound 12a, wherein 1.2 g of compound 11a (3.54 mmol) was used as starting material and methylsulfonylpiperazine trifluoromethanesulfonate (1.85 g, 7.1 mmol) was used instead of dimethylamine hydrochloride. m.p. 185-186° C. ¹H NMR (300 MHz, CDCl₃): δ 8.07 (d, J=8.6 Hz, 2H), 7.75 (d, J=1.5 Hz, 1H), 6.93 (d, J=1.5 Hz, 1H), 6.71 (d, J=8.6 Hz, 2H), 4.09 (t, J=4.8 Hz, 4H), 3.90 (t, J=4.8 Hz, 4H), 3.86 (t, J=4.8 Hz, 4H), 3.27 (t, J=4.8 Hz, 4H), 2.80 (s, 3H). LC-MS: 508 (M+23).

(2-(p-aminophenyl)-4-(8-oxa-3-azabicylclo[3.2.1]octan-3-yl)pyrrolo[2,1-f][1,2,4]triazin-6-yl)(4-(methylsulfonyl)piperazin-1-yl)methanone (12c)

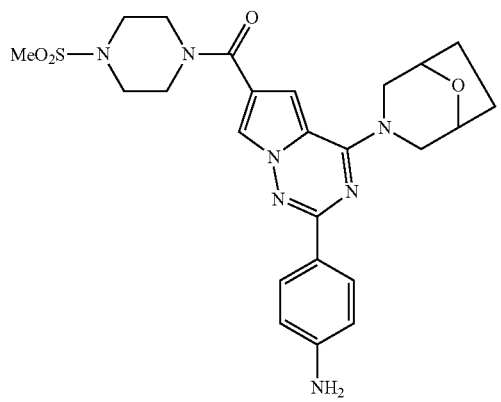 [SMILES: CS(=O)(=O)N1CCN(C(=O)c2cc3c(N4CC5CCC(C4)O5)nc(-c4ccc(N)cc4)nn3c2)CC1]

183 mg of compound 11b (0.5 mmol) was used instead of compound 11a, and compound 12c (120 mg, 46.8%) was obtained according to the same manner as the preparation of compound 12b. m.p.>300° C. ¹H NMR (300 MHz, DMSO-d₆): δ 7.96 (s, 1H), 7.91 (d, J=8.5 Hz, 2H), 7.06 (s, 1H), 6.61 (d, J=8.5 Hz, 2H), 5.53 (s, 2H), 4.51 (br, s, 4H), 3.75 (t, J=4.5 Hz, 4H), 3.48 (br s, 1H), 3.43 (br s, 1H), 3.18 (t, J=4.5 Hz, 4H), 2.91 (s, 3H), 1.90-1.75 (m, 4H). LC-MS: 511 (M⁺), 512 (M+1).

11. General Preparation Method of Compound 13

2-(p-aminophenyl)-6-(dimethylaminomethyl)-4-morpholinopyrrolo[2,1-f][1,2,4]triazine (13a)

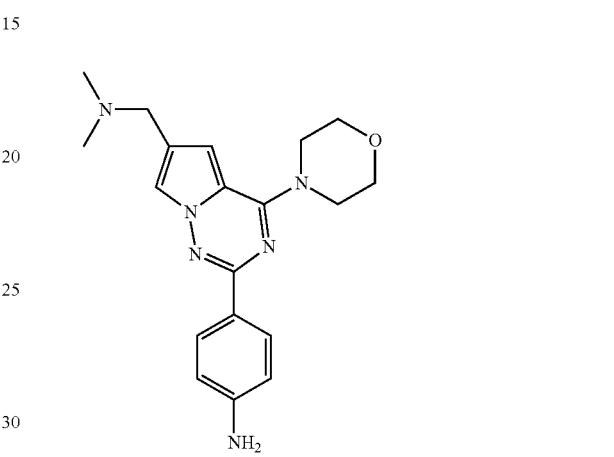

1 g of compound 12a (2.7 mmol) and 50 mL of tetrahydrofuran or dioxane were added into a 150 mL two-neck flask and refluxed under nitrogen atmosphere. 2 M of borane-dimethyl sulfide solution (10.8 mmol) was slowly added dropwise and refluxed for 2 hours. The reaction mixture was quenched with methanol and purified by column chromatography with dichloromethane to give white solid 13a (930 mg, 96.7%). m.p. 205° C. (decomposition). ¹H NMR (300 MHz, DMSO-d₆): δ 7.92 (d, J=8.5 Hz, 2H), 7.86 (s, 1H), 7.05 (s, 1H), 6.60 (d, J=8.5 Hz, 2H), 5.48 (br s, 2H), 4.02 (t, J=4.5 Hz, 4H), 3.92 (s, 2H), 3.77 (t, J=4.5 Hz, 4H), 2.42 (s, 6H). MS (EI) m/e (%): 352 (M⁺, 24).

2-(p-aminophenyl)-6-[((4-methylsulfonyl)piperazin-1-yl)methyl]-4-morpholinopyrrolo[2,1-f][1,2,4]triazine (13b)

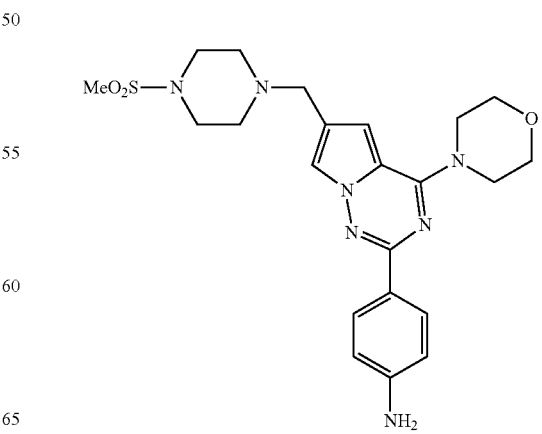

Compound 12b (540 mg, 1.1 mmol) was used instead of compound 12a as starting material, and compound 13b (288 mg, 55.0%, white solid) was prepared according to the same preparation procedure of compound 13a. m.p. 199-200° C. ¹H NMR (300 MHz, DMSO-d₆): δ 7.92 (d, J=8.6 Hz, 2H), 7.85 (d, J=1.4 Hz, 1H), 7.03 (d, J=1.4 Hz, 1H), 6.60 (d, J=8.6 Hz, 2H), 5.47 (s, 2H), 4.08 (s, 2H), 4.03 (t, J=4.6 Hz, 4H), 3.78 (t, J=4.6 Hz, 4H), 3.49-3.35 (m, 4H), 2.95 (s, 3H), 2.89 (t, J=5.7 Hz, 4H). MS (EI) m/e (%): 471 (M⁺, 12).

4-(4-(8-oxa-3-azabicylclo[3.2.1]octan-3-yl)-6-((4-(methylsulfonyl)piperazin-1-yl)methyl)pyrrolo[2,1-f][1,2,4]triazin-2-yl)aniline (13c)

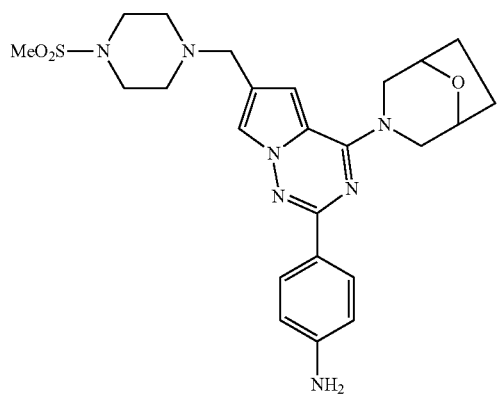 [SMILES: CS(=O)(=O)N1CCN(Cc2cc3c(N4CC5CCC(C4)O5)nc(-c4ccc(N)cc4)nn3c2)CC1]

Compound 12c (100 mg, 0.195 mmol) was used instead of compound 12a as raw material, and compound 13c was prepared according to the same preparation procedure of compound 13a as a light yellow solid (39 mg, 40.1%). ¹H NMR (300 MHz, DMSO-d₆): δ 7.89 (d, J=8.4 Hz, 2H), 7.61 (s, 1H), 6.78 (s, 1H), 6.59 (d, J=8.4 Hz, 2H), 5.46 (br s, 2H), 4.50 (br, s, 4H), 3.56 (s, 2H), 3.43 (br s, 1H), 3.39 (br s, 1H), 3.30 (br s, 4H), 3.11 (br s, 4H), 2.86 (s, 3H), 1.88-1.85 (m, 2H), 1.78-1.75 (m, 2H). MS (EI) m/e (%): 497 (M⁺, 12).

12. General Preparation Method of Compound I (1-13, 17-20)

1-ethyl-3-[4-(6-(dimethylaminomethyl)-4-morpholinopyrrolo[2,1-f][1,2,4]triazin-2-yl)phenyl]urea (I-1)

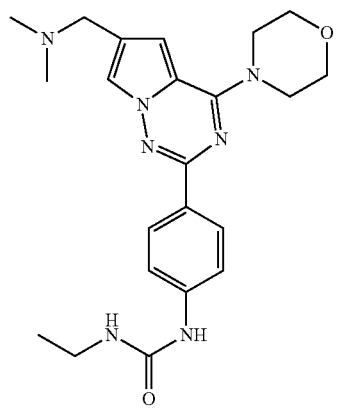 [SMILES: CCNC(=O)Nc1ccc(-c2nc(N3CCOCC3)c3cc(CN(C)C)cn3n2)cc1]

Compound 13a (0.15 mmol) was dissolved in 10 mL of anhydrous dichloromethane, and 3 equiv of ethyl isocyanate was added and stirred at room temperature overnight. The target compound was obtained by filtration.

White solid (22 mg, 34.6%). m.p. 222-224° C. ¹H NMR (300 MHz, DMSO-d₆): δ 8.65 (s, 1H), 8.09 (d, J=8.8 Hz, 2H), 7.93 (s, 1H), 7.48 (d, J=8.8 Hz, 2H), 7.11 (s, 1H), 6.16 (t, J=5.8 Hz, 1H), 4.05 (t, J=4.5 Hz, 4H), 3.94 (s, 2H), 3.78 (t, J=4.5 Hz, 4H), 3.12 (quint, J=5.8, 7.1 Hz, 2H), 2.43 (s, 6H), 1.06 (t, J=71 Hz, 3H). ESI-MS: 424 (M+1).

1-propyl-3-[4-(6-(dimethylaminomethyl)-4-morpholinopyrrolo[2,1-f][1,2,4]triazin-2-yl)phenyl]urea (I-2)

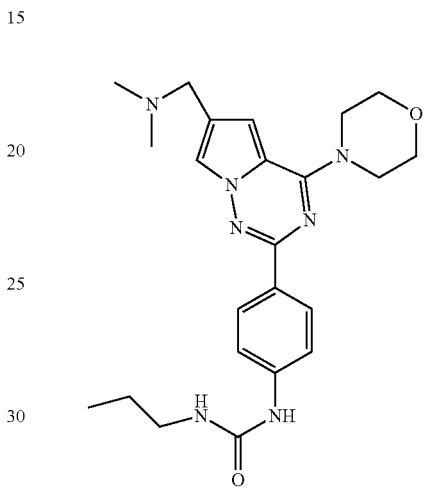

The preparation process was identical with the preparation of I-1, except that ethyl isocyanate was replaced by propyl isocyanate. White solid (23 mg, 35.1%). m.p. 224-225° C. ¹H NMR (300 MHz, DMSO-d₆): δ 8.64 (s, 1H), 8.09 (d, J=8.9 Hz, 2H), 7.93 (s, 1H), 7.48 (d, J=8.9 Hz, 2H), 7.11 (s, 1H), 6.20 (t, J=5.8 Hz, 1H), 4.05 (t, J=5.1 Hz, 4H), 3.94 (s, 2H), 3.78 (t, J =5.1 Hz, 4H), 3.05 (q, J=5.8, 7.2 Hz, 2H), 2.43 (s, 6H), 1.44 (sext, J=7.2 Hz, 2H), 0.88 (t, J=7.2 Hz, 3H). ESI-MS: 438 (M+1).

1-tert-butyl-3-[4-(6-(dimethylaminomethyl)-4-morpholinopyrrolo[2,1-f][1,2,4]triazin-2-yl)phenyl]urea (I-3)

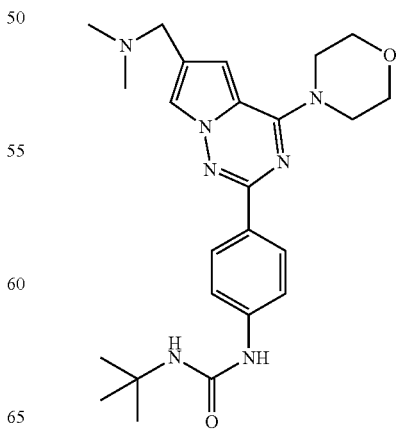

The preparation process was identical with the preparation of I-1, except that ethyl isocyanate was replaced by tert-butyl isocyanate. White solid (11 mg, 16.3%). m.p. 220-224° C. ¹H NMR (300 MHz, DMSO-d₆): δ 8.49 (s, 1H), 8.08 (d, J=8.8 Hz, 2H), 7.93 (d, J=1.0 Hz, 1H), 7.44 (d, J=8.8 Hz, 2H), 7.11 (d, 1=1.0 Hz, 1H), 6.07 (s, 1H), 4.05 (t, J=4.4 Hz, 4H), 3.94 (s, 2H), 3.78 (t, J=4.4 Hz, 4H), 2.42 (s, 6H), 1.30 (s, 9H). ESI-MS: 452 (M+1).

1-[4-(6-dimethylaminomethyl-4-morpholinopyrrolo[2,1-f][1,2,4]triazin-2-yl)phenyl]-3-(p-fluorophenyl)urea (I-4)

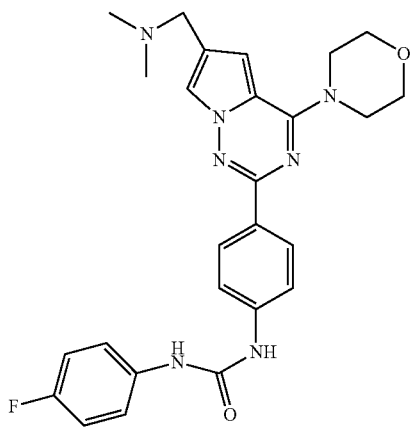 [SMILES: CN(C)Cc1cc2c(N3CCOCC3)nc(-c3ccc(NC(=O)Nc4ccc(F)cc4)cc3)nn2c1]

The preparation process was identical with the preparation of I-1, except that ethyl isocyanate was replaced by p-fluorophenyl isocyanate. White solid (30 mg, 40.9%). m.p. 217-219° C. ¹H NMR (300 MHz, DMSO-d₆): δ 8.90 (s, 1H), 8.75 (s, 1H), 8.15 (d, J=8.7 Hz, 2H), 7.95 (s, 1H), 7.55 (d, J=8.7 Hz, 2H), 7.47 (dd, J=4.6, 8.8 Hz, 2H), 7.13 (t, J=8.8 Hz, 2H), 7.13 (s, 1H), 4.06 (t, J=4.6 Hz, 4H), 3.94 (s, 2H), 3.79 (t, J=4.6 Hz, 4H), 2.43 (s, 6H). ESI-MS: 490 (M+1).

1-[4-(6-dimethylaminomethyl-4-morpholinopyrrolo[2,1-f][1,2,4]triazin-2-yl)phenyl]-3-(p-chlorophenyl)urea (I-5)

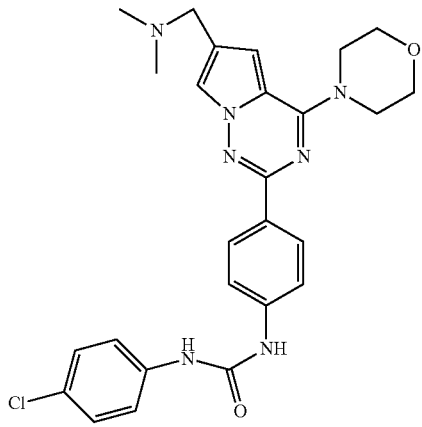 [SMILES: CN(C)Cc1cc2c(N3CCOCC3)nc(-c3ccc(NC(=O)Nc4ccc(Cl)cc4)cc3)nn2c1]

The preparation process was identical with the preparation of I-1, except that ethyl isocyanate was replaced by p-chlorophenyl isocyanate. White solid (43 mg, 56.8%). m.p. 237° C. (decomposition). ¹H NMR (300 MHz, DMSO-d₆): δ 8.95 (s, 1H), 8.87 (s, 1H), 8.15 (d, J=8.5 Hz, 2H), 7.95 (s, 1H), 7.55 (d, J=8.5 Hz, 2H), 7.50 (d, J=8.7 Hz, 2H), 7.34 (d, J=8.7 Hz, 2H), 7.13 (s, 1H), 4.06 (t, J=4.5 Hz, 4H), 3.94 (s, 2H), 3.79 (t, J=4.5 Hz, 4H), 2.43 (s, 6H). ESI-MS: 506 (M+1), 508 (M+2+1).

1-(3-chlorophenyl)-3-(4-(6-((dimethylamino)methyl)-4-morpholinopyrrolo[2,1-f][1,2,4]triazin-2-yl)phenyl)urea (I-6)

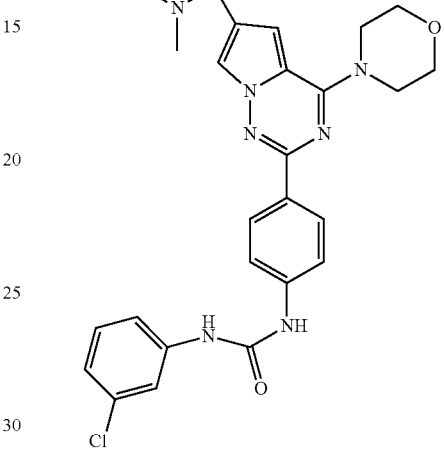

The preparation process was identical with the preparation of I-1, except that ethyl isocyanate was replaced by m-chlorophenyl isocyanate. White solid (25 mg, 33.0%). m.p. 173-176° C. ¹H NMR (300 MHz, DMSO-d₆): δ 9.00 (s, 1H), 8.94 (s, 1H), 8.16 (d, J=8.8 Hz, 2H), 7.95 (d, J=1.3 Hz, 1H), 7.73 (t, J=1.9 Hz, 1H), 7.56 (d, J=8.8 Hz, 2H), 7.34-7.25 (m, 2H), 7.13 (d, J=1.3 Hz, 1H), 7.03 (dt, J=1.9, 7.0 Hz, 1H), 4.07 (t, J=4.6 Hz, 4H), 3.94 (s, 2H), 3.79 (t, J=4.6 Hz, 4H), 2.43 (s, 6H). ESI-MS: 506 (M+1), 508 (M+2+1).

1-(2,4-dichlorophenyl)-3-(4-(6-((dimethylamino)methyl)-4-morpholinopyrrolo[2,1-f][1,2,4]triazin-2-yl)phenyl)urea (I-7)

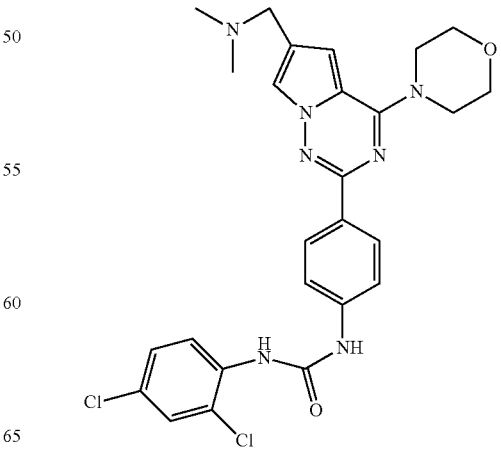

The preparation process was identical with the preparation of I-1, except that ethyl isocyanate was replaced by 2,4-dichlorophenyl isocyanate. White solid (29 mg, 35.8%). m.p. 225° C. (decomposition). $^1$H NMR (300 MHz, DMSO-$d_6$): δ 9.66 (s, 1H), 8.45 (s, 1H), 8.22 (d, J=9.0 Hz, 1H), 8.18 (d, J=8.8 Hz, 2H), 7.95 (d, J=1.4 Hz, 1H), 7.64 (d, J=2.4 Hz, 1H), 7.57 (d, J =8.8 Hz, 2H), 7.40 (dd, J=2.4, 9.0 Hz, 1H), 7.13 (d, J=1.4 Hz, 1H), 4.07 (t, J=4.7 Hz, 4H), 3.95 (s, 2H), 3.79 (t, J=4.7 Hz, 4H), 2.43 (s, 6H). ESI-MS: 540 (M+1), 542 (M+2+1).

1-(4-(6-((dimethylamino)methyl)-4-morpholinopyrrolo[2,1-f][1,2,4]triazin-2-yl)phenyl)3-(3-(trifluoromethyl)phenyl)urea (I-8)

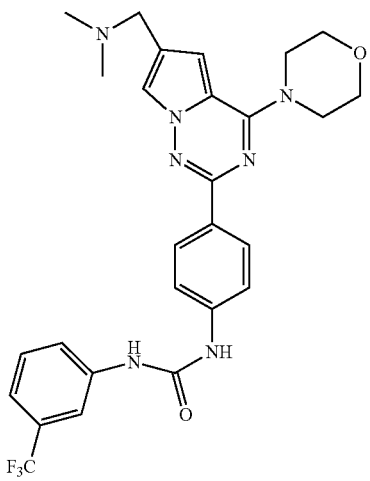 [SMILES: CN(C)Cc1cc2c(N3CCOCC3)nc(-c3ccc(NC(=O)Nc4cccc(Cl)c4)cc3)nn2c1]

The preparation process was identical with the preparation of I-1, except that ethyl isocyanate was replaced by m-trifluorophenyl isocyanate. White solid (81 mg, 100%). m.p. 160-163° C. $^1$H NMR (300 MHz, DMSO-$d_6$): δ 9.73 (s, 1H), 9.55 (s, 1H), 8.16 (d, J=8.8 Hz, 2H), 8.01 (s, 1H), 7.96 (d, J=1.1 Hz, 1H), 7.61 (d, J=8.6 Hz, 1H), 7.57 (d, J=8.8 Hz, 2H), 7.52 (t, J=7.5, 8.6 Hz, 1H), 7.31 (d, J=7.5 Hz, 1H), 7.12 (d, J=1.1 Hz, 1H), 4.07 (t, J=4.4 Hz, 4H), 3.94 (s, 2H), 3.79 (t, J=4.4 Hz, 4H), 2.43 (s, 6H). ESI-MS: 540 (M+1).

1-(4-(6-((dimethylamino)methyl)-4-morpholinopyrrolo[2,1-f][1,2,4]triazin-2-yl)phenyl)-3-(p-tolyl)urea (I-9)

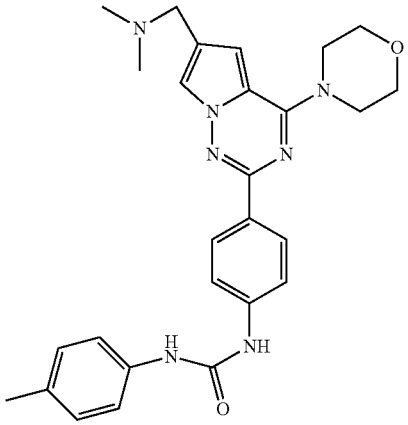 [SMILES: Cc1ccc(NC(=O)Nc2ccc(-c3nc(N4CCOCC4)c4cc(CN(C)C)cn4n3)cc2)cc1]

The preparation process was identical with the preparation of I-1, except that ethyl isocyanate was replaced by p-tolyl isocyanate. White solid (37 mg, 50.8%). m.p. 230° C. (decomposition). $^1$H NMR (300 MHz, DMSO-$d_6$): δ 8.86 (s, 1H), 8.61 (s, 1H), 8.15 (d, J=8.8 Hz, 2H), 7.95 (d, J=1.2 Hz, 1H), 7.55 (d, J=8.8 Hz, 2H), 7.35 (d, J=8.6 Hz, 2H), 7.13 (d, J=1.2 Hz, 1H), 7.09 (d, J=8.6 Hz, 2H), 4.06 (t, J=4.6 Hz, 4H), 3.94 (s, 2H), 3.79 (t, J=4.6 Hz, 4H), 2.43 (s, 6H), 2.24 (s, 3H). ESI-MS: 486 (M+1).

1-(4-(6-((dimethylamino)methyl)-4-morpholinopyrrolo[2,1-f][1,2,4]triazin-2-yl)phenyl)-3-(4-methoxyphenyl)urea (I-10)

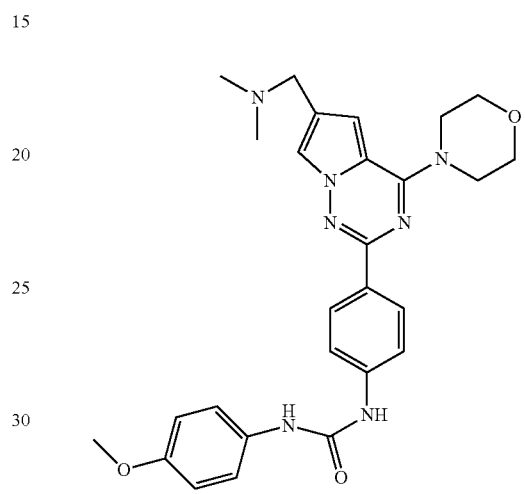

The preparation process was identical with the preparation of I-1, except that ethyl isocyanate was replaced by p-methoxylphenyl isocyanate. White solid (49 mg, 65.2%). m.p. 235° C. (decomposition). $^1$H NMR (300 MHz, DMSO-$d_6$): δ 8.82 (s, 1H), 8.52 (s, 1H), 8.14 (d, J=8.8 Hz, 2H), 7.94 (s, 1H), 7.55 (d, J=8.8 Hz, 2H), 7.37 (d, J=8.8 Hz, 2H), 7.12 (s, 1H), 6.87 (d, J=8.8 Hz, 2H), 4.06 (t, J=4.5 Hz, 4H), 3.95 (s, 2H), 3.79 (t, J=4.5 Hz, 4H), 3.72 (s, 3H), 2.43 (s, 6H). ESI-MS: 502 (M+1).

1-(4-(6-((dimethylamino)methyl)-4-morpholinopyrrolo[2,1-f][1,2,4]triazin-2-yl)phenyl)-3-(4-fluorobenzyl)urea (I-11)

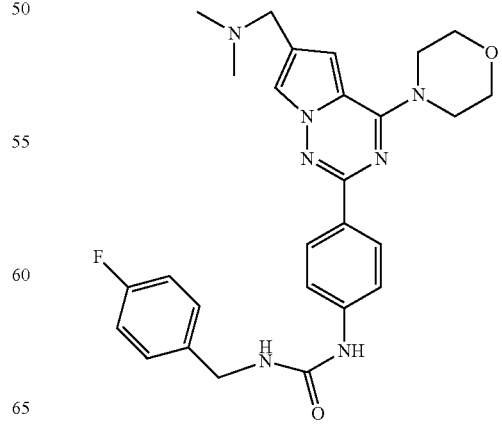

The preparation process was identical with the preparation of I-1, except that ethyl isocyanate was replaced by p-fluorobenzyl isocyanate. White solid (32 mg, 42.4%). m.p. 219-223° C. ¹H NMR (300 MHz, DMSO-d₆): δ 8.83 (s, 1H), 8.10 (d, J=8.8 Hz, 2H), 7.93 (s, 1H), 7.50 (d, J=8.8 Hz, 2H), 7.35 (dd, J=5.7, 8.6 Hz, 2H), 7.16 (t, J=8.6 Hz, 2H), 6.70 (t, J=5.5 Hz, 1H), 7.11 (s, 1H), 4.29 (d, J=5.5 Hz, 2H), 4.05 (t, J=4.4 Hz, 4H), 3.94 (s, 2H), 3.78 (t, J=4.4 Hz, 4H), 2.42 (s, 6H). ESI-MS: 504 (M+1).

1-(4-(6-((dimethylamino)methyl)-4-morpholinopyrrolo[2,1-f][1,2,4]triazin-2-yl)phenyl)-3-(3,5-dimethylisoxazol-4-yl)urea (I-12)

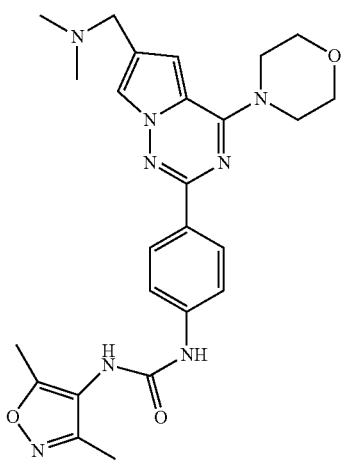 [SMILES: Cc1noc(C)c1NC(=O)Nc1ccc(-c2nc(N3CCOCC3)c3cc(CN(C)C)cn3n2)cc1]

The preparation process was identical with the preparation of I-1, except that ethyl isocyanate was replaced by 3,5-dimethylisoxazoly-4-isocyanate. White solid (24 mg, 31.7%). m.p. 236° C. (decomposition). ¹H NMR (300 MHz, DMSO-d₆): δ 9.05 (s, 1H), 8.14 (d, J=8.8 Hz, 2H), 7.94 (d, J=1.6 Hz, 1H), 7.76 (s, 1H), 7.55 (d, J=8.8 Hz, 2H), 7.12 (d, J=1.6 Hz, 1H), 4.06 (t, J=4.5 Hz, 4H), 3.94 (s, 2H), 3.79 (t, J=4.5 Hz, 4H), 2.43 (s, 6H), 2.30 (s, 3H), 2.13 (s, 3H). ESI-MS: 505 (M+1).

Ethyl 4-(3-(4-(6-((dimethylamino)methyl)-4-morpholinopyrrolo[2,1-f][1,2,4]triazin-2-yl)phenyl)-ureido)benzoate (I-13)

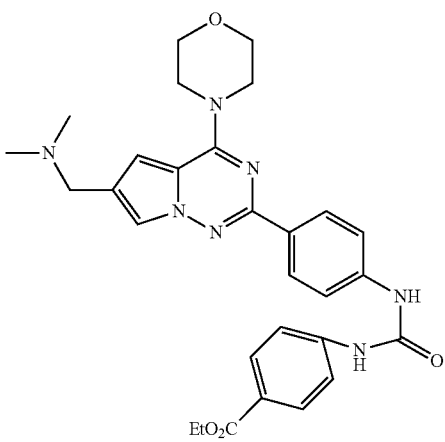 [SMILES: CCOC(=O)c1ccc(NC(=O)Nc2ccc(-c3nc(N4CCOCC4)c4cc(CN(C)C)cn4n3)cc2)cc1]

The preparation process was identical with the preparation of I-1, except that ethyl isocyanate was replaced by p-ethoxycarbonylphenyl isocyanate. White solid (47 mg, 57.7%). m.p. 175-176° C. ¹H NMR (300 MHz, DMSO-d₆): δ 8.24 (d, J=8.5 Hz, 2H), 8.01 (d, J=8.7 Hz, 2H), 7.68 (s, 1H), 7.49 (d, J=8.5 Hz, 2H), 7.42 (d, J=8.7 Hz, 2H), 6.92 (s, 1H), 6.78 (s, 1H), 6.70 (s, 1H), 4.36 (q, J=7.0 Hz, 2H), 4.10 (t, J=4.5 Hz, 4H), 4.03 (s, 2H), 3.89 (t, J=4.5 Hz, 4H), 2.58 (s, 6H), 1.39 (t, J=7.0 Hz, 3H). ESI-MS: 544 (M+1).

1-Ethyl-3-(4-(6-((4-(methylsulfonyl)piperazin-1-yl)methyl)-4-morpholinopyrrolo[2,1-f][1,2,4]triazin-2-yl)phenyl)urea (I-17)

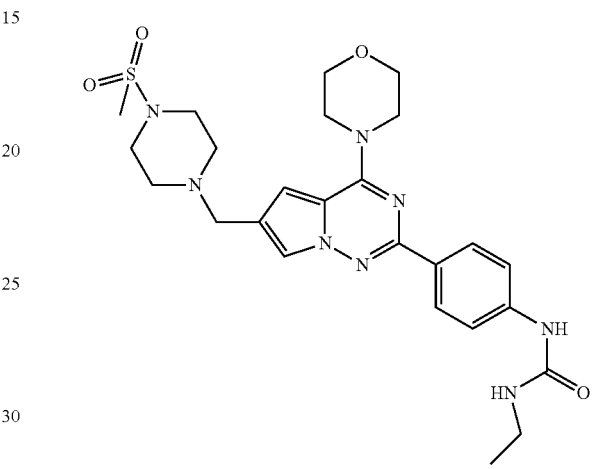

The preparation process was identical with the preparation of I-1, except that 13a was replaced by compound 13b. White solid (34 mg, 41.8%). m.p. 200° C. (decomposition). ¹H NMR (300 MHz, DMSO-d₆): δ 8.92 (s, 1H), 8.08 (d, J=8.8 Hz, 2H), 7.92 (s, 1H), 7.49 (d, J=8.8 Hz, 2H), 7.09 (s, 1H), 6.36 (t, J=5.6 Hz, 1H), 4.10 (s, 2H), 4.05 (t, J=4.5 Hz, 4H), 3.79 (t, J=4.5 Hz, 4H), 3.49-3.37 (m, 4H), 3.11 (quint, J=5.6, 7.0 Hz, 2H), 2.96 (s, 3H), 2.89 (br, s, 4H), 1.05 (t, J=7.0 Hz, 3H). ESI-MS: 543 (M+1)

1-(4-fluorophenyl)-3-(4-(6-((4-(methylsulfonyl)piperazin-1-yl)methyl)-4-morpholinopyrrolo[2,1-f][1,2,4]triazin-2-yl)phenyl)urea (I-18)

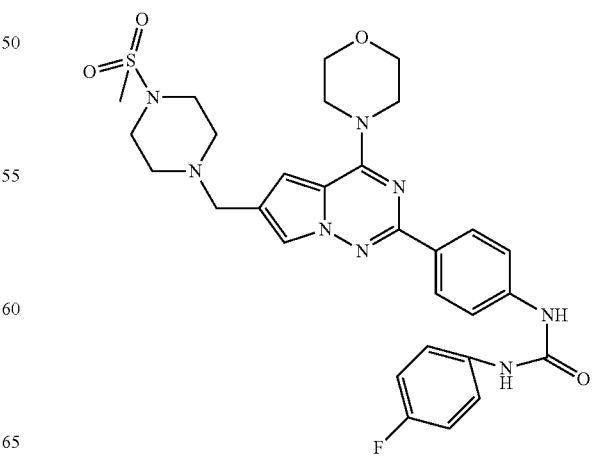

The preparation process was identical with the preparation of I-4, except that 13a was replaced by compound 13b. White solid (45 mg, 49.3%). m.p. 255-256° C. $^1$H NMR (300 MHz, DMSO-d$_6$): δ 8.89 (s, 1H), 8.74 (s, 1H), 8.15 (d, J=8.8 Hz, 2H), 7.93 (s, 1H), 7.56 (d, J=8.8 Hz, 2H), 7.47 (dd, J=4.8, 8.8 Hz, 2H), 7.13 (t, J=8.8 Hz, 2H), 6.50 (s, 1H), 4.10 (s, 2H), 4.07 (br, s, 4H), 3.80 (br, s, 4H), 3.58-3.38 (m, 4H), 2.96 (s, 3H), 2.90 (br, s, 4H). ESI-MS: 609 (M+1).

1-(4-(4-(8-oxa-3-azabicyclo[3.2.1]octan-3-yl)-6-((4-(methylsulfonyl)piperazin-1-yl)methyl)-pyrrolo[2,1-f][1,2,4]triazin-2-yl)phenyl)-3-(4-fluorophenyl)urea (I-19)

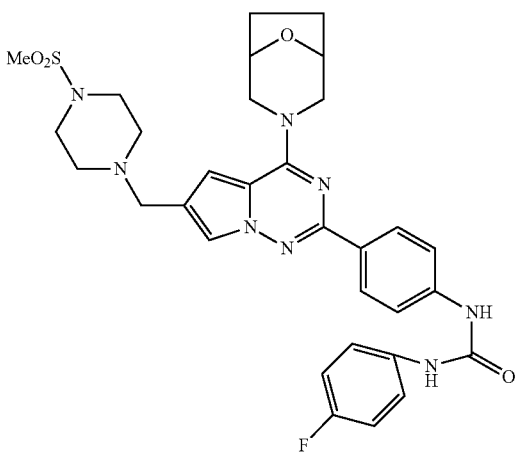 [SMILES: CS(=O)(=O)N1CCN(Cc2cc3c(N4CC5CCC(C4)O5)nc(-c4ccc(NC(=O)Nc5ccc(F)cc5)cc4)nn3c2)CC1]

The preparation process was identical with the preparation of I-4, except that 13a was replaced by compound 13c. White solid (31 mg, 32.6%). m.p. 266-267° C. $^1$H NMR (300 MHz, DMSO-d$_6$): δ 8.89 (s, 1H), 8.75 (s, 1H), 8.13 (d, J=8.5 Hz, 2H), 7.70 (s, 1H), 7.54 (d, J=8.5 Hz, 2H), 7.47 (dd, J=5.0, 8.8 Hz, 2H), 7.13 (t, J=8.8 Hz, 2H), 6.84 (s, 1H), 4.51 (br, s, 4H), 3.57 (s, 2H), 3.47 (br s, 1H), 3.43 (br s, 1H), 3.32 (br s, 4H), 3.11 (t, J=4.0 Hz, 4H), 2.87 (s, 3H), 1.89-1.85 (m, 2H), 1.80-1.76 (m, 2H). ESI-MS: 635 (M+1).

Ethyl 4-(-3-(4-(6-((4-(methylsulfonyl)piperazin-1-yl)methyl)-4-morpholinopyrrolo[2,1-f][1,2,4]triazin-2-yl)phenyl)ureido)benzoate (I-20)

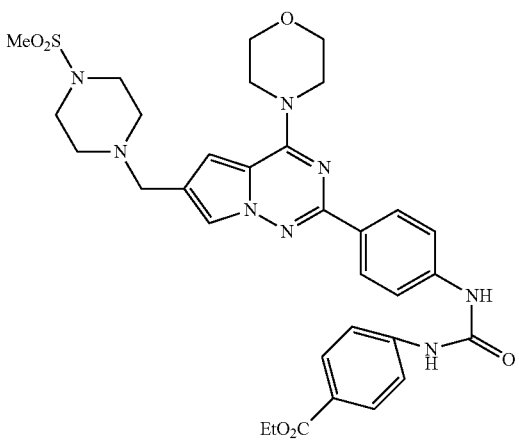 [SMILES: CCOC(=O)c1ccc(NC(=O)Nc2ccc(-c3nc(N4CCOCC4)c4cc(CN5CCN(S(C)(=O)=O)CC5)cn4n3)cc2)cc1]

The preparation process was identical with the preparation of I-13, except that 13a was replaced by compound 13b. White solid (40 mg, 40.2%). m.p. 260-262° C. $^1$H NMR (300 MHz, DMSO-d$_6$): δ 9.15 (s, 1H), 9.02 (s, 1H), 8.16 (d, J=8.8 Hz, 2H), 7.90 (d, J=8.8 Hz, 2H), 7.72 (s, 1H), 7.62-7.56 (m, 4H), 6.90 (s, 1H), 6.52 (s, 3H), 4.28 (q, J=7.0 Hz, 2H), 4.05 (br s, 4H), 3.79 (br s, 4H), 3.58 (s, 2H), 3.11 (br s, 4H), 2.87 (br s, 4H), 1.31 (t, J=7.0 Hz, 3H). ESI-MS: 663 (M+1).

13. General Preparation Method for Compounds I-14~I-16

The corresponding carboxylic acid (0.5 mmol) was dissolved in anhydrous N,N-dimethylformamide and triethylamine (101 mg, 1 mmol), and diphenyl azidophosphate (165 mg, 0.6 mmol) was added and reacted at room temperature for 1 hour. The reaction mixture was poured into water and filtered, and the filter cake was dried in a vacuum oven at room temperature for 24 hours to give p-carbamoylbenzoyl azide. Compound 13 (0.1 mmol) and p-carbamoylbenzoyl azide (0.2 mmol) in anhydrous dioxane were refluxed for 3 hours. The solvent was distilled off under reduced pressure. The residue was dissolved in a mixed solvent of dichloromethane and methanol and purified by preparative thin layer chromatography (dichloromethane:methanol=8:1), so as to give a pure desired product.

4-(3-(4-(6-((dimethylamino)methyl)-4-morpholinopyrrolo[2,1-f][1,2,4]triazin-2-yl)phenyl)ureido)-N,N-dimethylbenzamide (I-14)

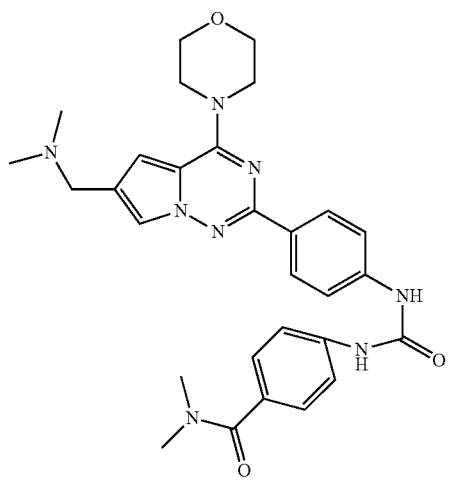 [SMILES: CN(C)Cc1cc2c(N3CCOCC3)nc(-c3ccc(NC(=O)Nc4ccc(C(=O)N(C)C)cc4)cc3)nn2c1]

According to the general method described in example 13, 4-(dimethylcarbamoyl)benzoic acid was used as starting material, and the resulting 4-(dimethylcarbamoyl)benzoyl azide reacted with 13a to give a light yellow solid (14 mg, 25.8%). m.p. 240° C. $^1$H NMR (300 MHz, DMSO-d$_6$): δ 9.59 (s, 2H), 8.16 (d, J=8.5 Hz, 2H), 7.99 (s, 1H), 7.58 (d, J=8.5 Hz, 2H), 7.52 (d, J=8.5 Hz, 2H), 7.36 (d, J=8.5 Hz, 2H), 7.19 (s, 1H), 4.25 (s, 2H), 4.08 (t, J=4.4 Hz, 4H), 3.80 (t, J=4.4 Hz, 4H), 2.96 (s, 6H), 2.69 (s, 6H). ESI-MS: 543 (4+1).

1-(4-(6-((dimethylamino)methyl)-4-morpholinopyrrolo[2,1-f][1,2,4]triazin-2-yl)phenyl)-3-(4-(4-methylpiperazine-1-carbonyl)phenyl)urea (I-15)

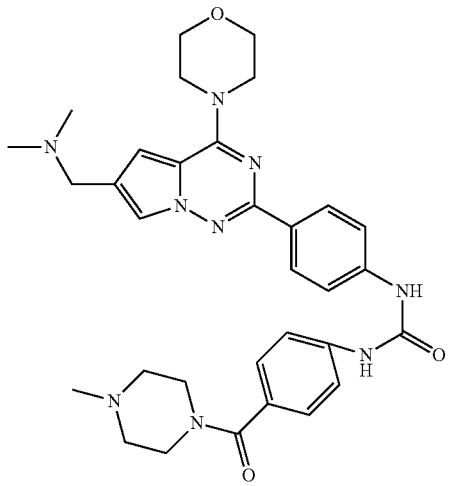 [SMILES: CN(C)Cc1cc2c(N3CCOCC3)nc(-c3ccc(NC(=O)Nc4ccc(C(=O)N5CCN(C)CC5)cc4)cc3)nn2c1]

According to the general methods described in example 13, 4-(4-methylpiperazine-1-carbonyl)benzoic acid was used as starting material, and the resulting 4-(4-methylpiperazine-1-carbonyl)benzoyl azide reacted with 13a to give a white solid (9 mg, 15.1%). $^1$H NMR (300 MHz, DMSO-d$_6$): δ 9.63 (br, s, 2H), 8.16 (d, J=8.9 Hz, 2H), 7.92 (s, 1H), 7.57 (d, J=8.9 Hz, 2H), 7.53 (d, J=8.5 Hz, 2H), 7.34 (d, J=8.5 Hz, 2H), 7.13 (s, 1H), 4.07 (br, s, 6H), 3.80 (br, s, 4H), 3.51 (br, s, 4H), 3.06 (br s, 2H), 2.55 (s, 6H), 2.38 (br s, 2H), 2.24 (s, 3H). ESI-MS: 598 (M+1).

1-(4-(6-((dimethylamino)methyl)-4-morpholinopyrrolo[2,1-f][1,2,4]triazin-2-yl)phenyl)-3-(4-(piperidine-1-carbonyl)phenyl)urea (I-16)

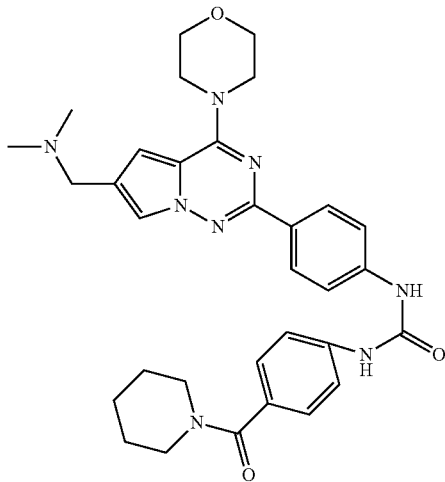 [SMILES: CN(C)Cc1cc2c(N3CCOCC3)nc(-c3ccc(NC(=O)Nc4ccc(C(=O)N5CCCCC5)cc4)cc3)nn2c1]

According to the general method described in example 13, 4-(piperidine-1-carbonyl)benzoic acid was used as starting material, and the resulting 4-(piperidine-1-carbonyl)benzoyl azide reacted with 13a to give a yellow solid (11 mg, 18.9%). m.p. 184-186° C. $^1$H NMR (300 MHz, DMSO-d$_6$): δ 9.57 (s, 2H), 8.15 (d, J=8.8 Hz, 2H), 7.93 (s, 1H), 7.57 (d, J=8.8 Hz, 2H), 7.52 (d, J=8.6 Hz, 2H), 7.31 (d, J=8.6 Hz, 2H), 7.13 (s, 1H), 4.07 (br, s, 6H), 3.79 (t, J=4.3 Hz, 4H), 3.38 (br, s, 4H), 2.58 (s, 6H), 1.60 (br, s, 2H), 1.50 (br, s, 4H). ESI-MS: 583 (M+1).

14. Preparation of 4-(3-(-4(6-((4-(methylsulfonyl)piperazin-1-yl)methyl)-4-morpholinopyrrolo[2,1-f][1,2,4]triazin-2-yl)phenyl)ureido)benzoic acid (14)

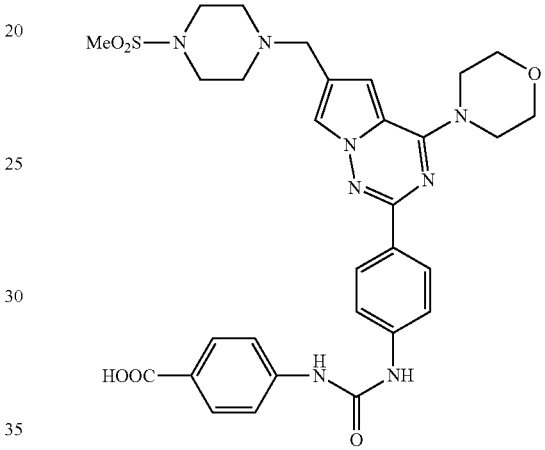

Compound I-20 (395 mg, 0.6 mmol) was suspended in 20 mL of tetrahydrofuran and 10 mL of methanol, and 4 mL of 1 M potassium hydroxide solution was added and refluxed for 3 hours. The reaction mixture was cooled and 2 mL of acetic acid was added to precipitate solids. After filtered, white solids (312 mg, 82.0%) were obtained. m.p. 207-209° C. $^1$H NMR (300 MHz, DMSO-d$_6$): δ 9.16 (s, 1H), 9.08 (s, 1H), 8.16 (d, J=8.7 Hz, 2H), 7.88 (d, J=8.7 Hz, 2H), 7.71 (s, 1H), 7.58 (d, J=7.9 Hz, 4H), 6.87 (s, 1H), 4.04 (br s, 4H), 3.79 (br s, 4H), 3.58 (s, 2H), 3.34 (br, s, 4H), 3.11 (br s, 4H), 2.87 (s, 3H). LC-MS: 635 (M+1).

15. General Preparation Methods for Compound I-21~I-23

Compound 14 (95 mg, 0.15 mmol), diisopropylethylamine (116 mg, 0.9 mmol), and HBTU (benzotriazol-N,N,N',N'-tetramethyluronium hexafluorophosphate, 284 mg, 0.75 mmol) were dissolved in 5 mL of N,N-dimethylformamide and stirred for 1 hour at room temperature. Each corresponding amine (0.6 mmol) was added and stirred at room temperature for 4-6 hours. The reaction mixture was poured into 50 mL of water and extracted with ethyl acetate. The resulting mixture was separated by a preparative plate (dichloromethane:methanol=10:1) to give a product.

67

N,N-dimethyl-4-(3-(4-(6-((4-(methylsulfonyl)piperazin-1-yl)methyl)-4-morpholinopyrrolo[2,1-f][1,2,4]triazin-2-yl)phenyl)ureido)benzamide (I-21)

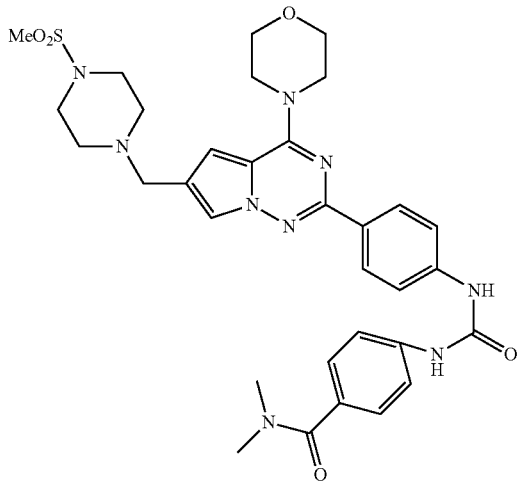 [SMILES: CN(C)C(=O)c1ccc(NC(=O)Nc2ccc(-c3nc(N4CCOCC4)c4cc(CN5CCN(S(C)(=O)=O)CC5)cn4n3)cc2)cc1]

Light yellow solid (38 mg, 38.3%). m.p. 248-250° C. $^1$H NMR (300 MHz, DMSO-d$_6$): δ 9.40 (s, 2H), 8.15 (d, J=8.8 Hz, 2H), 7.72 (s, 1H), 7.57 (d, J=8.9 Hz, 2H), 7.52 (d, J=8.9 Hz, 2H), 7.36 (d, J=8.8 Hz, 2H), 6.89 (s, 1H), 4.05 (t, J=4.4 Hz, 4H), 3.79 (t, J=4.4 Hz, 4H), 3.59 (s, 2H), 3.32 (br s, 4H), 3.12 (br s, 4H), 2.96 (s, 6H), 2.87 (s, 3H). ESI-MS: 684 (M+23).

1-(4-(4-methylpiperazine-1-carbonyl)phenyl)-3-(4-(6-((4-(methylsulfonyl)piperazin-1-yl)methyl)-4-morpholinopyrrolo[2,1-f][1,2,4]triazin-2-yl)phenyl)urea (I-22)

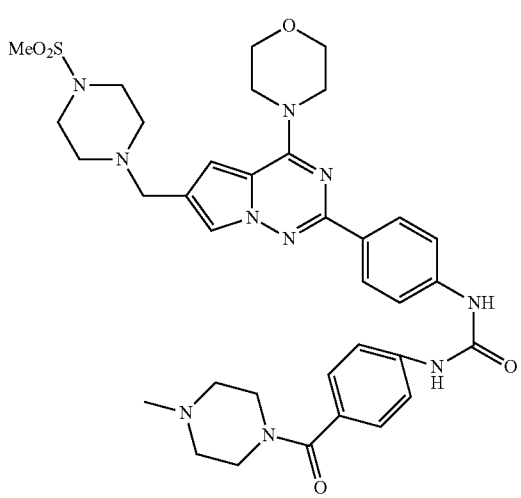 [SMILES: CN1CCN(C(=O)c2ccc(NC(=O)Nc3ccc(-c4nc(N5CCOCC5)c5cc(CN6CCN(S(C)(=O)=O)CC6)cn5n4)cc3)cc2)CC1]

Light yellow solid (40 mg, 37.2%). m.p. 185-188° C. $^1$H NMR (300 MHz, DMSO-d$_6$): δ 9.03 (s, 1H), 9.02 (s, 1H), 8.15 (d, J=8.7 Hz, 2H), 7.71 (s, 1H), 7.58-7.52 (m, 4H), 7.34 (d, J=8.7 Hz, 2H), 6.89 (s, 1H), 4.04 (t, J=4.7 Hz, 4H), 3.79 (t, J=4.7 Hz, 4H), 3.59 (s, 2H), 3.50 (br s, 4H), 3.32 (br s, 4H), 3.12 (br s, 4H), 2.87 (s, 3H), 2.38 (br s, 4H), 2.24 (s, 3H). ESI-MS: 717 (M+1).

68

1-(4-(4-(dimethylamino)piperidine-1-carbonyl)phenyl)-3-(4-(6-((4-(methylsulfonyl)piperazin-1-yl)methyl)-4-morpholinopyrrolo[2,1-f][1,2,4]triazin-2-yl)phenyl)urea (I-23)

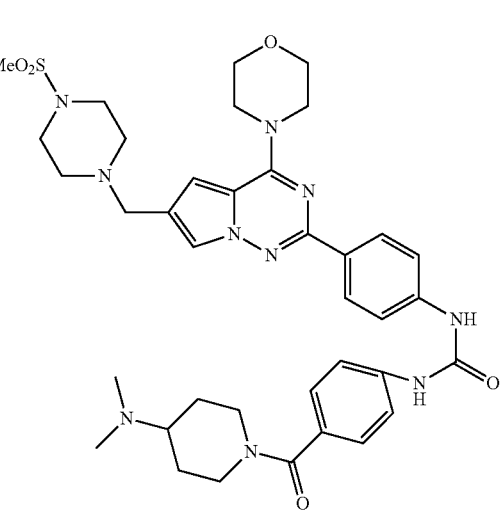

White solid (44 mg, 39.4%). m.p. 200-202° C. $^1$H NMR (300 MHz, DMSO): δ 9.12 (s, 2H), 8.15 (d, J=8.6 Hz, 2H), 7.71 (s, 1H), 7.58-7.53 (m, 4H), 7.37 (d, J=8.6 Hz, 2H), 6.90 (s, 1H), 4.05 (t, J=4.2 Hz, 4H), 3.79 (t, J=4.2 Hz, 4H), 3.59 (s, 2H), 3.32 (br s, 8H), 3.12 (br s, 4H), 2.87 (s, 3H), 2.94 (s, 1H), 2.68 (s, 6H), 2.05-1.91 (m, 2H), 1.63-1.48 (m, 2H). ESI-MS: 745 (M+1).

16. Preparation of methyl 2-(3-(acetoxymethyl)phenyl)-4-chloropyrrolo[2,1-f][1,2,4]triazine-6-carboxylate (15)

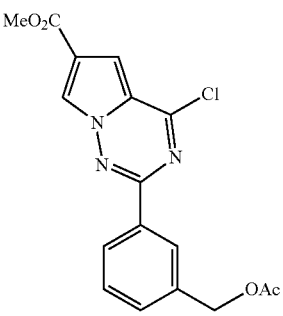 [SMILES: COC(=O)c1cc2c(Cl)nc(-c3cccc(COC(C)=O)c3)nn2c1]

Compound 15 was prepared by the method which was identical with that for preparing compound 8, wherein compound IIIb (341 mg, 1 mmol) was used as the starting material. The crude product was purified by column chromatography (petroleum ether:ethyl acetate=5:1) to obtain white solid (197 mg, 54.8%). m.p. 154-155° C. $^1$H NMR (300 MHz, CDCl$_3$): δ 8.33-8.29 (m, 3H), 7.52-7.50 (m, 2H), 7.41 (d, J=1.3 Hz, 1H), 5.20 (s, 2H), 3.94 (s, 3H), 2.14 (s, 3H). LC-MS: 360 (M+1), 362 (M+2+1).

17. Preparation of methyl 2-(3-(acetoxymethyl)phenyl)-4-morpholinopyrrolo[2,1-f][1,2,4]triazine-6-carboxylate (16)

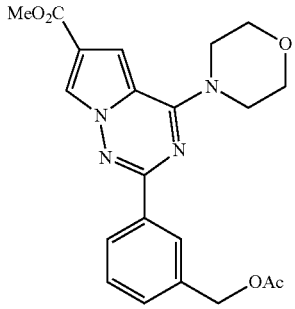 [SMILES: COC(=O)c1cc2c(N3CCOCC3)nc(-c3cccc(COC(C)=O)c3)nn2c1]

Compound 16 was prepared by the method which was identical with that for preparing compound 9, wherein compound 15 (180 mg, 0.5 mmol) was used as the starting material. White solid (177 mg, 86.3%). m.p. 204-205° C. $^1$H NMR (300 MHz, CDCl$_3$): δ 8.26-8.22 (m, 2H), 8.13 (s, 1H), 7.46 (d, J=4.5 Hz, 2H), 7.19 (s, 1H), 5.19 (s, 2H), 4.15 (t, J=4.8 Hz, 4H), 3.90 (s, 3H), 3.90 (t, J=4.8 Hz, 4H), 2.13 (s, 3H). LC-MS: 411 (M+1).

18. Preparation of 2-(3-(hydroxymethyl)phenyl)-4-morpholinopyrrolo[2,1-f][1,2,4]triazine-6-carboxylic acid (17)

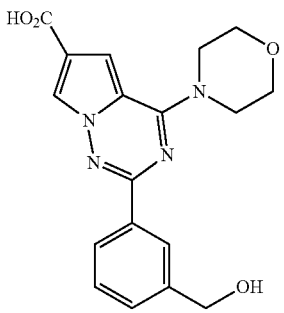 [SMILES: O=C(O)c1cc2c(N3CCOCC3)nc(-c3cccc(CO)c3)nn2c1]

Compound 17 was prepared by the method which was identical with that for preparing compound 11, wherein compound 16 (150 mg, 0.366 mmol) was used as the starting material. White solid (111 mg, 85.7%). m.p. 254° C. (decomposition). $^1$H NMR (300 MHz, DMSO-d$_6$): 12.64 (s, 1H), 8.21 (s, 1H), 8.19 (d, J=1.6 Hz, 1H), 8.13-8.10 (m, 1H), 7.44-7.42 (m, 2H), 7.36 (d, J=1.6 Hz, 1H), 5.30 (s, 1H), 4.58 (s, 2H), 4.10 (t, J=4.5 Hz, 4H), 3.80 (t, J=4.5 Hz, 4H). LC-MS: 355 (M+1).

19. Preparation of 2-(3-(hydroxymethyl)phenyl)-N,N-dimethyl-4-morpholinopyrrolo[2,1-f][1,2,4]triazine-6-carboxamide (18)

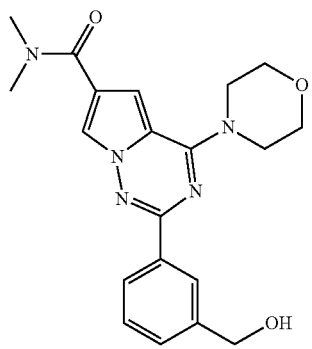 [SMILES: CN(C)C(=O)c1cc2c(N3CCOCC3)nc(-c3cccc(CO)c3)nn2c1]

Compound 18 was prepared by the method which was identical with that for preparing compound 12a, wherein compound 17 (92 mg, 0.26 mmol) was used as the starting material. White solid (80 mg, 80.8%). m.p. 170-171° C. $^1$H NMR (300 MHz, CDCl$_3$): δ 8.22 (s, 1H), 8.20-8.17 (m, 1H), 7.84 (d, J=1.5 Hz, 1H), 7.46-7.43 (m, 2H), 7.04 (d, J=1.5 Hz, 1H), 4.77 (s, 2H), 4.11 (t, J=4.7 Hz, 4H), 3.87 (t, J=4.7 Hz, 4H), 3.20 (br, s, 6H). LC-MS: 382 (M+1).

20. Preparation of (3-(6-((dimethylamino)methyl)-4-morpholinopyrrolo[2,1-f][1,2,4]triazin-2-yl)phenyl)methanol (I-24)

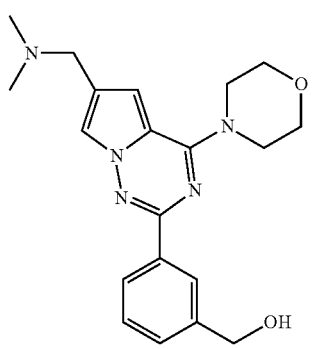

Compound I-24 was prepared by the method which was identical with that for preparing compound 13a, wherein compound 18 (70 mg, 0.184 mmol) was used as the starting material. White solid (100%). m.p. 163-165° C. $^1$H NMR (300 MHz, DMSO-d$_6$): δ 8.20 (s, 1H), 8.11 (dt, J=2.4, 6.0 Hz, 1H), 7.99 (d, J=1.3 Hz, 1H), 7.45-7.41 (m, 2H), 7.15 (d, J=1.3 Hz, 1H), 5.27 (t, J=5.8 Hz, 1H), 4.57 (d, J=5.8 Hz, 2H), 4.07 (t, J=4.6 Hz, 4H), 3.95 (s, 2H), 3.80 (t, J=4.6 Hz, 4H), 2.44 (s, 6H). MS (EI) m/e (%): 367 (M$^+$, 16).

21. Preparation of 3-(6-((dimethylamino)methyl)-4-morpholinopyrrolo[2,1-f][1,2,4]triazin-2-yl)benzyl methanesulfonate (19)

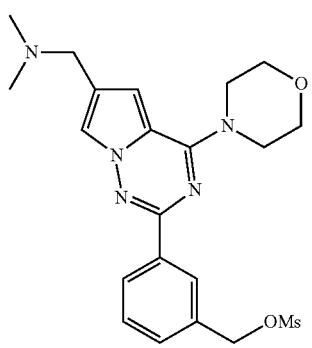 [SMILES: CN(C)Cc1cc2c(N3CCOCC3)nc(-c3cccc(COS(C)(=O)=O)c3)nn2c1]

Compound I-24 (36.7 mg, 0.1 mmol) was dissolved in 5 mL of anhydrous dichloromethane and cooled to 0° C. Methanesulfonyl chloride (14 μL, 0.12 mmol) and triethylamine (16 μL, 0.12 mmol) were added. The reaction was performed at 0° C. for 30 minutes. The reaction mixture was washed successively with saturated sodium bicarbonate solution and water, and the organic layer was dried over anhydrous sodium sulfate, and the solvent was removed under reduced pressure to give 45 mg of white solid (100%). m.p. 178-179° C. NMR (300 MHz, CDCl₃): δ 8.33 (s, 1H), 8.31 (dd, J=1.8, 5.5 Hz, 1H), 7.70 (d, J=1.5 Hz, 1H), 7.51 (d, J=5.5 Hz, 2H), 6.72 (d, J=1.5 Hz, 1H), 5.34 (s, 2H), 4.14 (t, J=4.8 Hz, 4H), 4.04 (s, 2H), 3.91 (t, J=4.8 Hz, 4H), 2.95 (s, 3H), 2.56 (s, 6H). MS (EI) m/e (%): 350 (M-MeSO₃, 30).

22. Preparation of N,N-dimethyl-1-(2-(3-((methylsulfonyl)methyl)phenyl)-4-morpholinopyrrolo[2,1-f][1,2,4]triazin-6-yl)methanamine (I-25)

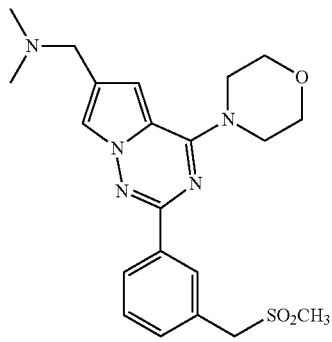 [SMILES: CN(C)Cc1cc2c(N3CCOCC3)nc(-c3cccc(CS(C)(=O)=O)c3)nn2c1]

Compound 19 (45 mg, 0.1 mmol) and sodium methylsulfinate (41 mg, 0.4 mmol) were dissolved in 2 mL N-methylpyrrolidone. The mixture was under microwave irradiation for 30 minutes at 120° C. with the power of 100 watts. After completion of the reaction, the reaction mixture was poured into water, extracted for three times with ethyl acetate, and extracted for three times with dichloromethane. The organic layers were combined and dried over anhydrous sodium sulfate. The solvent was concentrated under reduced pressure to a small volume. The crude product was purified by a preparative plate (dichloromethane:methanol=6:1) to obtain 12 mg of white solid (28.0%). m.p. 143-144° C. ¹H NMR (300 MHz, CDCl₃): δ 8.32 (d, J=5.2 Hz, 1H), 8.29 (s, 1H), 7.63 (d, J=1.2 Hz, 1H), 7.50 (d, J=5.2 Hz, 2H), 6.78 (d, J=1.2 Hz, 1H), 4.34 (s, 2H), 4.11 (t, J=4.4 Hz, 4H), 3.88 (t, J=4.4 Hz, 4H), 3.66 (s, 2H), 2.78 (s, 3H), 2.36 (s, 6H). MS (EI) m/e (%): 429 (M⁺, 12).

23. Preparation of 1-(2-(3-(aminomethyl)phenyl)-4-morpholinopyrrolo[2,1-f][1,2,4]triazin-6-yl)-N,N-dimethylmethanamine (20)

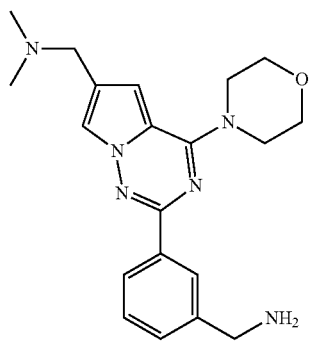

Compound 19 (80 mg, 0.18 mmol) was added to 20 mL of saturated ammonia solution of methanol. The reaction was carried out at 80° C. in a sealed tube for 8 h. After the reaction mixture was concentrated, it was purified by a preparative plate (dichloromethane:methanol=6:1) to obtain 37 mg of colourless oil (56.2%). ¹H NMR (300 MHz, CDCl₃): δ 8.20 (s, 1H), 8.17-8.13 (m, 1H), 7.64 (s, 1H), 7.41-7.39 (m, 2H), 6.86 (s, 1H), 4.11 (t, J=4.7 Hz, 4H), 3.97 (s, 2H), 3.87 (t, J=4.7 Hz, 4H), 3.69 (s, 2H), 2.41 (s, 6H). LC-MS: 367 (M+1).

24. Preparation of N-(3-(6-((dimethylamino)methyl)-4-morpholinopyrrolo[2,1-f][1,2,4]triazin-2-yl)benzyl)methanesulfonamide (I-26)

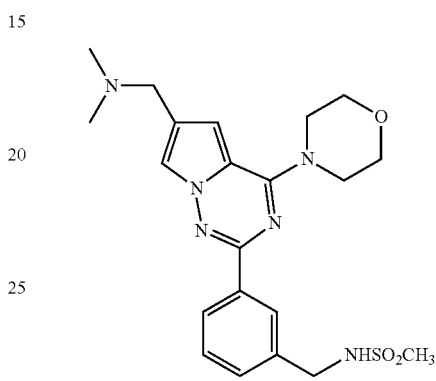

Compound I-26 was prepared by the method which was identical with that for preparing compound 19, wherein compound 20 (37 mg, 0.1 mmol) was used as the starting material. Light yellow solid (12 mg, 26.7%) were obtained by a preparative plate (dichloromethane:methanol=8:1). m.p. 238-240° C. ¹H NMR (300 MHz, CDCl₃): δ 8.20 (s, 1H), 8.19 (d, J=7.1 Hz, 1H), 7.60 (s, 1H), 7.47-7.38 (m, 2 H), 6.88 (s, 1H), 4.41 (s, 2H), 4.02 (br, s, 4H), 3.81 (t, J=4.4 Hz, 4H), 2.95 (s, 2H), 2.94 (s, 3H), 2.87 (s, 1H), 2.51 (s, 6H). MS (EI) m/e (%): 444 (M⁺, 16).

25. Preparation of methyl 4-chloro-2-(6-pivalamido-4-(trifluoromethyl)pyridin-3-yl)pyrrolo[2,1-f][1,2,4]triazine-6-carboxylate (21)

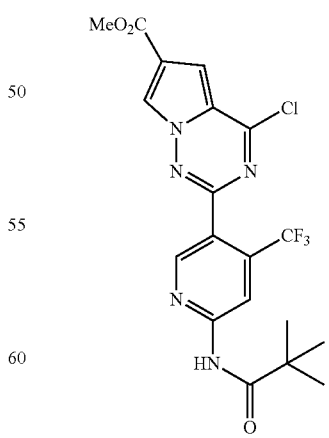

Compound 21 was prepared by the method which was identical with that for preparing compound 8, wherein IIIc (300 mg, 0.686 mmol) was used as the starting material.

Light yellow solid (290 mg, 92.9%). m.p. 172-173° C. $^1$H NMR (300 MHz, CDCl$_3$): δ 8.79 (s, 1H), 8.77 (s, 1H), 8.33 (d, J=1.6 Hz, 1H), 8.30 (s, 1H), 7.47 (d, J=1.6 Hz, 1H), 3.94 (s, 3H), 1.36 (s, 9H). LC-MS: 478 (M+23), 480 (M+2+23).

26. Preparation of Compounds 22

The preparation of compounds 22 was identical with that for compound 9.

Methyl 4-morpholino-2-(6-pivalamido-4-(trifluoromethyl)pyridin-3-yl)pyrrolo[2,1-f][1,2,4]triazine-6-carboxylate (22a)

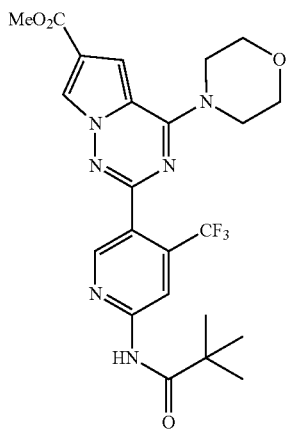 [SMILES: COC(=O)c1cc2c(N3CCOCC3)nc(-c3cnc(NC(=O)C(C)(C)C)cc3C(F)(F)F)nn2c1]

Compound 22a was prepared from 100 mg of compound 21 (0.22 mmol). White solid (73 mg, 65.8%). m.p. 205° C. $^1$H NMR (300 MHz, DMSO-d$_6$): δ 10.53 (s, 1H), 8.79 (s, 1H), 8.57 (s, 1H), 8.30 (d, J=1.2 Hz, 1H), 7.46 (d, J=1.2 Hz, 1H), 4.03 (t, J=4.2 Hz, 4H), 3.83 (s, 3H), 3.75 (t, J=4.2 Hz, 4H), 1.27 (s, 9H). LC-MS: 507 (M+1).

Methyl-4-(8-oxa-3-azabicyclo[3.2.1]octan-3-yl)-2-(6-pivalamido-4-(trifluoromethyl)pyridine e-3-yl)pyrrolo[2,1-f][1,2,4]triazine-6-carboxylate (22b)

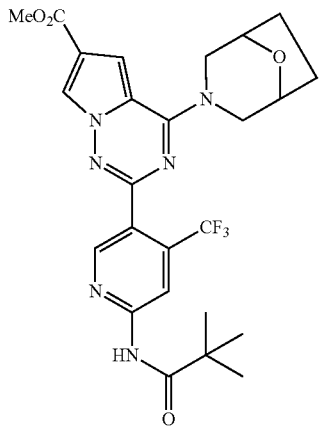 [SMILES: COC(=O)c1cc2c(N3CC4CCC(C3)O4)nc(-c3cnc(NC(=O)C(C)(C)C)cc3C(F)(F)F)nn2c1]

Compound 22b was prepared from 276 mg of compound 21 (0.61 mmol). Light yellow solid (274 mg, 84.8%). m.p. 175-176° C. $^1$H NMR (300 MHz, CDCl$_3$): δ 8.71 (s, 1H), 8.70 (s, 1H), 8.27 (s, 1H), 8.09 (s, 1H), 7.21 (s, 1H), 4.52 (br s, 4H), 3.90 (s, 3H), 3.54 (br s, 2H), 2.04-1.99 (m, 2H), 1.89-1.78 (m, 2H), 1.36 (s, 9H). LC-MS: 533 (M+1).

(S)-methyl 4-(3-methylmorpholino)-2-(6-pivalamido-4-(trifluoromethyl)pyridin-3-yl) pyrrolo[2,1-f][1,2,4]triazine-6-carboxylate (22c)

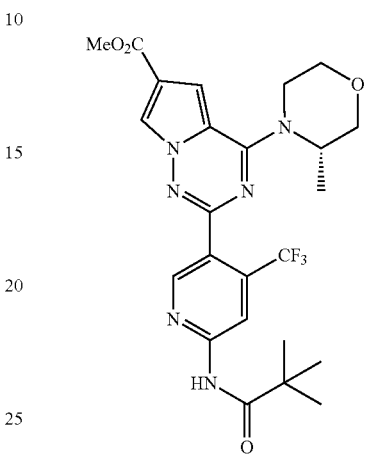

Compound 22c was prepared from 210 mg of compound 21 (0.46 mmol). Light yellow solid (145 mg, 60.4%). m.p. 225-226° C. $^1$H NMR (300 MHz, DMSO-d$_6$): δ 10.53 (s, 1H), 8.79 (s, 1H), 8.57 (s, 1H), 8.29 (d, J=1.5 Hz, 1H), 7.42 (s, 1H), 4.92 (br, 1H), 4.61 (br, 1H), 4.03-3.96 (m, 1H), 3.83 (s, 3H), 3.81-3.64 (m, 3H), 3.53 (t, J=11.4 Hz, 1H), 1.43-1.31 (m, 3H), 1.27 (s, 9H). LC-MS: 521 (M+1).

27. Preparation of Compounds 23

2-(6-amino-4-(trifluoromethyl)pyridin-3-yl)-4-morpholinopyrrolo[2,1-f][1,2,4]triazine-6-carboxylic acid (23a)

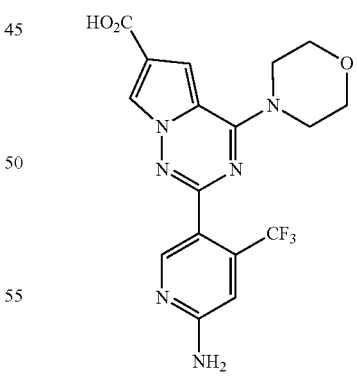

Compound 22a (300 mg, 0.59 mmol) was suspended in 10 mL of ethanol. 1.5 mL of 2 M potassium hydroxide solution was added and refluxed for 1 hour. The reaction is substantially completed. 2 mL of acetic acid was added. Most of the solvent was distilled off under reduced pressure to precipitate solids. The precipitated solids were filtered to give compound 23a. White solid (224 mg, 92.6%). m.p. 244-245° C. $^1$H NMR (300 MHz, DMSO-d$_6$): δ 12.54 (s, 1H), 8.37 (s, 1H), 8.11 (s, 1H), 7.34 (s, 1H), 6.83 (s, 3H), 4.00 (t, J=4.0 Hz, 4H), 3.73 (t, J=4.0 Hz, 4H). LC-MS: 409 (M+1).

2-(6-amino-4-(trifluoromethyl)pyridin-3-yl)-4-(8-oxa-3-azabicyclo[3.2.1]octan-3-yl)pyrrolo[2,1-f][1,2,4]triazine-6-carboxylic acid (23b)

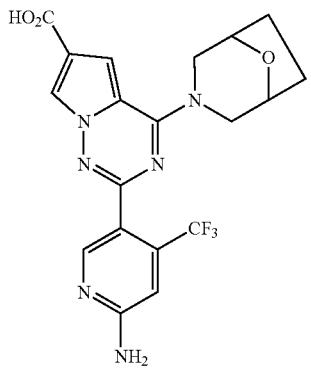 [SMILES: Nc1cc(C(F)(F)F)c(-c2nc(N3CC4CCC(C3)O4)c3cc(C(=O)O)cn3n2)cn1]

Compound 23b was prepared by the method which was identical with that for preparing compound 23a, wherein compound 22b (250 mg, 0.45 mmol) was used as the starting material. White solid (102 mg, 51.9%). m.p. 284-285° C. $^1$H NMR (300 MHz, DMSO-d$_6$): δ 12.44 (br s, 1H), 8.36 (s, 1H), 8.11 (s, 1H), 7.30 (s, 1H), 6.82 (s, 3H), 4.47 (br s, 2H), 4.42 (br s, 2H), 3.32 (br s, 2H), 1.87-1.84 (m, 2H), 1.75-1.68 (m, 2H). LC-MS: 435 (M+1).

(S)-2-(6-amino-4-(trifluoromethyl)pyridin-3-yl)-4-(3-methylmorpholino)pyrrolo[2,1-f][1,2,4]triazine-6-carboxylic acid (23c)

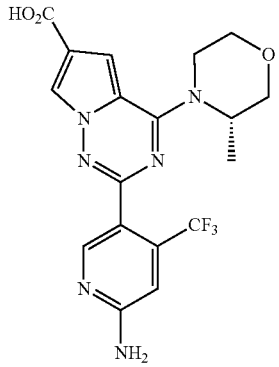 [SMILES: C[C@H]1COCCN1c1nc(-c2cnc(N)cc2C(F)(F)F)nn2cc(C(=O)O)cc12]

Compound 23c was prepared by the method which was identical with that for preparing compound 23a, wherein compound 22c (1.8 g, 3.46 mmol) was used as the starting material. White solid (1.33 g, 91.2%). m.p.>300° C. $^1$H NMR (400 MHz, DMSO-d$_6$): δ 12.76 (s, 1H), 8.36 (s, 1H), 8.11 (d, J=1.3 Hz, 1H), 7.30 (s, 1H), 6.85 (s, 2H), 6.82 (s, 1H), 4.89 (br, 1H), 4.52 (br, 1H), 3.97 (d, J=8.2 Hz, 1H), 3.76-3.63 (m, 2H), 3.51 (t, J=10.7 Hz, 2H), 1.36 (s, 3H). LC-MS: 423 (M+1).

28. Preparation of Compounds 24

The preparation of compounds 24 were identical with that for compound 12.

(2-(6-amino-4-(trifluoromethyl)pyridin-3-yl)-4-morpholinopyrrolo[2,1-f][1,2,4]triazin-6-yl)(4-(methylsulfonyl)piperazin-1-yl)methanone (24a)

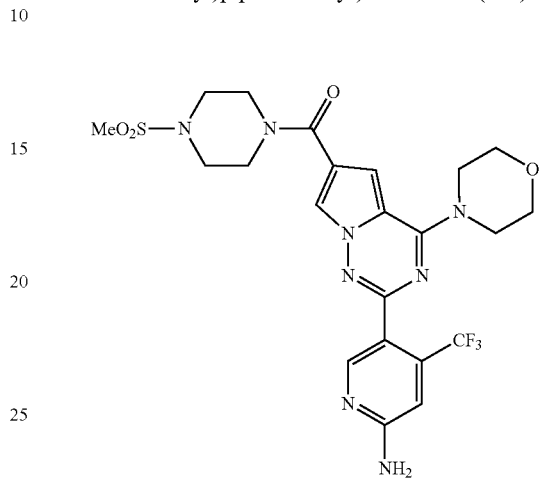

Compound 24a was prepared from 220 mg of compound 23a (0.54 mmol). White solid (253 mg, 84.7%). m.p. 197-198° C. $^1$H NMR (300 MHz, DMSO-d$_6$): δ 8.36 (s, 1H), 8.04 (s, 1H), 7.18 (s, 1H), 6.83 (s, 3H), 4.04-3.92 (m, 4H), 3.73 (br s, 8H), 3.20-3.11 (m, 4H), 2.91 (s, 3H). MS (EI) m/e (%): 554 (68, M$^+$).

(2-(6-amino-4-(trifluoromethyl)pyridin-3-yl)-4-(8-oxa-3-azabicyclo[3.2.1]octan-3-yl)pyrrolo[2,1-f][1,2,4]triazin-6-yl)(4-(methylsulfonyl)piperazin-1-yl)methanone (24b)

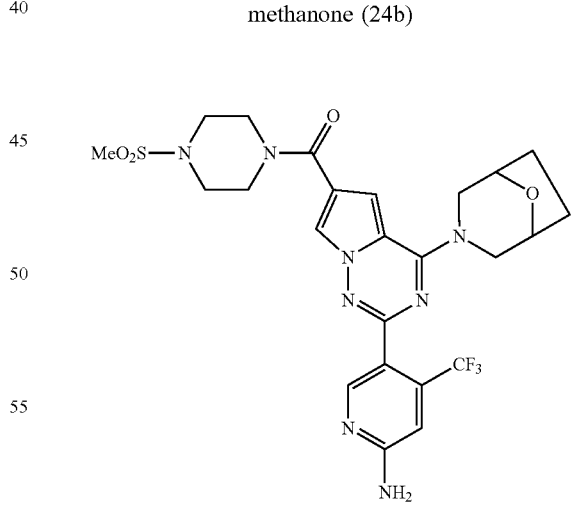

Compound 24b was prepared from 90 mg of compound 23b (0.21 mmol). White solid (113 mg, 93.8%). m.p. 175° C. $^1$H NMR (300 MHz, CDCl$_3$): δ 8.52 (s, 1H), 7.77 (d, J=1.7 Hz, 1H), 6.96 (d, J=1.7 Hz, 1H), 6.81 (s, 1H), 4.86 (s, 2H), 4.49 (br s, 4H), 3.91 (t, J=4.6 Hz, 4H), 3.55 (br s, 2H), 3.28 (t, J=4.6 Hz, 4H), 2.81 (s, 3H), 2.04-1.95 (m, 2H), 1.89-1.79 (m, 2H). LC-MS: 581 (4+1).

(S)-2-(6-amino-4-(trifluoromethyl)pyridin-3-yl)-4-(3-methylmorpholino)pyrrolo[2,1-f][1,2,4]triazin-6-yl)(4-(methylsulfonyl)piperazin-1-yl)methanone (24c)

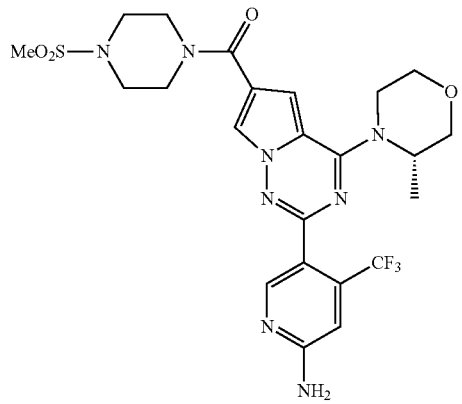 [SMILES: C[C@H]1COCCN1c1nc(-c2cnc(N)cc2C(F)(F)F)nn2cc(C(=O)N3CCN(S(C)(=O)=O)CC3)cc12]

Compound 24c was prepared from 2.42 g of compound 23c (4.86 mmol) as the starting material. Light yellow solid (3 g, 92.2%). m.p. 200-202° C. $^1$H NMR (300 MHz, CDCl$_3$): δ 8.52 (s, 1H), 7.78 (d, J=1.7 Hz, 1H), 6.97 (d, J=1.7 Hz, 1H), 6.81 (s, 1H), 4.90 (s, 3H), 4.81-4.40 (m, 1H), 4.03 (d, J=7.4 Hz, 1H), 3.91 (t, J=4.8 Hz, 4H), 3.83-3.72 (m, 2H), 3.66-3.56 (m, 2H), 3.28 (t, J=4.8 Hz, 4H), 2.81 (s, 3H), 1.48 (d, J=6.2 Hz, 3H). LC-MS: 569 (M+1).

29. Preparation of 5-(6-((4-(methylsulfonyl)piperazin-1-yl)methyl)-4-morpholinopyrrolo[2,1-f][1,2,4]triazin-2-yl)-4-(trifluoromethyl)pyridin-2-amine (I-27)

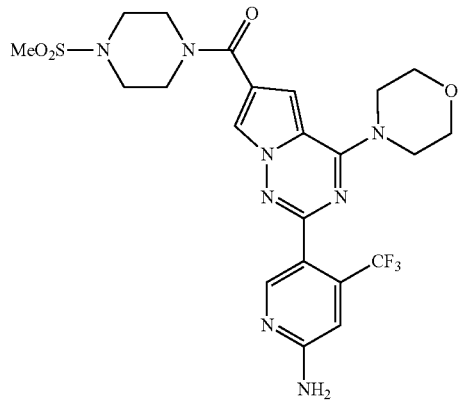 [SMILES: CS(=O)(=O)N1CCN(C(=O)c2cc3c(N4CCOCC4)nc(-c4cnc(N)cc4C(F)(F)F)nn3c2)CC1]

Compound I-27 was prepared from 200 mg of compound 24a (0.36 mmol) as the starting material. The preparation process was similar to that of compound 13. A preparative plate (dichloromethane:methanol=20:1) was used for purification. Light yellow solid (43 mg, 22.0%). m.p. 122-123° C. $^1$H NMR (300 MHz, CDCl$_3$): δ 8.51 (s, 1H), 7.59 (s, 1H), 6.80 (s, 1H), 6.67 (s, 1H), 4.89 (s, 2H), 4.04 (t, J=4.4 Hz, 4H), 3.82 (t, J=4.4 Hz, 4H), 3.64 (s, 2H), 3.27 (br s, 4H), 2.78 (s, 3H), 2.62 (br s, 4H). MS (EI) m/e (%): 540 (M$^+$, 5).

30. Preparation of 1-(4-fluorophenyl)-3-(5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)urea (I-28)

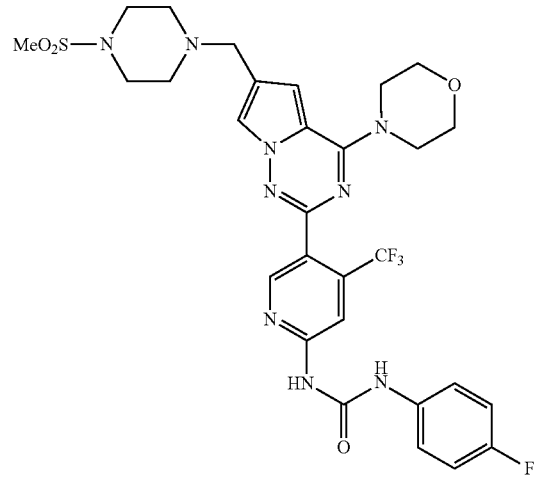 [SMILES: CS(=O)(=O)N1CCN(Cc2cc3c(N4CCOCC4)nc(-c4cnc(NC(=O)Nc5ccc(F)cc5)cc4C(F)(F)F)nn3c2)CC1]

I-28 was prepared from 30 mg I-27 (0.055 mmol) as the starting material. The preparation process was the same as the synthesis of compound I-1. A preparative plate (dichloromethane:methanol=10:1) was used for purification. White solid (7 mg, 18.6%). m.p. 204-205° C. NMR (300 MHz, CDCl$_3$): δ 11.38 (s, 1H), 9.37 (s, 1H), 8.75 (s, 1H), 7.62 (s, 1H), 7.57 (dd, J=8.5, 4.4 Hz, 2H), 7.33 (s, 1H), 7.06 (t, J=8.5 Hz, 2H), 6.72 (s, 1H), 4.10-4.01 (m, 4H), 3.89-3.81 (m, 4H), 3.67 (s, 2H), 3.30 (br s, 4H), 2.79 (s, 3H), 2.64 (br s, 4H). ESI-MS: 678 (M+1).

31. Preparation of 5-(4-(8-oxa-3-azabicyclo[3.2.1]octan-3-yl)-6-((4-(methylsulfonyl)piperazin-1-yl)methyl)pyrrolo[2,1-f][1,2,4]triazin-2-yl)-4-(trifluoromethyl)pyridin-2-amine (I-29)

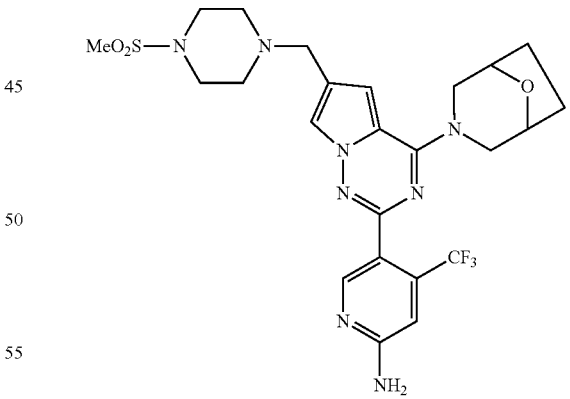

I-29 was prepared from 100 mg of compound 24b (0.17 mmol). The preparation process was the same as that of compound 13. A preparative plate (dichloromethane:methanol=20:1) was used for purification. White solid (17 mg, 17.4%). m.p. 138° C. $^1$H NMR (300 MHz, CDCl$_3$): δ 8.50 (s, 1H), 7.57 (d, J=1.2 Hz, 1H), 6.79 (s, 1H), 6.63 (d, J=1.2 Hz, 1H), 4.92 (s, 2H), 4.48 (br s, 4H), 3.61 (s, 2H), 3.52 (br s, 1H), 3.47 (br s, 1H), 3.26 (t, J=4.8 Hz, 4H), 2.77 (s, 3H), 2.60 (t, J=4.8 Hz, 4H), 2.00-1.96 (m, 2H), 1.89-1.79 (m, 2H). MS (EI) m/e (%): 566 (M$^+$, 5).

32. Preparation of 1-ethyl-3-(5-(6-((4-(methylsulfonyl)piperazin-1-yl)methyl)-4-morpholino pyrrolo[21-f][1,2,4]triazin-2-yl)-4-(trifluoromethyl)pyridin-2-yl)urea (I-30)

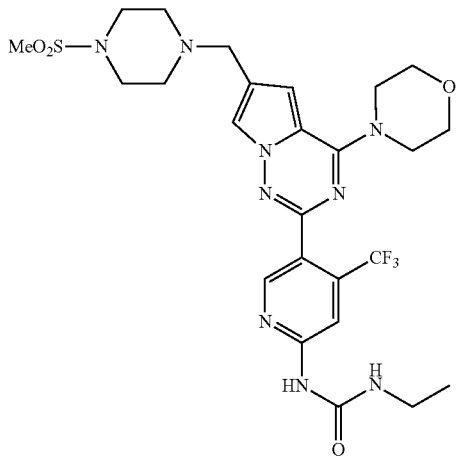 [SMILES: CCNC(=O)Nc1cc(C(F)(F)F)c(-c2nc(N3CCOCC3)c3cc(CN4CCN(S(C)(=O)=O)CC4)cn3n2)cn1]

Ethyl isocyanate (85 mg, 1.2 mmol) was added to the solution of I-27 (110 mg, 0.2 mmol) and 1,8-diazacyclo[5.4.0]undec-7-ene (DBU, 183 mg, 1.2 mmol) in dichloromethane and stirred for two days at room temperature. Diethyl ether was used for recrystallization and 74 mg (60.5%) of white solid was obtained. m.p. 208° C. (decomposition). $^1$H NMR (300 MHz, DMSO-$d_6$): δ 9.99 (br s, 1H), 8.62 (s, 1H), 8.18 (s, 1H), 7.78 (br s, 1H), 7.73 (s, 1H), 6.95 (s, 1H), 3.98 (br s, 4H), 3.73 (br s, 4H), 3.59 (s, 2H), 3.33 (br s, 2H), 3.16 (q, J=7.5 Hz, 2H), 3.11 (br s, 4H), 2.86 (s, 3H), 1.62 (br s, 2H), 1.09 (t J=7.5 Hz, 3H). LC-MS: 612 (M+1).

33. Preparation of Compounds (I-31~I-33)

General preparation method: To the solution of I-27 (54 mg, 0.1 mmol) and triethylamine (101 mg, 1 mmol) in chloroform was added the corresponding chloroformate (0.3 mmol). The reaction mixture was stirred at room temperature for four days. The crude product was purified by column chromatography with dichloromethane/methanol (10:1).

Phenyl (5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)carbamate (I-31)

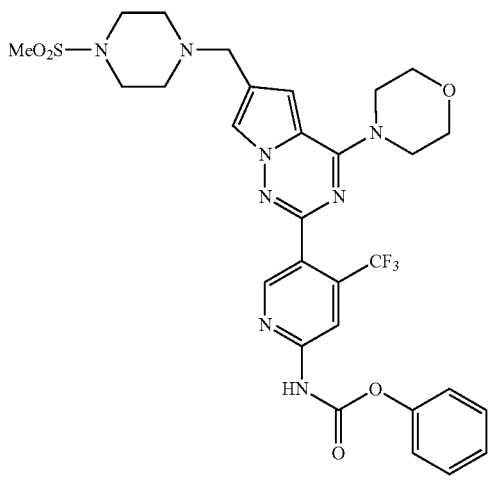 [SMILES: CS(=O)(=O)N1CCN(Cc2cc3c(N4CCOCC4)nc(-c4cnc(NC(=O)Oc5ccccc5)cc4C(F)(F)F)nn3c2)CC1]

Light yellow solid. Yield 37.1%. m.p. 108-110° C. $^1$H NMR (300 MHz, DMSO-$d_6$): δ 11.42 (s, 1H), 8.79 (s, 1H), 8.27 (s, 1H), 7.76 (s, 1H), 7.49-7.44 (m, 2H), 7.32-7.27 (m, 3H), 6.98 (s, 1H), 3.99 (br s, 4H), 3.74 (br s, 4H), 3.60 (s, 2H), 3.31 (br s, 4H), 3.12 (br s, 4H), 2.87 (s, 3H). LC-MS: 661 (M+1).

Ethyl (5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)carbamate (I-32)

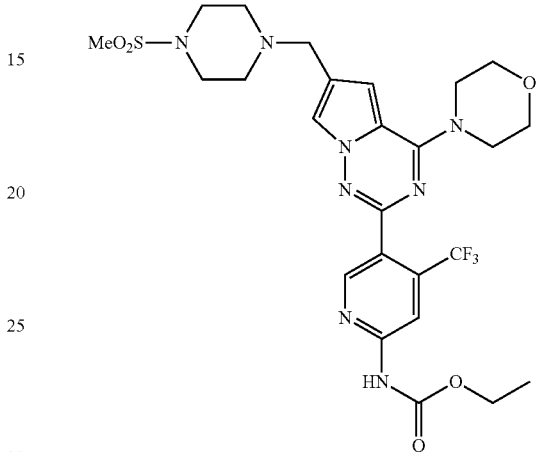

White solid. Yield 50.7%. m.p. 211-213° C. $^1$H NMR (300 MHz, CDCl$_3$): δ 8.71 (s, 1H), 8.41 (s, 1H), 7.92 (s, 1H), 7.60 (s, 1H), 6.67 (s, 1H), 4.30 (q, J=7.2 Hz, 2H), 4.05 (t, J=4.5 Hz, 4H), 3.83 (t, J=4.5 Hz, 4H), 3.63 (s, 2H), 3.26 (br s, 4H), 2.78 (s, 3H), 2.61 (br s, 4H), 1.36 (t, J=7.2 Hz, 3H). LC-MS: 613 (M+1).

Methyl(5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)carbamate (I-33)

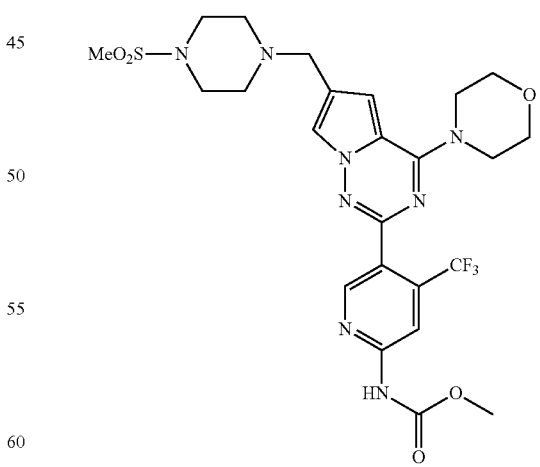

White solid (43.4%). m.p. 212-214° C. $^1$H NMR (300 MHz, CDCl$_3$): δ 8.70 (s, 1H), 8.40 (s, 1H), 7. 60 (d, J=1.5 Hz, 1H), 6.67 (s, 1H), 4.05 (t, J=4.5 Hz, 4H), 3.85 (s, 3H), 3.83 (t, J=4.5 Hz, 4H), 3.63 (s, 2H), 3.27 (br s, 4H), 2.78 (s, 3H), 2.61 (br s, 4H). LC-MS: 599 (M+1).

34. Preparation of (S)-5-(4-(3-methylmorpholino)-6-((4-(methylsulfonyl)piperazin-1-yl)methyl)pyrrolo[2,1-f][1,2,4]triazin-2-yl)-4-(trifluoromethyl)pyridin-2-amine (I-34)

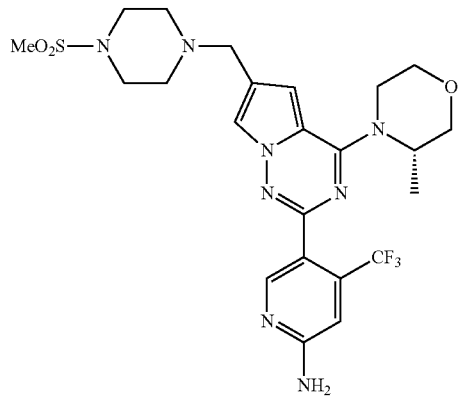 [SMILES: C[C@H]1COCCN1c1nc(-c2cnc(N)cc2C(F)(F)F)nn2cc(CN3CCN(S(C)(=O)=O)CC3)cc12]

At −40° C., 1 M borane-THF (80 mL) was added dropwise to the solution of compound 24c (1.8 g, 3.17 mmol) in 50 mL of tetrahydrofuran. After the reaction proceeded 0.5 hours at this temperature, the reaction system was refluxed for 2 hours, and then cooled to below 0° C. 100 mL of concentrated hydrochloric acid was added dropwise and afterwards refluxed for 1 hour. When most of hydrochloric acid was removed by rotation evaporation, the pH of the solution was adjusted to about 8 by using saturated sodium carbonate solution. After extracted for three times with ethyl acetate, the organic phase was dried over anhydrous sodium sulfate, and the solvent was removed under reduced pressure to give the crude product. The crude product was purified by column chromatography with dichloromethane/methanol (40:1) to afford white solid (56.9%). m.p. 262° C. $^1$H NMR (300 MHz, DMSO-d6): δ 8.34 (s, 1H), 7.68 (s, 1H), 6.88 (s, 1H), 6.82 (s, 1H), 6.77 (s, 2H), 4.87 (br s, 1H), 4.47 (br s, 1H), 3.96 (br s, 1H), 3.77-3.41 (m, 8H), 3.11 (s, 6H), 2.87 (s, 3H), 1.32 (s, 3H). LC-MS: 555 (M+1).

35. Preparation of (S)-methyl(5-(4-(3-methylmorpholino)-6-((4-(methylsulfonyl)piperazin-1-yl)methyl)pyrrolo[2,1-f][1,2,4]triazin-2-yl)-4-(trifluoromethyl)pyridin-2-yl)carbamate (I-35)

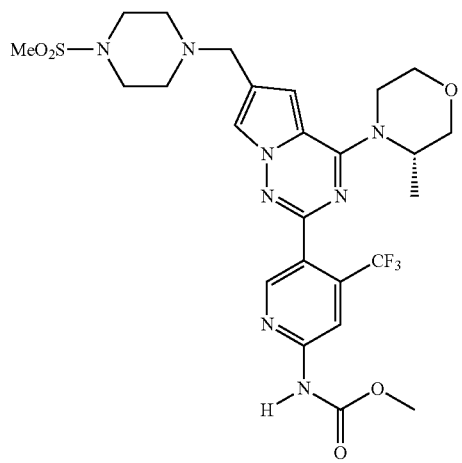 [SMILES: COC(=O)Nc1cc(C(F)(F)F)c(-c2nc(N3CCOC[C@@H]3C)c3cc(CN4CCN(S(C)(=O)=O)CC4)cn3n2)cn1]

At −40 methyl chloroformate (28.85 mmol) was added to the solution of I-34 (880 mg, 1.44 mmol) and triethylamine (1.5 g, 14.4 mmol) in chloroform and stirred for 2 h. The rude product was purified by column chromatography with dichloromethane/methanol (60:1) to afford white solid (44.2%). m.p. 150-152° C. $^1$H NMR (400 MHz, CDCl$_3$): δ 8.70 (s, 1H), 8.41 (s, 1H), 8.22 (s, 1H), 7.60 (s, 1H), 6.67 (s, 1H), 4.92 (br s, 1H), 4.56 (br s, 1H), 4.03 (d, J=7.9 Hz, 1H), 4.00-3.52 (m, 9H), 3.27 (s, 4H), 2.78 (s, 3H), 2.62 (s, 4H), 1.47 (d, J=6.6 Hz, 3H). LC-MS: 613 (M+1).

36. Preparation of (S)-1-ethyl-3-(5-(4-(3-methylmorpholino)-6-((4-(methylsulfonyl) piperazin-1-yl)methyl)pyrrolo[2,1-f][1,2,4]triazin-2-yl)-4-(trifluoromethyl)pyridin-2-yl)urea (I-36)

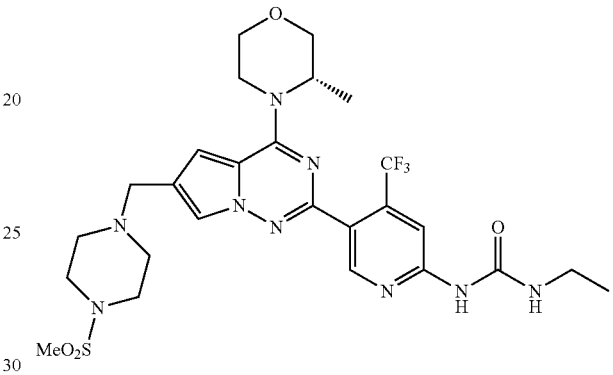

Compound I-36 was prepared by the same preparation method as that of compound I-30. White solid, $^1$H NMR (300 MHz, CDCl$_3$) δ 9.45 (s, 1H), 9.01 (br s, 1H), 8.63 (s, 1H), 7.59 (s, 1H), 7.30 (s, 1H), 6.67 (s, 1H), 4.93 (br s, 1H), 4.56 (br s, 1H), 4.03 (d, J=7.5 Hz, 1H), 3.89-3.69 (m, 2H), 3.64 (s, 2H), 3.44 (q, J=6.9 Hz, 2H), 3.39-3.11 (m, 6H), 2.78 (s, 3H), 2.62 (s, 4H), 1.47 (d, J=6.7 Hz, 3H), 1.26 (t, J=7.2 Hz, 3H).

37. 1-Ethyl-3-(5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)urea mesylate

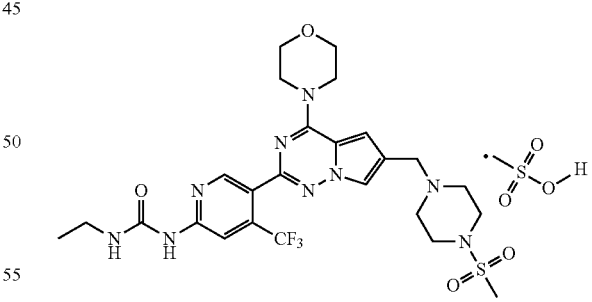

5% solution of methane sulfonic acid in tetrahydrofuran (600 μL, 0.47 mmol) was added to the solution of I-30 (220 mg, 0.36 mmol) in 10 mL chloroform and stirred for 1 h at room temperature. The pure product was obtained by filtration. White powder (99.0%). m.p. 220° C. (decomposition). $^1$H NMR (300 MHz, DMSO-d6): δ 9.83 (br s, 1H), 9.63 (s, 1H), 8.63 (s, 1H), 8.12 (s, 1H), 7.94 (s, 1H), 7.37 (s, 1H), 7.17 (s, 1H), 4.43 (s, 2H), 4.01 (s, 4H), 3.75 (s, 6H), 3.50 (s, 2H), 3.28-3.01 (m, 6H), 3.0 (s, 3H), 2.32 (s, 3H), 1.08 (t, J=7.2 Hz, 3H). $^{13}$C NMR (126 MHz, DMSO) δ 155.03, 154.57, 153.91, 153.00, 150.65, 136.78 (q, J=32.1 Hz, CF$_3$C), 123.24 (q, J=274.8 Hz, CFA 123.51, 121.78, 113.99, 113.09, 108.30 (q, J=5.2 Hz, CF$_3$CCH), 107.81, 66.37, 52.23, 50.49, 46.00, 42.93, 35.55, 34.45, 15.67, 15.67.

38. Methyl(5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)carbamate mesylate

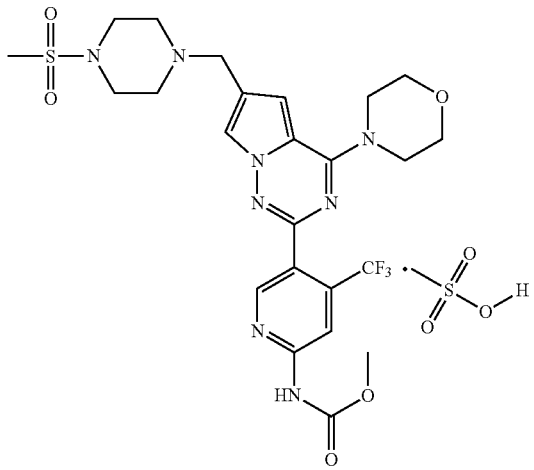

5% solution of methane sulfonic acid in tetrahydrofuran (978 μL, 0.77 mmol) was added to the solution of I-33 (300 mg, 0.50 mmol) in 15 mL of tetrahydrofuran and stirred for 5 h at room temperature. Diehtyl ether was added to the system until a plenty of solids precipitated. The pure product was obtained by filtration. White solid (100%). m.p. 240° C. (decomposition). $^1$H NMR (300 MHz, DMSO-d6): δ 10.94 (s, 1 H), 9.82 (s, 1 H), 8.74 (s, 1 H), 8.32 (s, 1 H), 7.99 (s, 1H), 7.19 (s, 1 H), 4.46 (s, 2 H), 4.03 (t, J=4.8 Hz, 4 H), 3.78 (t, J=4.8 Hz, 4H), 3.75 (s, 3 H), 3.67-3.43 (m, 4H), 3.27-3.05 (m, 4 H), 3.02 (s, 3 H), 2.33 (s, 3 H). $^{13}$C NMR (126 MHz, DMSO-d6): δ 154.58, 154.16, 153.88, 152.90, 151.07, 137.029 (q, J=31 Hz, CF$_3$C), 125.19, 123.23 (q, J=274.9 Hz, CF$_3$), 121.84, 113.99, 113.07, 108.60 (q, J=5 Hz, CF$_3$CH), 107.88, 66.35, 52.78, 52.22, 50.49, 46.03, 42.95, 35.57, 25.59.

39. (S)-methyl(5-(4-(3-methylmorpholino)-6-((4-(methylsulfonyl)piperazin-1-yl)methyl)pyrrolo[2,1-f][1,2,4]triazin-2-yl)-4-(trifluoromethyl)pyridin-2-yl)carbamate mesylate

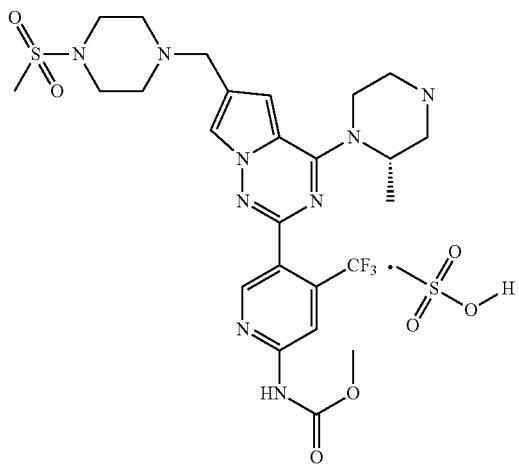

5% solution of methane sulfonic acid in tetrahydrofuran (589 μL, 0.46 mmol) was added to the solution of I-35 (231 mg, 0.38 mmol) in 15 mL tetrahydrofuran and stirred for 3 h at room temperature. Tetrahydrofuran was removed under the reduced pressure to give a jelly. A small amount of methanol was added to dissolve the jelly. And then diethyl ether was added dropwise until solid precipitated. The pure product was obtained by filtration. White powder (80.72%). m.p. 210° C. (decomposition). $^1$H NMR (300 MHz, DMSO-d6): δ 10.91 (s, 1H), 9.86 (s, 1H), 8.73 (s, 1H), 8.31 (s, 1H), 7.98 (s, 1H), 7.17 (s, 1H), 4.90 (br s, 1H), 4.45 (br s, 3H), 4.00 (d, J=7.9 Hz, 1H), 3.88-3.61 (m, 7H), 3.53 (s, 4H), 3.15 (br s, 4H), 3.01 (s, 3H), 2.41-2.26 (m, 3H), 1.39 (br s, 3H). $^{13}$C NMR (126 MHz, DMSO-d6): δ 154.60, 154.15, 153.68, 152.96, 151.09, 136.91 (q, J=32.5 Hz, CF$_3$C), 125.26, 123.24 (q, J=274.9 Hz, CF$_3$) 121.89, 114.05, 113.09, 108.60 (q, J=5.5 Hz, CF$_3$CH) 107.95, 70.51, 66.46, 52.78, 52.20, 50.48, 42.93, 35.58, 31.17, 13.19.

Biological Activity Test

Inhibition on PI3Kα Kinase Activity

Experimental Method

The activity of purified kinase was detected with Kinase-Glo® Plus kinase luminescent assay by measuring the amount of the remaining Kinase in the solution after the kinase reaction was completed. Kinase reaction was performed in a 384-well white plate (Greiner), 1 μL of tested compound or control DMSO was added into each well containing 5 reaction buffer [10 mM Tris-HCl pH 7.5, 50 mM NaCl, 3 mM MgCl$_2$, 1 mM DTT (dithiothreitol) 0.05% CHAPS (3-[(3-Cholamidopropyl)dimethylammonio]-1-propanesulfonate, 3-(3-cholaminopropyl)-dimethylamino-1-propanesulfonic acid), and the reaction buffer was supplemented with 12 μM of substrate, D-myo-Phosphatidylinositol-4,5-bisphosphate (4,5-phosphatidyl inositol diphosphate) and 2 μM ATP (adenosine triphosphate). And then 4 μL reaction buffer containing 62.5 nM PI3Kα or non-PI3Kα control was added to initiate the kinase reaction. After reaction was performed for 1 hour at room temperature, 10 μL of Kinase Glo-Plus mixture was added and incubated for 1 hour to quench the reaction. The chemiluminescence value was detected with EnVision 2104 multifunctional microplate reader (Perkinelmer).

Experimental Results

The experimental results (table 2) showed that the inhibitory activities of the following seven compounds of the present invention on PI3Kα were comparable to or more potent than that of PI-103. And they were I-22 (9.59 nM), I-27 (8.37 nM), I-28 (9.30 nM), I-30 (8.19 nM), I-32 (7.15 nM), I-33 (2.84 nM), and I-35 (5.67 nM), respectively.

TABLE 2

IC$_{50}$ of pyrrolo[2,1-f][1,2,4]triazine compounds on PI3α

| Compound No. | X | R$_1$ | R$_2$ | R$_3$ | R$_4$ | IC$_{50}$ (nM) |
|---|---|---|---|---|---|---|
| PI-103 | | | | | | 9.79 |
| I-22 | C | MeO$_2$S—N(piperazine)— | H | t-Bu-NH-C(O)-NH-(4-phenyl)-C(O)-N(piperazine)-N-Me | —N(morpholine) | 9.59 |
| I-27 | N | MeO$_2$S—N(piperazine)— | CF$_3$ | NH$_2$ | —N(morpholine) | 8.37 |
| I-28 | N | MeO$_2$S—N(piperazine)— | CF$_3$ | 4-FPhNHCONH | —N(morpholine) | 9.30 |
| I-30 | N | MeO$_2$S—N(piperazine)— | CF$_3$ | EtNHCONH | —N(morpholine) | 8.19 |
| I-32 | N | MeO$_2$S—N(piperazine)— | CF$_3$ | EtOCONH | —N(morpholine) | 7.15 |
| I-33 | N | MeO$_2$S—N(piperazine)— | CF$_3$ | MeOCONH | —N(morpholine) | 2.84 |
| I-35 | N | MeO$_2$S—N(piperazine)— | CF$_3$ | MeOCONH | —N(3-methylmorpholine, stereo) | 5.67 |

The Inhibitory Activity on the Proliferation of Human Rhabdomyosarcoma Rh30 Cells Rh30 cells were seeded in a 96-well plate at 3000 cells/well. After the cells adhered, tested compounds at concentration of 10, 3, 1, 0.3, or 0.1 μM were added, and incubated for 72 h. The culture media were discarded and cells were fixed with trichloroacetic acid. After washed with distilled water for five times and dried, sulfonylrhodamine B was added. After washed with 1% glacial acetic acid for five times and dried, trihydroxymethylaminomethane buffer was added. OD value was measured by using a microplate reader at a wavelength of 560 nm. The inhibitory rate was calculated and the results were shown in table 3. The above results showed that compounds of the present invention display potent inhibitory activity on Rh30 cell proliferation, wherein the IC$_{50}$ values of I-24, I-25 and I-28 even reached tens of nanomolar.

TABLE 3

IC$_{50}$s of pyrrolo[2,1-f][1,2,4]triazine compounds against proliferation of Rh30 cells

| | Compound | | | | | | | |
|---|---|---|---|---|---|---|---|---|
| | I-4 | I-5 | I-6 | I-9 | I-14 | I-22 | I-24 | I-25 | I-26 |
| IC50 (μM) | 0.4 | 1.24 | 1.36 | 0.99 | 0.5 | 0.54 | 0.074 | 0.039 | 0.24 |

TABLE 3-continued

IC$_{50}$s of pyrrolo[2,1-f][1,2,4]triazine compounds against proliferation of Rh30 cells

| | Compound | | | | | | |
|---|---|---|---|---|---|---|---|
| | I-27 | I-28 | I-29 | I-30 | I-31 | I-33 | I-34 | I-35 |
| IC50 (μM) | 0.73 | 0.074 | 3.42 | 0.82 | 5.06 | 2.52 | 0.53 | 0.47 |

The Effects of I-33 on PI3K Signaling in Human Rhabdomyosarcoma Rh30 Cells and Human Glioma U87MG Cells Experimental Method Rh30 and U87MG cells were seeded in 12-well plates at $2\times10^5$ cells/well. On the next day, cells were incubated in fresh serum-free culture media subjected to starvation for 24 hours. Cells were then treated with different concentrations of compound I-33 for 1 h. After stimulated with IGF-1 for 10 minutes, the lysed cells were collected, and 4×SDS loading buffer [200 mM Tris.Cl (pH 6.8), 400 mM DTT, 8% SDS (sodium dodecyl sulfate), 0.4% bromophenol blue, 40% glycerol] was added. The cell lysates were boiled for 10 minutes. Aliquot was loaded on polyacrylamide gel and electrophoresis was performed in Tris-glycine electrophoresis buffer (25 mM Tris, 250 mM glycine, 0.1% SDS) at 80-100 V for 2-2.5 hours. The proteins were transformed from gel to nitrocellulose filter membrane by using semidry method. The filter membrane was blocked with blocking solution containing 5% skim milk powder (5% skim milk powder, 20 mM Tris-HCl (pH 7.2-7.4), 150 mM NaCl, 0.1% (v/v) Tween20) in a shaker at room temperature for 2 hours. Then specific primary antibody was added and hybridized at 4° C. overnight. The membrane was washed by washing buffer [20 mM Tris-HCl (pH 7.2-7.4), 150 mM NaCl, 0.1% (v/v) Tween20] for three times at room temperature, 15 minutes each time. A horseradish peroxidase-labeled secondary antibody was added, and the system was placed on a shaker and gently shaken at room temperature for 1 hour. After washed with washing buffer for three times, the membrane was incubated with SuperSignal West Dura Chemiluminescent Substrate (Pierce Inc, Rochford, Ill.). And then the membrane was exposed, developed, and fixed, and pictures were taken.

Experimental Results

The experimental results (FIG. 1) showed that I-33 significantly inhibited the transduction of PI3K signaling in human rhabdomyosarcoma Rh30 cells and human glioma U87MG cells.

Inhibitory Activity of I-30 and I-33 on the Proliferation of Human Cancer Cells from Various Tissues I-30 and I-33 were selected to test their activity on the proliferation of human cancer cells originated from different tissue types. The results were shown in table 4.

TABLE 4

The inhibitory activity of I-30 and I-33 on a panel of human cancer cells

| | Compound | | |
|---|---|---|---|
| Cell line | GDC0941 (μM) | I-33 (μM) | I-30 (μM) |
| B-BT474 | 0.256 | 0.062 | 0.032 |
| B-MCF-7 | 0.519 | — | 2.51 |
| C-HCT-116 | 8.1 | 10 | 9.7 |
| C-LOVO | 0.517 | 1.33 | 0.493 |
| E-RL95-2 | 2.2 | 5.3 | 2 |
| G-MKN-45 | 1.67 | 3.4 | 1.55 |
| L-BEL-7402 | 3.2 | 4.9 | 3.2 |
| LG-NCI-H23 | 1.2 | 0.73 | 0.89 |
| LG-NCI-H460 | 1.66 | 1.52 | 0.66 |
| O-SKOV-3 | 0.316 | 0.277 | 0.046 |
| P-PC-3 | 0.636 | 1.58 | 0.601 |
| S-RH30 | 0.478 | 0.486 | 0.256 |

As shown in Table 4, the activity of compounds I-30 and I-33 are comparable to that of positive control GDC0941 (which was purchased from Shanghai han-xiang chemical co., LTD., dimesylate) against proliferation of various cell lines such as colon cancer cells C-HCT-116, colorectal cancer cells C-LOVO, endometrial cancer cells E-RL95-2, gastric cancer cells G-MKN-45, hepatoma cells L-BEL-7402, and rhabdomyosarcoma cells S-RH30. However, the activities of the compounds are significantly potent than the positive control in inhibiting the proliferation of B-BT474 cells.

The Inhibition Effects on the Growth of Human Neuroglioma U87-MG Xenograft Subcutaneously Transplanted in Nude Mouse Experimental Method Well-developed tumors in nude mice were cut into 1.5 mm$^3$ fragments and transplanted s.c. into the right flank of nude mice under sterile conditions. The diameters of subcutaneously transplanted tumours in nude mice were measured with a vernier calipe. When the tumour reached a volume 100-200 mm$^3$, the mice were randomly assigned into several groups: I-33 mesylate 50 mg/kg group and 25 mg/kg group; I-30 mesylate 50 mg/kg group; GDC0941 dimesylate 50 mg/kg group and control group. Control groups were given the same amount of blank solvent, and treatment groups received tested compounds (p.o.). Compounds were administered once a day for three weeks. Throughout the experiment, the sizes of the tumours were measured twice per week and meanwhile the body weights of mice were weighed. The tumour volume (TV) was calculated as follows: TV=½×a×b$^2$, wherein a and b represent the length and width, respectively. The individual relative tumour volume (RTV) was calculated as follows: RTV=V$_t$/V$_0$, where V$_0$ is the volume at the beginning of the treatment and V$_t$ is the volume measured every time. Evaluation index of antitumor activity was relative tumor proliferation rate T/C (%), the calculation formula of which was as follows: T/C(%)=(T$_{RTV}$/C$_{RTV}$)×100%, T$_{RTV}$: RTV of treatment group; C$_{RTV}$: RTV of negative control group.

Experimental Results

Figure 2:
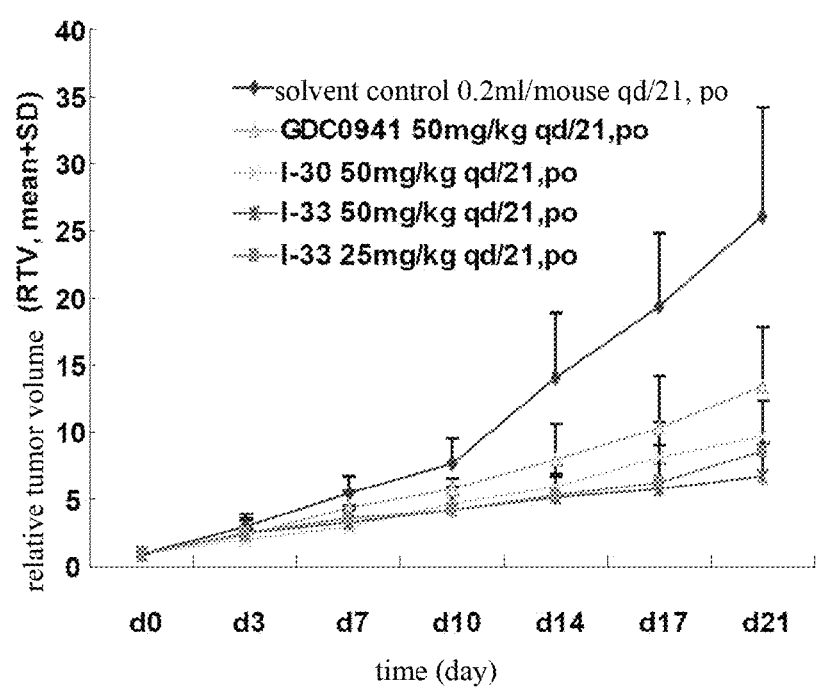
FIG. 2 shows the growth inhibition effects of I-30 and I-33 on subcutaneously transplanted tumors of human glioma U87MG in nude mice.

The experimental results were shown in table 5 and FIG. 2. I-33 mesylate was orally administrated at the dose of 50 mg/kg or 20 mg/kg every day. After one week, the growth of tumor in I-33 treated group significantly slowed down. After successively administrated for three weeks, I-33 mesylate significantly inhibited the growth of subcutaneously transplanted U87mG xenograft in nude mice (FIG. 2). The T/C value on the 21$^{st}$ day was 25.65% and 32.61%, respectively. I-33 mesylate displayed more potent activity than GDC0941 (50 mg/kg) in inhibiting the tumor growth. I-30 mesylate at 50 mg/kg also exhibited significant inhibitory effects on the tumor growth. The T/C value of I-30 mesylate at 50 mg/kg on the 21$^{st}$ day was 37.26%, while that of GDC0941 50 mg/kg group was 51.40%.

TABLE 5

Relative tumor growth rates of human neuroglioma U87-MG xenograft in nude mouse

| Group | Relative tumor proliferation rate T/C (%) | | | | | |
|---|---|---|---|---|---|---|
| | d0 | d3 | d7 | d10 | d14 | d17 | d21 |
| GDC0941 50 mg/kg | 100.00 | 75.12 | 79.34 | 74.75 | 56.86 | 53.57 | 51.40 |
| I-30 (mesylate) 50 mg/kg | 100.00 | 67.89 | 54.35 | 60.45 | 42.46 | 41.64 | 37.26 |
| I-33 (mesylate) 50 mg/kg | 100.00 | 82.76 | 59.61 | 54.74 | 36.93 | 29.89 | 25.65 |
| I-33 (mesylate) 20 mg/kg | 100.00 | 84.69 | 65.90 | 55.24 | 37.48 | 31.92 | 32.61 |

The invention claimed is:

1. A pyrrolo[2,1-f][1,2,4]triazine compound of formula I, or a pharmaceutically acceptable salt or hydrate thereof,

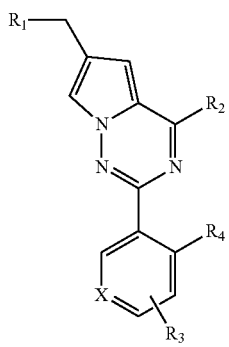

I wherein,
X=CH or N;
$R_1$ is —$NR_5R_6$;
$R_2$ is

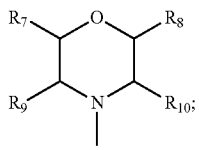

$R_3$ is —$NH_2$, —NHC(O)NH$R_{11}$, —NHC(O)O$R_{11}$, —NHC(O)$R_{11}$, —$CH_2OH$, —$CH_2S(O)_2R_{12}$ or —$CH_2NHS(O)_2R_{12}$;
$R_4$ is H or $CF_3$;
$R_5$ and $R_6$ are each independently a C1-C4 alkyl, or combined with the nitrogen atom to which they are attached to form an unsubstituted 5-8 membered saturated heterocycle or a 5-8 membered saturated heterocycle substituted by a substituent, the substituent is —$S(O)_2R_{12}$;
$R_7$, $R_8$, $R_9$ and $R_{10}$ are each independently H or a C1-C3 alkyl, alternatively, $R_7$ and $R_8$, or $R_9$ and $R_{10}$, with the carbon atoms to which they are attached as bridge carbon atoms, form bridged bicylco-heterocycle with morpholine ring;
$R_{11}$ is a C1-C4 alkyl, an unsubstituted C3-C6 cycloalkyl or a C3-C6 cycloalkyl substituted by one or more substituents, an unsubstituted benzyl or a benzyl substituted by one or more substituents, an unsubstituted phenyl or a phenyl substituted by one or more substituents, an unsubstituted isoxazolyl or an isoxazolyl substituted by one or more substituents, or an unsubstituted pyridyl or a pyridyl substituted by one or more substituents, and the one or more substituents are selected from halogen, a C1-C3 alkyl, or a C1-C3 alkoxyl, —$CF_3$, —$C(O)OR_{12}$, —$C(O)NR_{12}R_{15}$,

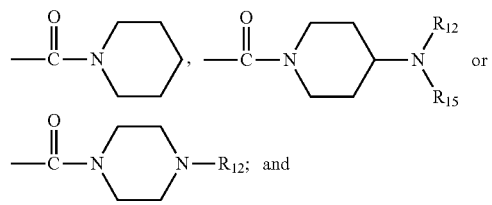

$R_{12}$ and $R_{15}$ are each independently a C1-C3 alkyl.

2. The pyrrolo[2,1-f][1,2,4]triazine compound, or the pharmaceutically acceptable salt or hydrate thereof of claim 1, wherein the compound has the following structure shown in formula A or formula B:

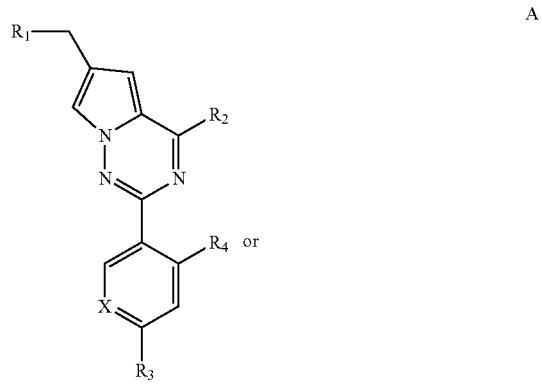

A

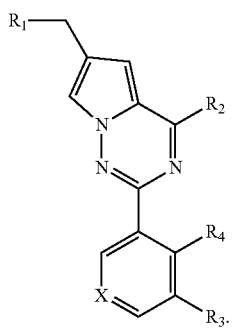

B

3. The pyrrolo[2,1-f][1,2,4]triazine compound, or the pharmaceutically acceptable salt or hydrate thereof of claim 1, wherein, R₂ is

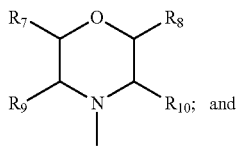

R₅ and R₆ are combined with the nitrogen atom to which they are attached to form an unsubstituted saturated heterocycle or a saturated heterocycle substituted by a substituent, wherein the saturated heterocycle is pyrrolidyl, piperidinyl or piperazinyl, and the substituent is —S(O)₂R₁₂.

4. The pyrrolo[2,1-f][1,2,4]triazine compound, or the pharmaceutically acceptable salt or hydrate thereof of claim 3, wherein, R₁ is dimethylamino or 1-methylsulfonyl piperazinyl;

R₂ is

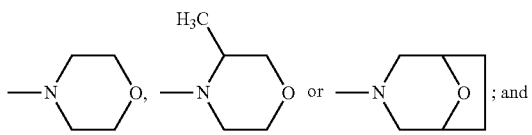

R₁₁ is a methyl, an ethyl, a propyl, a cyclopropyl, a tert-butyl, an iso-butyl, a 4-fluorobenzyl, an unsubstituted phenyl or a phenyl substituted by one or more substituents, an unsubstituted isoxazolyl or an isoxazolyl substituted by one or more substituents, or an unsubstituted pyridine ring or a pyridine ring substituted by one or more substituents, and the substituent is selected from the group consisting of a fluorine, a chlorine, a trifluoromethyl, a methyl, a methoxy, an ethoxycarbonyl, a dimethylaminocarbonyl, a 4-methyl-piperazine-1-carbonyl, a piperidine-1-carbonyl and a 4-dimethylamino-piperidine-1-carbonyl.

5. The pyrrolo[2,1-f][1,2,4]triazine compound, or the pharmaceutically acceptable salt or hydrate thereof of claim 1, wherein the compound has the following structure of formula:

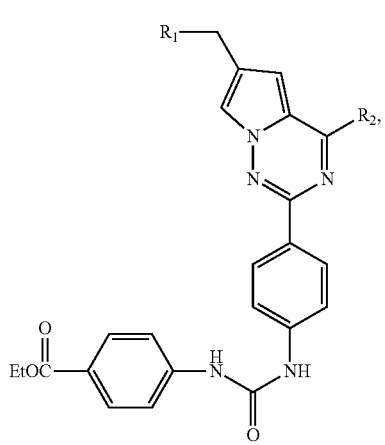

Ia

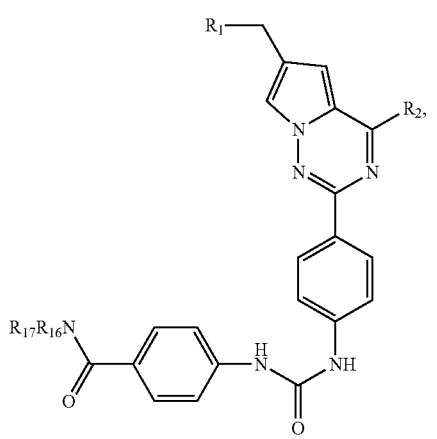

Ib

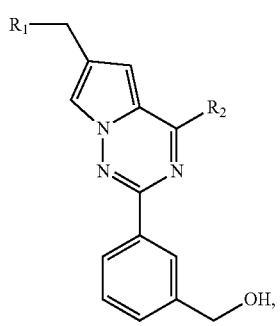

Ic

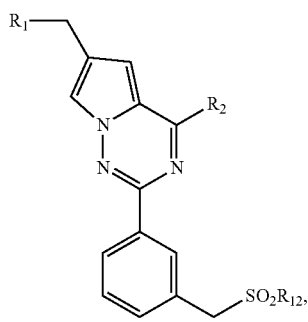

Id

-continued

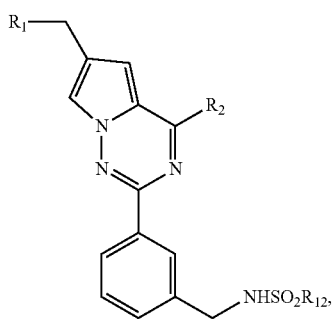

Ie

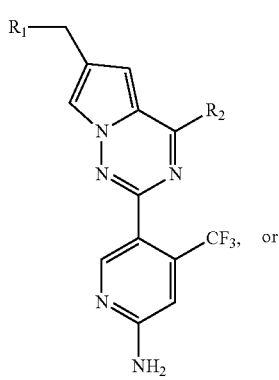

If

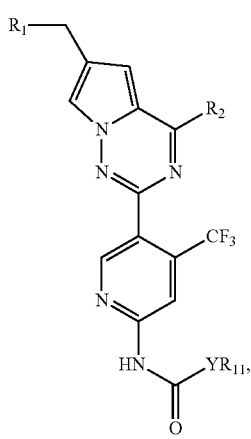

Ig

Y = NH or O

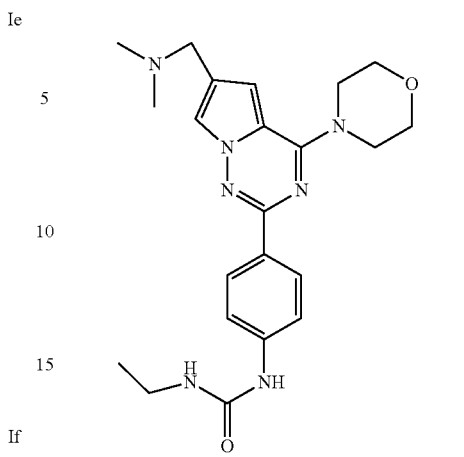

I-1

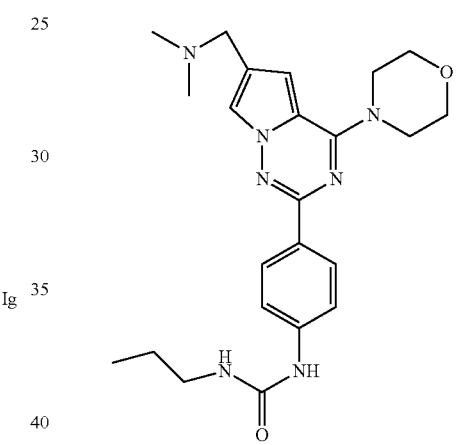

I-2

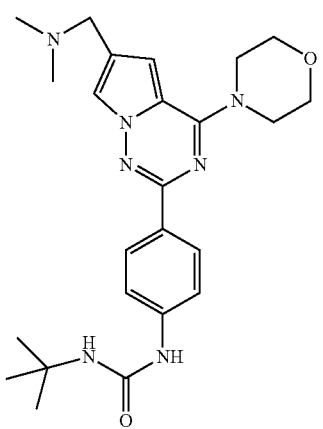

I-3 wherein, $R_1$, $R_2$, $R_{11}$ and $R_{12}$ are defined as in claim 1, and $R_{16}$ and $R_{17}$ are identical or different, and each is independently selected from a C1-C4 alkyl, or $R_{16}$ and $R_{17}$ are combined with the nitrogen atom to which they are attached to form a 4-methyl-piperazinyl, a 4-dimethyl-amino-piperidinyl or piperidin-1-yl.

6. The pyrrolo[2,1-f][1,2,4]triazine compound, or the pharmaceutically acceptable salt or hydrate thereof of claim 1, wherein the compound has the following structure of formula:

-continued
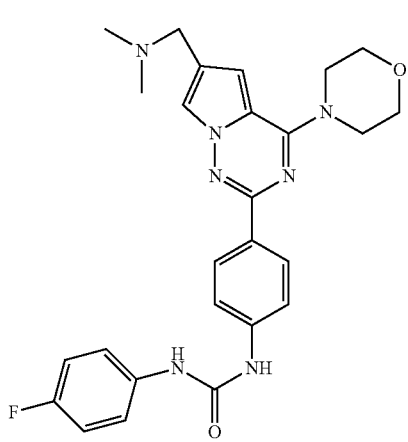
I-4
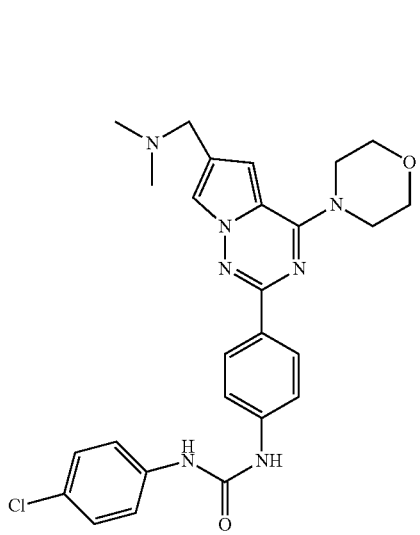
I-5
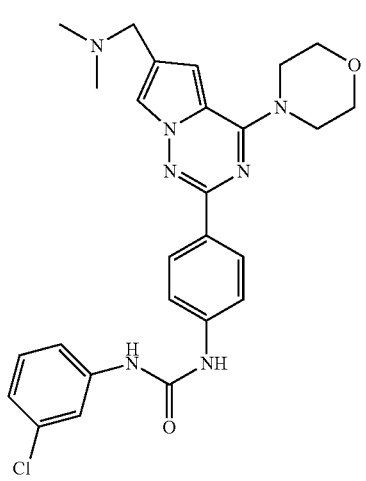
I-6
-continued
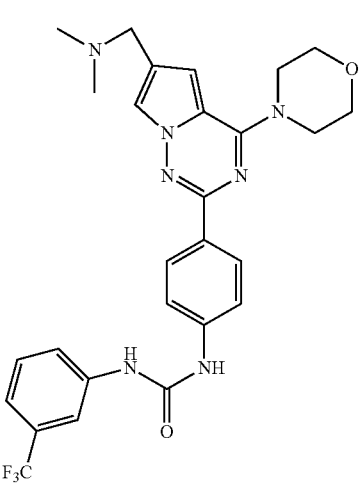 
I-7
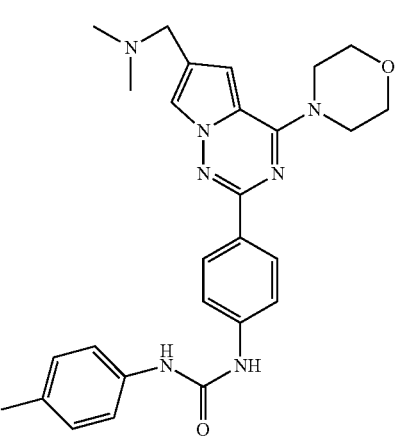
I-8
I-9

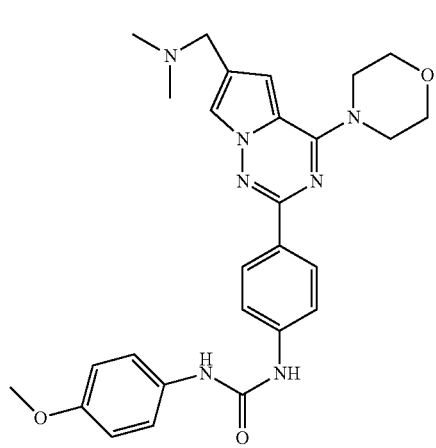
I-10
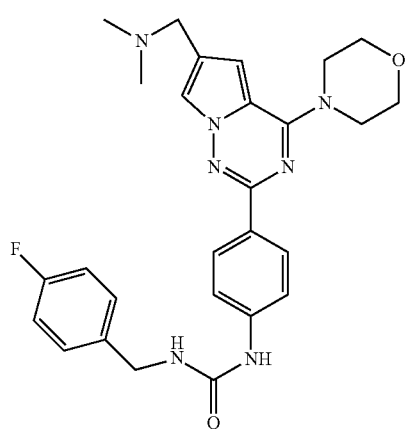
I-11
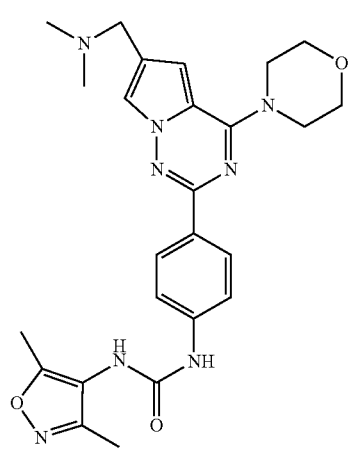
I-12
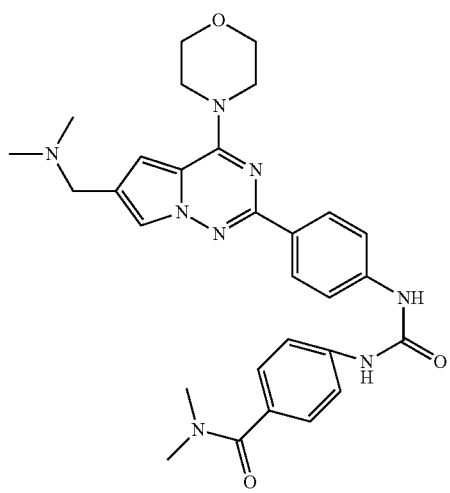
I-13
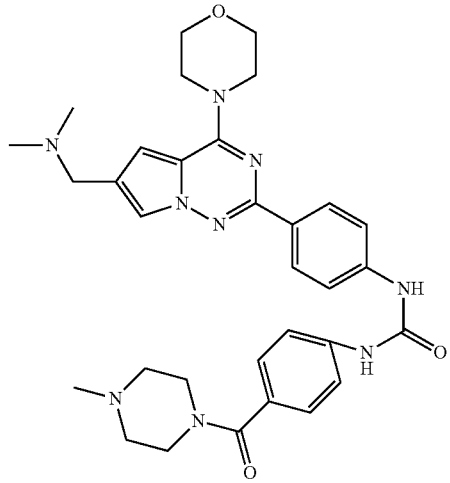
I-14
I-15

I-16
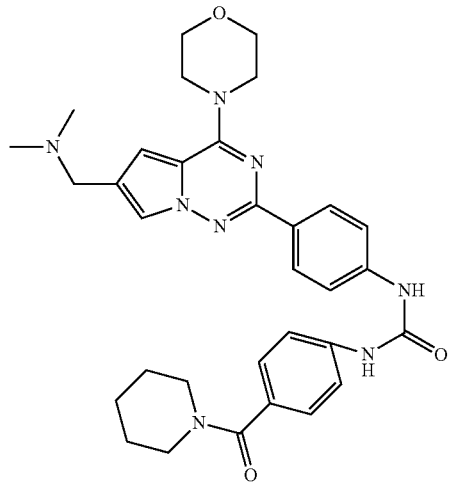
I-19
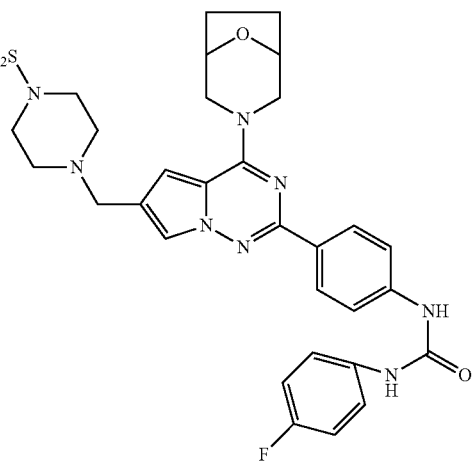
I-17
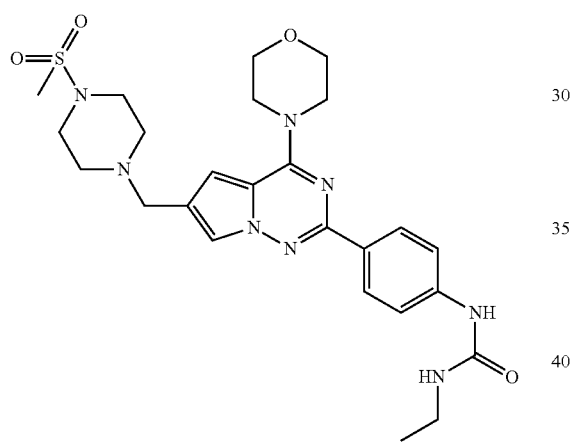
I-20
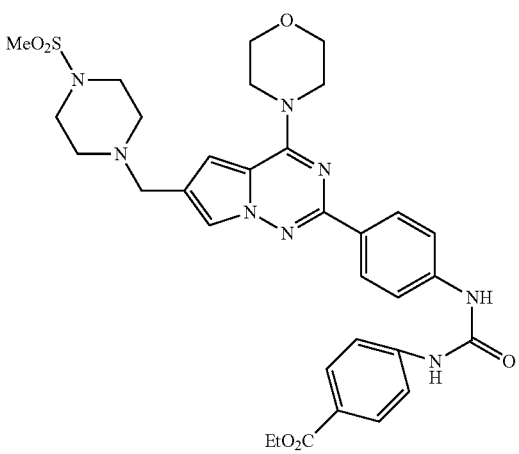
I-18
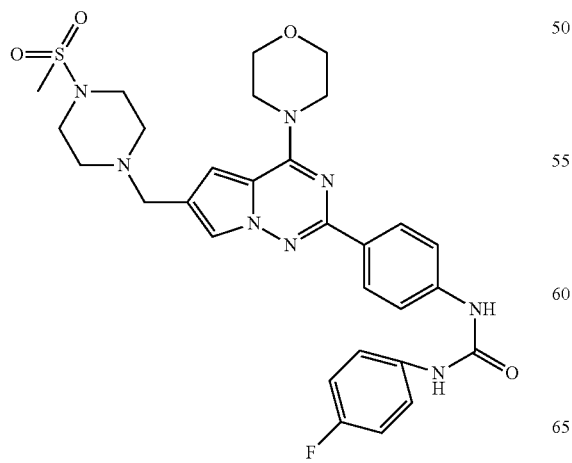
I-21
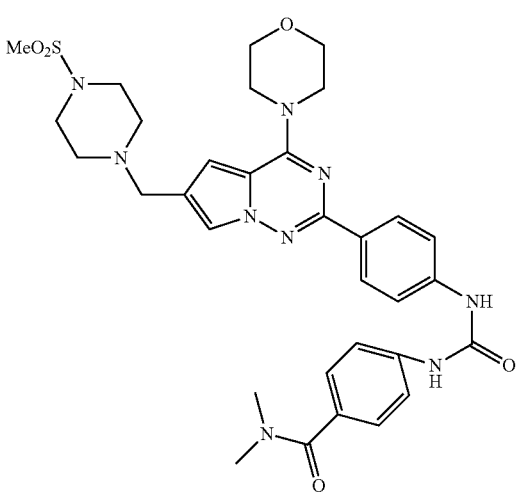

-continued
I-22
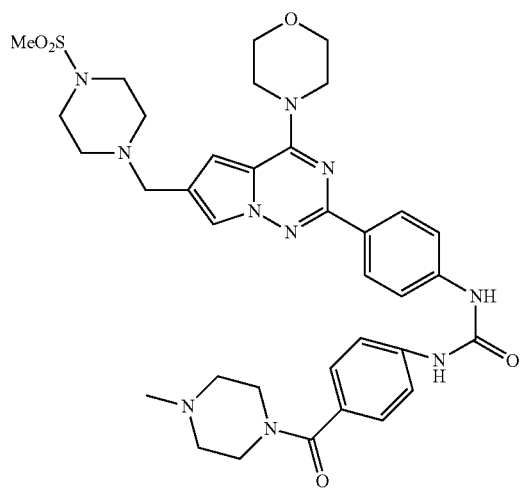
I-23
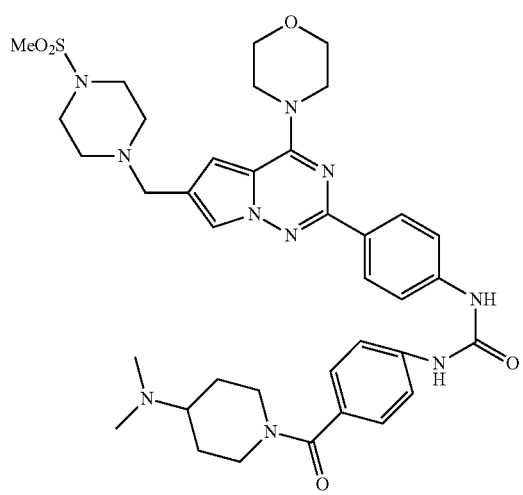
I-24
I-25
-continued
I-26
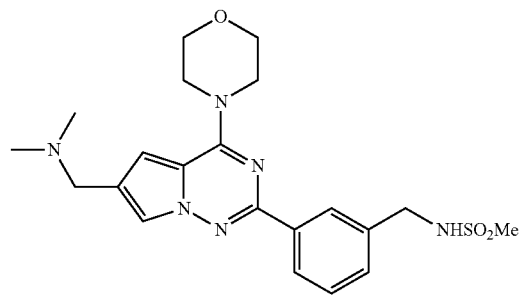
I-27
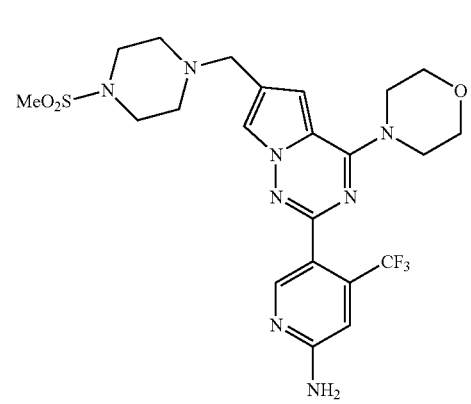
I-28
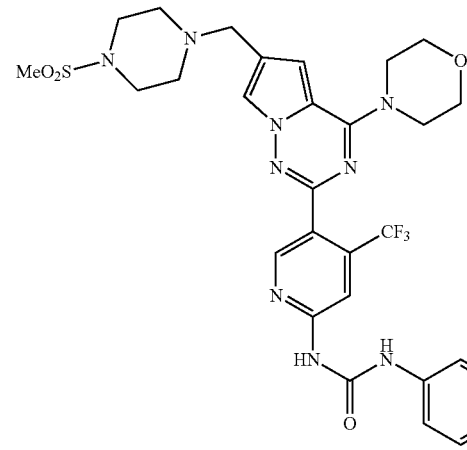
I-29
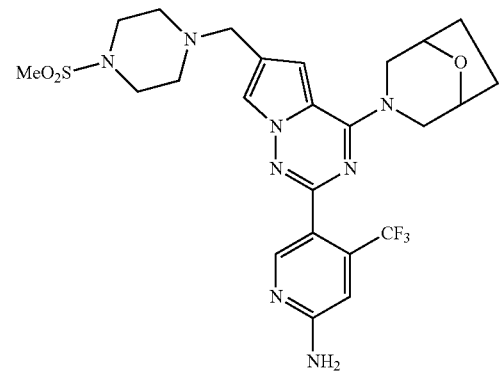

I-30
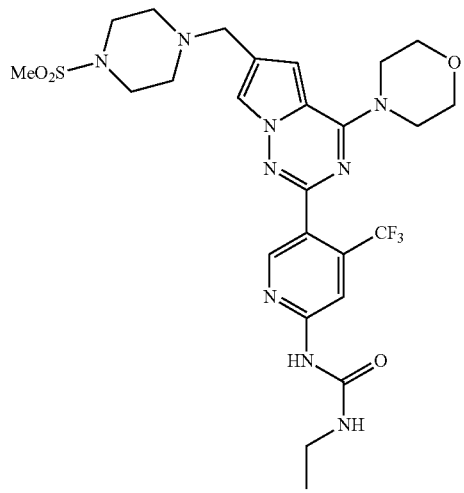
I-31
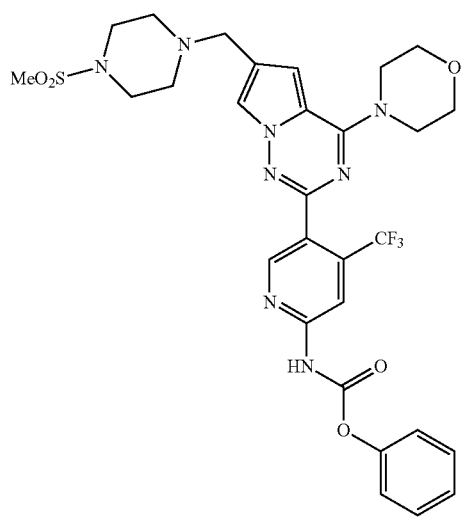
I-32
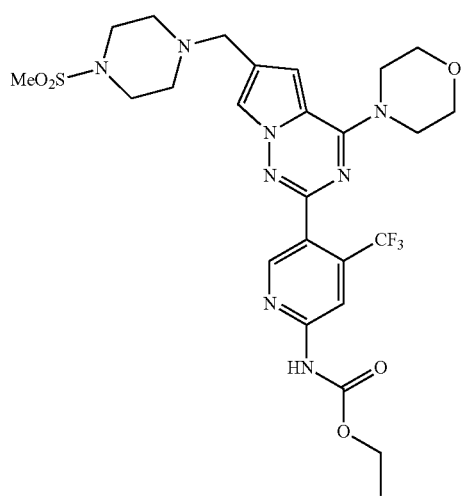
I-33
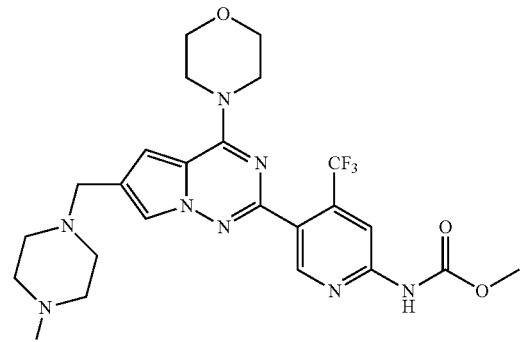
I-34
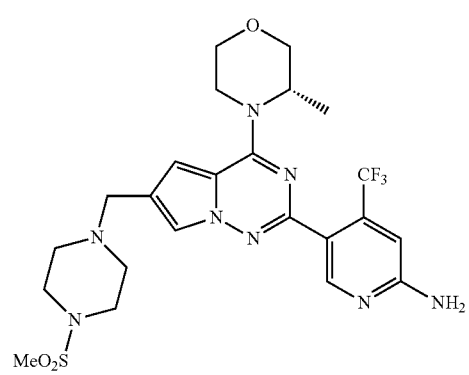
I-35
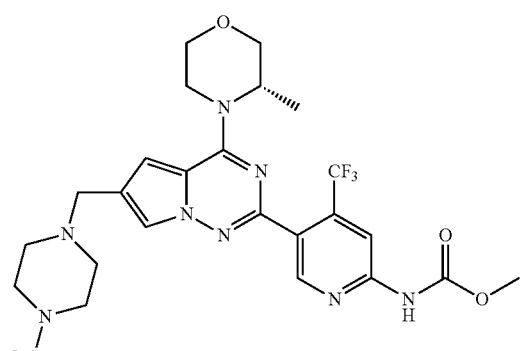
I-36
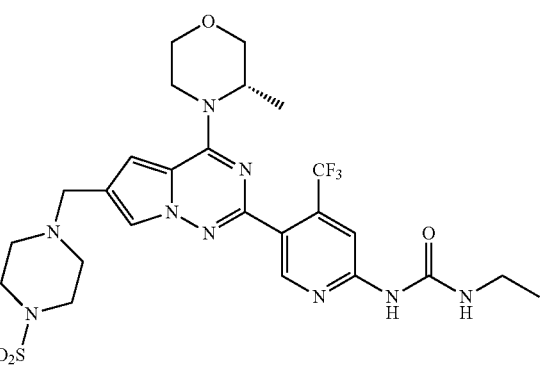

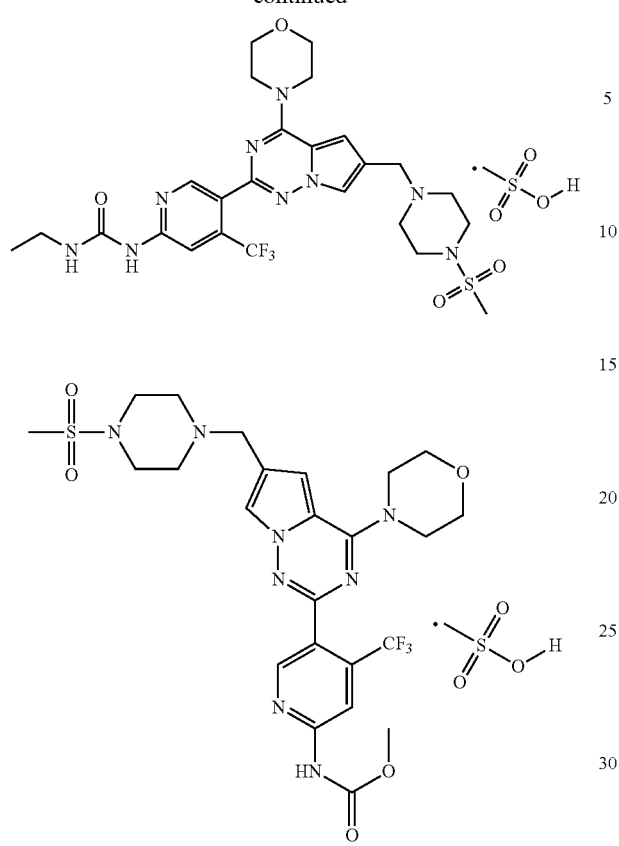
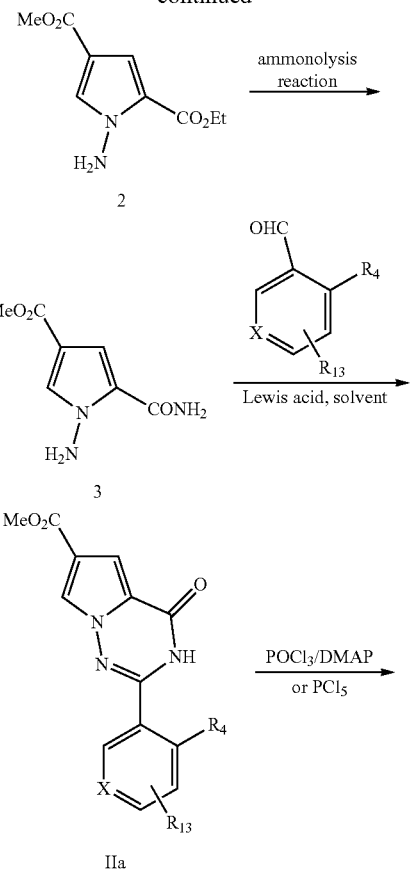
7. A preparation method for the pyrrolo[2,1-f][1,2,4] triazine compounds of claim 1, comprising the following steps:
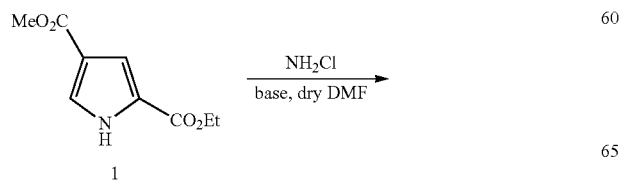
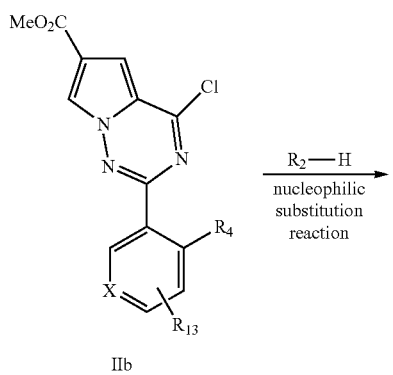

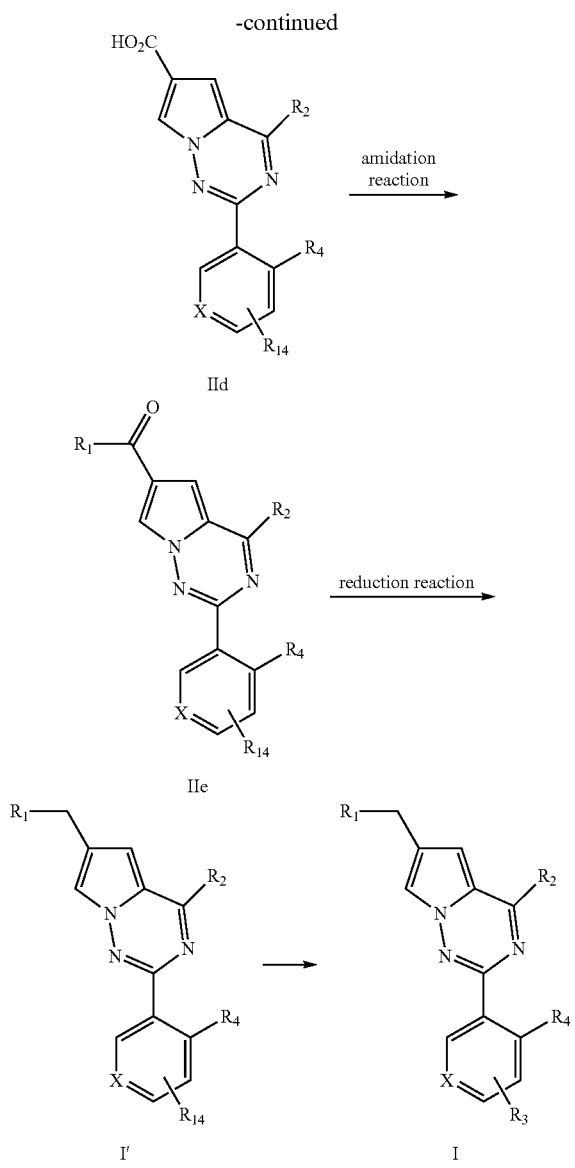

wherein, $R_{13}$ is a nitro or —$CH_2OAc$; $R_{14}$ is an amino or —$CH_2OH$;

1) pyrrole derivative 1 and chloramine in anhydrous N,N-dimethylformamide are subjected to N-amination reaction in the presence of a base to obtain compound 2;
2) the compound represented by Formula 2 without being purified is subjected to ammonolysis to give compound 3;
3) compound 3 reacts with an aromatic aldehyde under the action of metal Lewis acid to give compound IIa, or compound 3 and an aldehyde, under catalysis by Lewis acid such as a solution of boron trifluoride in diethyl ether, are subjected to condensation to give a Schiff base, and then to oxidative cyclization to give compound IIa;
4) compound IIa is subjected to chlorination reaction in the presence of a base to give compound IIb;
5) compound IIb and $R_2$—H are subjected to nucleophilic substitution reaction to give compound IIc;
6) the ester group of compound IIc is subjected to hydrolysis reaction; or the nitro group of compound IIc is subjected to reduction reaction, and then the ester group of compound IIc is hydrolyzed;
7) compound IId reacts with a $R_1$—H amine or a substituted or unsubstituted 3-8 membered saturated heterocycle containing at least one nitrogen atom to give compound I', and the substituent is —$S(O)_2R_{12}$;
8) compound IIe is reduced by a reducing agent to give compound I'; and
9) compound I' is further subjected to addition reaction with $R_{11}NCO$, to esterification reaction or amidation reaction with $R_{11}OC(O)Cl$, to esterification reaction or amidation reaction with $R_{11}C(O)OH$ or $R_{11}C(O)Cl$, or to esterification reaction or amidation reaction with $R_{12}S(O)_2Cl$ thereby converting $R_{14}$ in compound I' into $R_3$ and forming the compounds represented by the formula I.

8. The preparation method of claim 7, wherein,
the base in step 1) is sodium hydride, potassium carbonate or potassium tert-butoxide;
the metal Lewis acid in step 3) can be a monovalent or divalent copper reagent, and the reaction temperature is 80-150° C.;
the chlorination agent in step 4) is phosphorus oxychloride or phosphorus pentachloride, and the base used is N,N-dimethylaniline or 4-dimethylaminopyridine;
the amine in step 7) is dimethylamine or 1-methylsulfonyl piperazine; and
the reducing agent in step 8) is borane-tetrahydrofuran complex or borane-dimethyl sulfide complex.

9. The preparation method of claim 8, wherein,
the copper reagent is cuprous bromide, cuprous chloride, copper acetate monohydrate, copper bromide, anhydrous copper chloride, or copper chloride dihydrate; and the reaction solvent is dimethyl sulfoxide or N,N-dimethylformamide, N,N-dimethylacetamide.

10. A method for inhibiting phosphatidylinositol 3-kinase in cancer cells, the method comprising administering to a subject in need thereof a pyrrolo[2,1-f][1,2,4]triazine compound of claim 1, wherein the subject is a human patient having a cancer selected from the group consisting of human rhabdomyosarcoma, non-small cell lung cancer, human glioma, prostate cancer, ovarian cancer, liver cancer, colon cancer, and breast cancer.

11. The pyrrolo[2,1-f][1,2,4]triazine compound, or the pharmaceutically acceptable salt or hydrate thereof of claim 2, wherein,
$R_2$ is

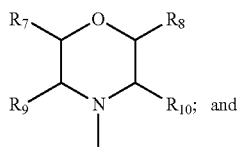

$R_5$ and $R_6$ are combined with the nitrogen atom to which they are attached to form an unsubstituted saturated heterocycle or a saturated heterocycle substituted by a substituent, wherein the saturated heterocycle is pyrrolidyl, piperidinyl or piperazinyl, and the substituent is —$S(O)_2R_{12}$.

* * * * *

UNITED STATES PATENT AND TRADEMARK OFFICE
CERTIFICATE OF CORRECTION

PATENT NO. : 9,447,101 B2  
APPLICATION NO. : 14/403014  
DATED : September 20, 2016  
INVENTOR(S) : Chunhao Yang et al.

Page 1 of 1

It is certified that error appears in the above-identified patent and that said Letters Patent is hereby corrected as shown below:

In the Claims

In Claim 7, Column 108, Line 8, replace "compound I'," with -- compound IIe, --

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*